US006617442B1

(12) United States Patent
Crooke et al.

(10) Patent No.: US 6,617,442 B1
(45) Date of Patent: Sep. 9, 2003

(54) HUMAN RNASE H1 AND OLIGONUCLEOTIDE COMPOSITIONS THEREOF

(75) Inventors: Stanley T. Crooke, Carlsbad, CA (US); Walter F. Lima, San Diego, CA (US); Hongjiang Wu, Carlsbad, CA (US); Muthiah Monoharan, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/409,926

(22) Filed: Sep. 30, 1999

(51) Int. Cl.$^7$ ............... C07H 21/04; C07H 21/02; C07H 21/00; C12Q 1/68; C12P 19/34

(52) U.S. Cl. ............... 536/24.5; 435/6; 435/91.1; 435/91.5; 536/23.1; 536/24.5; 536/25.3

(58) Field of Search ............... 435/6, 91.1, 91.31, 435/91.5, 91.51, 366, 375, 443, 455; 514/44, 45, 49; 536/23.1, 24.5, 25.3, 25.32, 25.6, 27.4; 935/34, 36

(56) References Cited

U.S. PATENT DOCUMENTS

| | | | |
|---|---|---|---|
| 3,687,808 A | 8/1972 | Merigan et al. ............... 435/91.3 |
| 4,981,957 A | 1/1991 | Lebleu et al. ............... 536/25.2 |
| 5,118,800 A | 6/1992 | Smith et al. ............... 536/23.1 |
| 5,212,295 A | 5/1993 | Cook ............... 536/26.7 |
| 5,319,080 A | 6/1994 | Leumann ............... 536/27.1 |
| 5,359,044 A | 10/1994 | Cook et al. ............... 536/23.1 |
| 5,393,878 A | 2/1995 | Leumann ............... 536/28.2 |
| 5,446,137 A | 8/1995 | Maag et al. ............... 536/23.1 |
| 5,466,786 A | 11/1995 | Buhr et al. ............... 536/26.26 |
| 5,514,785 A | 5/1996 | Van Ness et al. ............... 536/22.1 |
| 5,519,134 A | 5/1996 | Acevedo et al. ............... 544/243 |
| 5,567,811 A | 10/1996 | Misiura et al. ............... 536/25.34 |
| 5,576,208 A | 11/1996 | Monia et al. ............... 435/240.2 |
| 5,576,427 A | 11/1996 | Cook et al. ............... 536/23.1 |
| 5,591,722 A | 1/1997 | Montgomery et al. ........ 514/45 |
| 5,597,909 A | 1/1997 | Urdea et al. ............... 536/24.3 |
| 5,610,300 A | 3/1997 | Altmann et al. ............... 544/244 |
| 5,623,065 A * | 4/1997 | Cook et al. ............... 536/23.1 |
| 5,627,053 A | 5/1997 | Usman et al. ............... 435/91.1 |
| 5,639,649 A | 6/1997 | Almond et al. ............... 435/235.1 |
| 5,639,873 A | 6/1997 | Barascut et al. ............... 536/25.3 |
| 5,646,265 A | 7/1997 | McGee ............... 536/25.34 |
| 5,652,355 A | 7/1997 | Metelev et al. ............... 536/24.5 |
| 5,658,873 A | 8/1997 | Bertsch-Frank et al. .... 510/375 |
| 5,670,633 A | 9/1997 | Cook et al. ............... 536/23.1 |
| 5,672,695 A * | 9/1997 | Eckstein et al. ............... 536/24.5 |
| 5,700,922 A | 12/1997 | Cook ............... 536/23.1 |
| 5,801,154 A * | 9/1998 | Baracchini et al. ............... 514/44 |
| 5,859,221 A | 1/1999 | Cook et al. ............... 536/23.1 |
| 5,955,589 A * | 9/1999 | Cook et al. ............... 536/23.1 |
| 6,001,653 A * | 12/1999 | Crooke et al. ............... 435/375 |

FOREIGN PATENT DOCUMENTS

EP  0 788 366 B1 *  8/1997

WO  WO 89/12060  12/1989

OTHER PUBLICATIONS

Brett P. Monia et al., Evaluation of 2'–Modified Oligonucleotides Containing 2'–Deoxy Gaps as Antisense Inhibitors of Gene Expression, The Journal of Biological Chemistry, vol. 268, No. 19, pp. 14514–14522 Jul. 5, 1993.*
M. J. Damha et al., Hybrids of RNA and Arabinobucleic Acids (ANA and 2'F–ANA) Are Substrates of Ribonuclease H, J. Am. Chem. Soc. 1998, 120, pp. 12976–12977.*
Andrew M. Kawasake et al., Uniformly Modified 2'–Deoxy–2'–fluoro Phosphorothioate Oligonucleotides as Nuclease–Resistant Antisense Compounds with High Affinity and Specificity for RNA Targets; J. Med. Chem. 1993, vol. 36, pp. 831–841.*
Susan M. Freier et al., The ups and downs of nucleic acid duplex stability: structure–stability studies on chemically–modified DNA:RNA duplexes; Nucleic Acids Research, 1997, vol. 25, No. 22, pp. 4429–4443.*
Eugen Uhlmann et al., Antisense Oligonucleotides: A New Therapeutic Principle; Chemical Reviews, 1990, vol. 90, No. 4 pp. 543–584.*
A.M. Kawasaki et al 1993 J. Med. Chem. vol. 36, pp. 831–841.*
E. Uhlmann et al. 1990 Chemical Reviews vol. 90, No. 48: pp. 543–579.*
Crooke, S.T., "Molecular mechanisms of antisense drugs: RNase H," *Antisense & Nucleic Acid Drug Development*, 1998, XP–000946837, 8, 133–134.
EPO Supplementary European Search Report dated Oct. 16, 2002, EP 00 96 5513.
Boado, R.J., et al., "Complete inactivation of target mRNA by biotinylated antisense oligodeoxynucleotide—avidin conjugates," *Bioconjugate Chem.*, 1994, 5, 406–410.
Bordier, B., et al., "Sequence–specific inibition of human immunodeficiency virus (HIV) reverse transcription by antisense oligonucleotides: comparative study in cell–free assays and in HIV–infected cells," *Proc. Natl. Acad. Sci. USA*, 1995, 92, 9383–9387.
Chiang, M., et al., "Antisense oligonucleotides inhibit intercellular adhesion molecule 1 expression by two distinct mechanisms," *J. Biological Chemistry*, 1991, 266(27), 18162–18171.
Dagle, J., et al., "Targeted degradation of mRNA in Xenopus oocytes and embryos directed by modified oligonucleotides: studies of An2 and cyclin in embryogenesis," *Nucleic Acids Res.*, 1990, 18(16), 4751–4757.
Frank, P., et al., Cloning, subcellular localization and functional expression of human Rnase HII, *Biol. Chem.*, 1998, 379, 1407–1412.

(List continued on next page.)

*Primary Examiner*—Sean McGarry
*Assistant Examiner*—Jane Zara
(74) *Attorney, Agent, or Firm*—Woodcock Washburn LLP

(57) ABSTRACT

The present invention provides oligonucleotides that can serve as substrates for human Type 2 RNase H. The present invention is also directed to methods of using these oligonucleotides in enhancing antisense oligonucleotide therapies.

7 Claims, 6 Drawing Sheets

OTHER PUBLICATIONS

Frank, P., et al., "Cloning of the cDNA encoding the large subunit of human Rnase HI, a homologue of the prokaryotic Rnase HII," *Proc. Natl. Acad. Sci. USA*, 1998, 95, 12872–12877.

Furdon, P.J. et al., "Rnase H cleavage of RNA hybridized to oligonucleotides containing methylphosphonate, phosphorothioate and phosphodiester bonds," *Nucleic Acids Res.*, 1989, 17, 9193–9204.

Giles, R.V., "Increased specificity for antisense oligodeoxynucleotide targeting of RNA cleavage by Rnase H using chimeric methylphosphonodiester/phosphodiester structures," *Nucleic Acids Res.*, 1992, 20(4), 763–770.

Giles, R.V., "Enhanced Rnase H activity with methylphosphonodiester/phosphodiester chimeric antisense oligodeoxynucleotides," *Anti–Cancer Drug Design*, 1992, 7, 37–48.

Ghosh, M.K., et al., "Phosphorothioate–phosphodiester oligonucleotide co–polymers: assessment for antisense application," *Anti–Cancer Drug Design*, 1993, 8, 15–32.

Godard, G., et al., "Antisense effects of cholesterol–oligodeoxynucleotide conjugates associated with poly (alkylcyanoacrylate) nanoparticles," *Eur. J. Biochem.*, 1995, 232, 404–410.

Gottikh, M., et al, "αβ Chimeric antisense oligonucletides: synthesis and nuclease resistance in biological media," *Antis. Res. And Dev.*, 1994, 4, 251–258.

Hoke, G.D., et al., "effects of phosphorothioate capping on antisense oligonucleotide stability, hybridization and antiviral efficacy versus herpes simplex virus infection," *Nucleic Acids Res.*, 1991, 19(20), 5743–5748.

Kawasaki, E.S., "Quantitative hybridization–arrest of mRNA in Xenopus oocytes using single–stranded complementary DNA or oligonucleotide probes," *Nucleic Acids Res.*, 1985, 13(13), 4991–5005.

Krainer, A.R., et al., "Multiple factors including the small nuclear ribonucleoproteins U1 and U2 are necessary for pre–mRNA splicing in vitro," *Cell*, 1985, 42, 725–736.

Lee, et al., "Antisense gene suppression against human ICAM–1, ELAM–1, and VCAM–1 in cultured human umiblical vein endothelial cells," *SHOCK*, 1995, 4(1), 1–10.

Liu, P.K., et al., "Suppression of ischemia–induced fos expression and AP–1 activity by an antisense oligodeoxynucleotide to c–fos mRNA," *Am. Neurol. Assoc.*, 1994, 566–576.

Quartin, R.S., et al., "Number and distribution of methylphosphonate linkages in oligodeoxynucleotides affect exo–and endonuclease sensitivity and ability to form Rnase H substrates, " *Nucleic Acids Res.*, 1989, 17(8), 7253–7262.

Rosolen, A., et al., "Effect of over–expression of bacterial ribonuclease H on the utility of antisense MYC oligodeoxynucleotides in the monocytic leukemia cell line U937," *Biochimie*, 1993, 75, 79–87.

Wu, H., et al., "Molecular cloning and expression of cDNA for human Rnase H," *Antisense Nucleic Drug Development*, 1998, 8, 53–61.

Abe, A. et al., "Conformational Energies and the Random–Coil Dimensions and Dipole Moments of Polyoxides CH3O [(CH2)]yO]xCH3," *J. Am. Chem. Soc.*, 1976, 6468–6476.

Agrawal, Sudhir, et al., "Site–specific excision from RNA by Rnase H and mixed–phosphate–backbone oligodeoxynucleotides," *Proc. Nutl. Acad. Sci. USA*, 1990, 87, 1401–1405.

Baker, B.F. et al., "2'–O–(2–Methoxy)ethyl–modified Anti-intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11994–12000.

Berger, I. et al., "Crystal structures of B–DNA with incorporated 2'–deoxy–2'–fluoro–arabino–furanosyl thymines: implications of conformational preorganization for duplex stability," *Nucl. Acids Res.*, 1998, 26(10), 2473–2480.

Blake et al., "Hybridization Arrest of Globin Synthesis in Rabbit Reticulocyte Lysates and Cells by Oligodeoxyribonucleoside Methylphosphonates," *Biochem.*, 1985, 24, 6139–4145.

Busen, W., The Subunit Structure of Calf Thymus Ribonuclease HI As Revealed by Immunological Analysis, *J. Biol. Chem.*, 1982, 257(12), 7106–7108.

Busen, W. et al., "Distinct Ribonuclease H Activities in Claf Thymus," *Eur. J. Biochem.*, 1975, 52, 179–190.

Busen, W., "Purification, Subunit Structure, and Serological Analysis of Calf Thymus Ribonuclease HI," *J. Biol. Chem.*, 1980, 255(19), 9434–9443.

Busen et al., "Ribonuclease H Levels during the Response of Bovine Lymphocytes to Concanavalin A," *Eur. J. Biochem.*, 1977, 74, 203–208.

Cazenave et al., "Comparative inhibition of rabbit globin mRNA translation by modified antisense oligodeoxynucleotides," *Nucleic Acid Res.*, 1989, 17(11), 4255–4273.

Cook, P.D., "Medicinal Chemistry of Antisense Oligonucleotides—future opportunities", *Anti–Cancer Drug Design*, 1991, 6, 585–607.

Cornell, W. D. et al., "A Second Generation Force Field for the Simulation of Proteins, Nucleic Acids, and Organic Molecules," *J. Am. Chem. Soc.*, 1995, 117, 5179–5197.

Cory, A.H. et al., "2'–Deoxy–2'–Methylene Derivatives of Adenosine, Guanosine, Tubercidin, Cytidine and Uridine as Inhibitors of L1210 Cell Growth in Culture," *Biochemical Pharmacology*, 1994, 47(2), 365–371.

Cowsert, L. M. et al., "In vitro and In Vivo Activity of Antisense Inhibitors of ras: Potential for Clinical Development," *Anti–Cancer Drug Design*, 1997, 12, 359–371.

Crooke, S.T. et al., "Kinetic characteristics of *Escherichia coli* RNase H1: cleavage of various antisense oligonucleotide–RNA duplexes", *Biochem. J.*, 1995, 312, 599–608.

Crooke, S.T. et al., "Pharmokinetic Properties of Several Novel Oligonucleotide Analogs in mice", *J. Pharmocol. Exp. Therapeutics*, 1996, 277, 923–937.

Crouch, R. J. et al., *Nuclease*, Linn, S.M. et al. (eds.), Cold Spring Harbor Laboratory Press, Plainview, NY, 1982, 211–241.

Damha, M.J. et al., "An improved procedure for derivatization of controlled–pore glass beads for solid–phase oligonucleotide synthesis", *Nucl. Acids Res.*, 1990, 18, 3813–3821.

Damha, M.J. et al., "Hybrids of RNA and Arabinonucleic Acids (ANA and 2'F–ANA) Are Substrates of Ribonuclease H," *J.Am.Chem.Soc.*, 1998, 120, 12976–12977.

Dash et al., "Selective elimination of mRNAs in vivo: Complementary oligodeoxynucleotides promote RNA degradation by an RNase H–like activity," *Proc. Nat'l Acad. Sci. USA*, 1987, 84, 7896–7900.

De Mesmaeker, A. et al., "Antisense Oligonucleotides",*Acc. Chem. Res.*, 1995, 28, 366–374.

Dean, N.M. et al., "Inhibition of protein kinase C–α expression in mice after systemic administration of phosphorthioate antisense oligodeoxynucleotides", *Proc. Natl. Acad. Sci.*, 1994, 91, 11762–11766.

Delgado, C. et al., "The Uses and Properties of PEG–Linked Proteins", *Crit. Rev. in Therapeutic Drug Carrier Sys.*, 1992, 9, 249–304.

Dimock, S. et al., "An Efficient Multigram Synthesis of Monomers for the Preparation of Novel Oligonucleotides Containing Isosteric Non–Phosphorous Backbones," *Nucleosides & Nucleotides*, 1997, 16(7–9), 1629–1632.

Eder et al., "Substrate specificity of human RNase H1 and its role in excision repair of ribose residues misincorporated in DNA," *Biochimie*, 1993, 75, 123–126.

Flanagan, W.M. et al., "Cellular penetration and antisense activity by a phenoxazine–substituted heptanucleotide," *Nature Biotechnology*, 1999, 17, 48–52.

Frank et al., "Purification and characterization of human ribonuclease HII," *Nucleic Acids Res.*, 1994, 22(24), 5247–5254.

Fraser, A. et al., "Synthesis and Conformational Properties of 2'-Deoxy-2'-methylthiopyrimidine and–purine Nucleosides: Potential Antisense Applications," *J. Heterocyclic Chem.*, 1993, 30, 1277–1287.

Freier, S.M. et al., "The ups and downs of nucleic acid duplex stability: structure–stability studies on chemically-modified DNA:RNA duplexes", *Nucl. Acids Res.*, 1997, 25, 4429–4443.

Gaffney, B.L. et al., "A New Strategy for the Production of Deoxyguanosine During Oligonucleotide Synthesis", *Tetrahedron Letts.*, 1982, 23, 2257–2260.

Gagnor, C. et. al., "α–DNA VI: Comparative Study of α– and β–Anomeric Oligodeoxyribonucleotides in Hybridization to mRNA and in Cell Free Translation Inhibition", *Nucl. Acids Res.*, 1987, 15, 10419–10436.

Gotfredsen, C.H. et al., "Novel Oligodeoxynucleotide Analogues Containing A 2'-O-Methylarabinonucleoside," *Tetrahedron Letts.*, 1994, 35(37), 6941–6944.

Gotfredsen, C.H. et al., "Synthesis and Properties of a– and B–Oligodeoxynucleotides Containing a–and B–1–(2–O–Methyl–D–arabino–furanosyl) thymine," *Bioorganic & Medicinal Chemistry*, 1996, 4(8), 1217–1225.

Guzaev A. et al., "Synthesis of C–Radiolabeled Oligonucleotides with a Novel Phosphoramidite Reagent," *Bioorg. & Med. Chem. Lett.*, 1998, 8, 1123–1126.

Hall, K. B. et al., "Thermodynamic and Structural Properties of Pentamer DNA·DNA, RNA·RNA, and DNA·RNA Duplexes of Identical Sequence," *Biochemistry*, 1991, 30, 10606–10613.

Hamm, M. L. et al., "Incorporation of 2'-Deoxy-2'-mercaptocytidine into Oligonucleotides via Phosphoramidite Chemistry," *J. Org. Chem.*, 1997, 62, 3415–3420.

Hansske, F. et al., "Nucleic Acid Related Compounds. 43. A Convenient Procedure for the Synthesis of 2' and 3'-Ketonucleosides," *Tetrahedron Letts.*, 1983, 24(15), 1589–1592.

Hansske, F. et al., "2' and 3'-Ketonucleosides and their *Arabino* and *Xylo* Reduction Products", *Tetrahedron*, 1984, 40, 125–135.

Hausen, P. et al., "Ribonuclease H: An Enzyme Degrading the RNA Moiety of DNA–RNA Hybrids," *Eur. J. Biochem.*, 1970, 14, 278–283.

Iribarren, A.M. et al., "Resistance to Degradation by Nucleases of (2'S)–2'–Deoxy–2'–C–methyloligonucleotides, Novel Potential Antisense Probes," *Antisense Res. and Develop.*, 1994, 4, 95–98.

Itaya, M., "Isolation and characterization of a second RNase H (RNase HII) of *Escherichia coli* K–12 encoded by the rnhB gene," *Proc. Natl. Acad. Sci. USA*, 1990, 87, 8587–8591.

Itaya et al., "Selective cloning of genes encoding RNase H from *Salmonella typhimurium, Saccharomyces cerevisiae* and *Escherichia coli rnh* mutant," *Mol. Gen. Genet.*, 1991, 227, 438–445.

Itaya, M. et al., "Molecular cloning of a ribonuclease H (RNase HI) gene from an extreme thermophile *Thermus thermophilus* HB8: a thermostable RNase H can functionally replace the *Escherichia coli* enzyme in vivo," *Nucleic Acids Res.*, 1991, 19(16), 4443–4449.

Iyer, R.P. et al., "The Automated Synthesis of Sulfur–Containing Oligodeoxyribonucleotides Using 3H–1,2–Benzodithiol–3–one 1,1–Dioxide as a Sulfur–Transfer Reagent", *J. Org. Chem.*, 1990, 55, 4693–4699.

Kabanov, A.V., "A new class of antivirals: antisense oligonucleotides combined with a hydrophobic substituent effectively inhibit influenza virus reproduction and synthesis of virus–specific proteins in MDCK cells", *FEBS Letts.*, 1990, 259, 327–330.

Kanaya, S. et al., "Expression, Purification, and Characterization of a Recombinant Ribonuclease H from *Thermus thermophilus* HB8," *J. Biol. Chem.*, 1992, 267(14), 10184–10192.

Kanaya et al., "Importance of the Positive Charge Cluster in *Escherichia coli* Ribonuclease HI for the Effective Binding of the Substrate," *J. Biol. Chem.*, 1991, 266(18), 11621–11627.

Kane, C.M., "Renaturase and Ribonuclease H: A Novel Mechanism That Influences Transcript Displacement by RNA Polymerase II in Vitro," *Biochemistry*, 1988, 27, 3187–3196.

Katayanagi et al., "Three–dimensional structure of ribonuclease H from *E. coli,*" *Nature*, 1990, 347, 306–309.

Katayanagi et al., "Crystal Structure of *Escherichia coli* RNase HI in Complex With $Mg^{2+}$ at 2.8 Å Resolution: Proof for a Single $Mg^{2+}$ Binding Site," *Proteins: Struct., Funct., Genet.*, 1993, 17, 337–346.

Kois, P. et al., "Synthesis and Some Properties of Modified Oligonucleotides. 2. Oligonucleotides Containing 2'-Deoxy-2'-Fluoro-B-D-Arabinofuranosyl Pyrimidine Nucleosides," *Nucleosides & Nucleotides*, 1993, 12(10), 1093–1109.

Kozak, M., "The Scanning Model for Translation: An Update," *J. Cell Biol.*, 1989, 108, 229–241.

Lane, A. N. et al., "NMR Assignments and Solution Conformation of the DNA–RNA Hybrid Duplex d(GTGAACT-T)–r(AAGUUCAC)," *Eur. J. Biochem.*, 1993, 215, 297–306.

Lesnik, E.A. et al., "Oligodeoxynucleotides Containing 2'-O-Modified Adenosine" Synthesis and Effects on Stability of DNA:RNA Duplexes, *Biochem.*, 1993, 32, 7832–7838.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Lima, W.F. et al., "Binding Affinity and Specificity of *Escherichia coli* Rnase H1: Impact on the Kinetics of Catalysts of Antisense Oligonucleotide–RNA Hybrids," *Biochemistry*, 1997, 36, 390–398.

Lima, W.F. et al., "The influence of Antisense Oligonucleotide–induced RNA Structure on *Escherichia coli* RNase H1 Activity," *J. Biol. Chem.*, 1997, 272(29), 18191–18199.

Lin, K.Y. et al., "A Cytosine Analogue Capable of Clamp-Like Binding to a Guanine in Helical Nucleic Acids," *J. Am. Chem. Soc.*, 1998, 120, 8531–8532.

Manoharan, M. et al., "Chemical Modification to Improve Uptake and Bioavailability of Antisense Oligonucleotides", *Annals NY Acad. Sciences*, 1992, 660, 306–309.

Manoharan, M. et al., "Lipidic Nucleic Acids", *Tetrahedron Letts.*, 1995, 36, 3651–3654.

Manoharan M. et al., "Oligonucleotide Conjugates: Alteration of the Pharmacokinetic Properties of Antisense Agents", *Nucleosides and Nucleotides*, 1995, 14, 969–973.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Cholic Acid–Oligonucliotides Conjugates for Antisense Applications", *Bioorganic Med. Chem. Letts.*, 1994, 4, 1053–1060.

Martin, P., "Ein neuer Zugang zu 2'–O–Alkylribonuclesiden und Eigenschaften deren Oligonucleotide", *Helvetica Chemica Acta*, 1995, 78, 486–504 (English abstract included).

Matsuda, A. et al., "Nucleosides and Nucleotides. 97. Synthesis of New Brand Spectrum Antineoplastic Nucleosides, 2'–Deoxy–2'–methylidenecytidine (DMDC) and Its Derivatives," *J. Med. Chem.*, 1991, 34, 812–819.

Mishra, R.K. et al., "Improved leishmanicidal effect of phosphorotioate antisense oligonucleotides by LDL–medicated delivery", *Biochim. Et Biophysica*, 1995, 1264, 229–237.

Monia, B.P. et al., "Evaluation of 2'–Modified Oligonucleotides Containing 2'–Deoxy Gaps as Antisense Inhibitors of Gene Expression", *J. Biol. Chem.*, 1993, 268, 14514–14522.

Monia, B.P. et al., "Sequence–specific Antitumor Activity of a Phosphorothioate Oligodeoxyribonucleotide Targeted to Human C–raf Kinase Supports an Antisense Mechanism of Action In Vivo," *Proc. Natl. Acad. Sci. USA*, 1996, 93, 15481–15483.

Nakamura et al., "How does Rnase H recognize a DNA·RNA hybrid?" *Proc. Natl. Acad. Sci. USA*, 1991, 88, 11535–11539.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Obika, S. et al., "Preparation and Properties of 2',5'–Linked Oligonucleotide Analogues Containing 3'–O,4'–C–Methyleneribonucleosides," *Bioorg. Med. Chem. Letts.*, 1999, 9, 515–518.

Ouchi, T. et al., "Synthesis and Antitumor Activity of Poly(Ehtylene Glycol)s Linked to 5'–Fluorouracil via a Urethane or Urea Bond", *Drug Des. & Disc.*, 1992, 9, 93–105.

Pardi et al., "Comparative Study of Ribonucleotide, Deoxyribonucleotide, and Hybrid Oligonucleotide Helices by Nuclear Magnetic Resonance," *Biochemistry*, 1981, 20, 3986–3996.

Polushin, N. N. et al., "Synthesis of Oligonucleotides Containing 2'–Azido–and 2'–Amino–2'–deoxyuridine Using Phosphotriester Chemistry," *Tetrahedron Letts.*, 1996, 37(19), 3227–3230.

Pon, R.T., "Solid Phase Supports for Oligonucleotide Synthesis", *Methods in Molecular Biology, vol. 20, Protocols for Oligonucleotides and Analogs*, Agrawal, S. (ed.), Humana Press, Totowa, NJ, 1993, Chapter 19, 465–496.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Resmini, M. et al., "38. Nucleosides: Efficient Synthesis of Arabinoguanosine Building Blocks," *Helvetica Chimica Acta*, 1994, 77, 429–434.

Resmini, M. et al., "9. Nucleotides: Synthesis of Arabinonucleoside Phosphoramidite Building Blocks," *Helvetica Chimica Acta*, 1993, 76, 158–167.

Resmini, M. et al., "Synthesis of an Arabinonucleic Acid (tANA)," *Bioorgan. & Med. Chem. Letts.*, 1994, 4(16), 1909–1912.

Roberts, D. D. et al., "Neighboring–Group Study in Solvolyses of Cyclopentyl and Cyclohexyl Tosylates," *J. Org. Chem.*, 1969, 34(8), 2415–2417.

Roberts, D. D. et al., "Neighboring Methoxy Group Effect in Solvolysis Reactions of Cyclopentyl and Cyclohexyl p–Toluenesulfonates," *J. Org. Chem.*, 1997, 62, 1857–1859.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Rong, Y. W. et al., "On the Molecular Weight and Subunit Composition of Calf Thymus Ribonuclease H1," *Biochemistry*, 1990, 29, 383–389.

Rosenthal, A. et al., "Nucleosides of Branched–Chain Nitromethyl, Cyanomethyl, and Aminomethyl Sugars," *Tetrahedron Letts.*, 1970, 48, 4233–4235.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi, Y.S. et al., "Concept, Discovery and Development of MMI Linkage: Story of a Novel Linkage for Antisense Constructs," *Nucleosides & Nucleotides*, 1997, 16(7–9), 907–916.

Schmit, C. et al., "The Effects of 2'–and 3'–Alkyl Substituents on Oligonucleotide Hybridization and Stability," *Bioorgan. & Med. Chem. Letts.*, 1994, 4(16), 1969–1974.

Seela, F. et al., "Palindromic Octa–and Dodecanucleotides Containing 2'–Deoxytubercidin: Synthesis, Hairpin Formation, and Recognition by the Endodeoxyribonuclease EcoRI", *Biochemistry*, 1987, 26, 2232–2238.

Shea, R.G. et al., "Synthesis, hybridization properties and antiviral activity of lipid–oligodeoxynucletide conjugates", *Nucl. Acids Res.*, 1990, 18, 3777–3783.

Stein, H. et al., "Enzyme from Calf Thymus Degrading the RNA Moiety of DNA–RNA Hybrids: Effect on DNA–Dependent RNA Polymerase," *Science*, 1969, 166, 393–395.

Suck, D. et al., "Structure of DNase I at 2.0 Å resolution suggests a mechanism for binding to and cutting DNA," *Nature*, 1986, 321, 620–625.

Svinarchuk, F.P. et al., "Inhibition of HIV proliferation in MT–4 cells by antisense oligonucleotide conjugated to lipophilic groups", *Biochimie*, 1993, 79, 49–54.

Swayze, E. E. et al., "The Synthesis of N,N'–O–Trisubstituted Hydroxylamines via a Mild Reductive Alkylation Procedure: An Improved Synthesis of the MMI Backbone," *Synlett*, 1997, 859–861.

Swayze, E. E. et al., "The Synthesis of the Sixteen Possible 2'–O–Methyl MMI Dimer Phosphoramidites: Building Blocks for the Synthesis of Novel Antisense Oligonucleotides," *Nucleosides & Nucleotides*, 1997, 16(7–9), 971–972.

Thomson, J. B. et al., "Synthesis and Properties of Diuridine Phosphate Analogues Containing Thio and Amino Modifications," *J. Org. Chem.*, 1996, 61, 6273–6281.

Tidd, D.M. et al., "Evaluationof N–ras oncogene antisense, sense, and nonsense sequence methylphosphonate oliconucleotide analogues", *Anti–Cancer Drug Design*, 1988, 3, 117–127.

Tidd, D.M. et al., "Partial protection of oncogene, anti–sense oligodeoxynucleotides againsst serum nuclease degradation using terminal methylphosphonate groups", *Br. J. Cancer*, 1989, 60, 343–350.

Wagner, D. et al., "Preparation and Synthesis Utility of Some Organotin Derivatives of Nucleosides", *J. Org. Chem.*, 1974, 39, 24–30.

Walder, R. et al., "Role of RNase H in hybrid–arrested translation by antisense oligonucleotides", *Proc. Natl. Acad. Sci.*, 1988, 85, 5011–5015.

Wintersberger, "Ribonucleases H of Retroviral and Cellular Origin," *Pharmac. Ther.*, 1990, 48, 259–280.

Wolfe, S., "The Gauche Effect. Some Stereochemical Consequences of Adjacent Electron Pairs and Polar Bonds," *Accounts of Chemical Research*, 1972, 5, 102–110.

Yang et al., "Structure of Ribonuclease H Phased at 2 Å Resolution by MAD Analysis of the Selenomethioyl Protein," *Science*, 1990, 249, 1398–1405.

Ausubel et al., *Current Protocols in Molecular Biology*, Wiley and Sons, New York, NY., 1988 and 1989.

Deutscher, M. P., *Guide to Protein Purification, Methods in Enzymology*, Academic Press, New York, NY, 182, 1990.

Sambrook, J. et al., *Molecular Cloning: A Laboratory Manual*, Cold Spring Harbor Laboratory Press, Plainview, 1989.

U.S. patent application Ser. No. 08/398,901, Cook et al., filed Mar. 6, 1995.

U.S. patent application Ser. No. 09/123,108, Manoharan et al., filed Jul. 27, 1998.

U.S. patent application Ser. No. 09/344,260, Manoharan, filed Jun. 25, 1999.

U.S. patent application Ser. No. 09/349,040, Manoharan et al., Jul. 7, 1999.

U.S. patent application Ser. No. 09/370,541, Manoharan et al., filed Aug. 9, 1999.

U.S. patent application Ser. No. 09/378,568, Manoharan et al., filed Aug. 19, 1999.

* cited by examiner

FIG. 6

```
Human      MSWLLFLAHRVALAALPCRRGSRGFGMFYAVRRGRKTGVFLTWNECRAQVDRFPAARFKKFATEDEAWAFVRKSAS
Chicken    MLRWL-----VAL-LSHSCFVSKGGGMFYAVRKGRQTGVYRTWAECQQQVNRFPSASFKKFATEKEAWAFVGAGPP
Yeast                  MARQGNFYAVRKGRETGIYNTWNECKNQVDGYGGAIYKKFNSYEQAKSFLGQPNT
Mouse EST                GICGLGMFYAVRRGRRPGVFLSWSECKAQVDRFPAARFKKFATEDEAWAFVRSSSS Human      PEVSEGHENQHGQESEAKPGKRLREPLDGDG-----------------------------------------
Chicken    DGQQSAPAETHGASAVAQENASHREEPETDV-----------------------------------------
Yeast      TSNYGSSTHAGGQVSKPHTTQKRVHRRNRPLHYSSLTSSSACSSLSSANTNTFYSVKSNVPNIESKIFNNWKDCQA
Mouse EST  PDGSKGQESAHEQKSQAKTSKRPREPL Human      -----------------------------HESAQPYAKHMKPSVEP-APPVSRDTFSYMGDFVVVYTDGCCSSNGRRKPRA
Chicken    -------LCCNACKRPYEQSTNEEHTVRRAKH---DEEQSTPVVSEAKFSYMGEFAVVYTDGCCSGNGRNRARA
Yeast      YVKHKRGITFKKFEDQLAAENFISGMSAHDY-KLMNISKESFESKYKLSSNTMYNKSMNVYCDGSSFGNGTSSSRA
E.coli                                                      MLKQVEIFTDGSCLGNPGPGGYG
Mouse EST                                                   VVVYTDGCCSSNGRKRARA Human      GIGVYWGPGHPLNVGI-RLPGRQTNQRAEIHAACKAIEQAKTQNIN------KLVLYTDSMFTINGITNWVQGWKKN
Chicken    GIGVYWGPGHPLNISE-RLPGRQTNQRAEIHAACKAIEQAKSQNIK------KLIIYTDSKFTINGITSWVENWKTN
Yeast      GYGAYFEGAPEENISEPLLSGAQTNNRAEIEAVSEALKKIWEKLTNEKEKVNYQIKTDSEYVTKLLNDRYMTYDNK
E.coli     AILRYRGREKTFSAGY---TRTTNNRMELMAAIVALEALKEHC------EVILSTDSQYVRQGITQWIHNWKKR
Mouse EST  GIGVYWGPGHPLNVRI-RLPGRQTNQRAEIHAACKAVMQAKAQNIS------KLVLYTDSMFTINGITNWVQGWKKN Human      GWKTSAGKEVINKEDFVALERL----------TQGMDIQWMHVPGHSGFIGNEEADRLAREGA-KQSED
Chicken    GWRTSSGGSVINKEDFQKLDSL----------SKGIEIQWMHIPGHAGFQGNEEADRLAREGASKQKL
Yeast      KLEGLPNSDLIVPLVQRFVKVKKYYELNKECFKNNGKFQIEWVKGHDGDPGNEMADFLAKKGASRR
E.coli     GWKTADKKPVKNVDLWQRLDAA-----------LGQHQIKWEWVKGHAGHPENERCDELARAAAMNPTLEDTGYQVEV
Mouse EST  GWRTSTGKDVINKEDFMEIDEL----------TQGMDIQWMHIPGHSGFVGNEE
```

HUMAN RNASE H1 AND OLIGONUCLEOTIDE COMPOSITIONS THEREOF

FIELD OF THE INVENTION

The present invention relates to a human Type 2 RNase H which has now been cloned, expressed and purified to electrophoretic homogeneity. The present invention further relates to oligonucleotide compositions that may serve as substrates for human RNase H1 or human Type 2 RNase H.

BACKGROUND OF THE INVENTION

RNase H hydrolyzes RNA in RNA-DNA hybrids. This enzyme was first identified in calf thymus but has subsequently been described in a variety of organisms (Stein, H. and Hausen, P., Science, 1969, 166, 393–395; Hausen, P. and Stein, H., Eur. J. Biochem., 1970, 14, 278–283). RNase H activity appears to be ubiquitous in eukaryotes and bacteria (Itaya, M. and Kondo K. Nucleic Acids Res., 1991, 19, 4443–4449; Itaya et al., Mol. Gen. Genet., 1991 227, 438–445; Kanaya, S., and Itaya, M., J. Biol. Chem., 1992, 267, 10184–10192; Busen, W., J. Biol. Chem., 1980, 255, 9434–9443; Rong, Y. W. and Carl, P. L., 1990, Biochemistry 29, 383–389; Eder et al., Biochimie, 1993 75, 123–126). Although RNase Hs constitute a family of proteins of varying molecular weight, nucleolytic activity and substrate requirements appear to be similar for the various isotypes. For example, all RNase Hs studied to date function as endonucleases, exhibiting limited sequence specificity and requiring divalent cations (e.g., $Mg^{2+}$, $Mn^{2+}$) to produce cleavage products with 5' phosphate and 3' hydroxyl termini (Crouch, R. J., and Dirksen, M. L., Nuclease, Linn, S, M., & Roberts, R. J., Eds., Cold Spring Harbor Laboratory Press, Plainview, N.Y. 1982, 211–241).

In addition to playing a natural role in DNA replication, RNase H has also been shown to be capable of cleaving the RNA component of certain oligonucleotide-RNA duplexes. While many mechanisms have been proposed for oligonucleotide mediated destabilization of target RNAs, the primary mechanism by which antisense oligonucleotides are believed to cause a reduction in target RNA levels is through this RNase H action. Monia et al., J. Biol. Chem., 1993, 266:13, 14514–14522. In vitro assays have demonstrated that oligonucleotides that are not substrates for RNase H can inhibit protein translation (Blake et al., Biochemistry, 1985, 24, 6139–4145) and that oligonucleotides inhibit protein translation in rabbit reticulocyte extracts that exhibit low RNase H activity. However, more efficient inhibition was found in systems that supported RNase H activity (Walder, R. Y. and Walder, J. A., Proc. Nat'l Acad. Sci. USA, 1988, 85, 5011–25 5015; Gagnor et al., Nucleic Acid Res., 1987, 15, 10419–10436; Cazenave et al., Nucleic Acid Res., 1989, 17, 4255–4273; and Dash et al., Proc. Nat'l Acad. Sci. USA, 1987, 84, 7896–7900.

Oligonucleotides commonly described as "antisense oligonucleotides" comprise nucleotide sequences sufficient in identity and number to effect specific hybridization with a particular nucleic acid or the protein(s) it encodes is generally referred to as the "target." Oligonucleotides are generally designed to bind either directly to mRNA transcribed from, or to a selected DNA portion of, a preselected gene target, thereby modulating the amount of protein translated from the mRNA or the amount of mRNA transcribed from the gene, respectively. Antisense oligonucleotides may be used as research tools, diagnostic aids, and therapeutic agents.

"Targeting" an oligonucleotide to the associated nucleic acid, in the context of this invention, also refers to a multistep process which usually begins with the identification of the nucleic acid sequence whose function is to be modulated. This may be, for example, a cellular gene (or mRNA transcribed from the gene) whose expression is associated with a particular disorder or disease state, or a foreign nucleic acid from an infectious agent. The targeting process also includes determination of a site or sites within this gene for the oligonucleotide interaction to occur such that the desired effect, either detection or modulation of expression of the protein, will result.

RNase H1 from E.coli is the best-characterized member of the RNase H family. The 3-dimensional structure of E.coli RNase HI has been determined by x-ray crystallography, and the key amino acids involved in binding and catalysis have been identified by site-directed mutagenesis (Nakamura et al., Proc. Natl. Acad. Sci. USA, 1991, 88, 11535–11539; Katayanagi et al., Nature, 1990, 347, 306–309; Yang et al., Science, 1990, 249, 1398–1405; Kanaya et al., J. Biol. Chem., 1991, 266, 11621–11627). The enzyme has two distinct structural domains. The major domain consists of four α helices and one large β sheet composed of three antiparallel β strands. The $Mg^{2+}$ binding site is located on the β sheet and consists of three amino acids, Asp-10, Glu-48, and Gly-11 (Katayanagi et al., Proteins: Struct., Funct., Genet., 1993, 17, 337–346). This structural motif of the $Mg^{2+}$ binding site surrounded by β strands is similar to that in DNase I (Suck, D., and Oefner, C., Nature, 1986, 321, 620–625). The minor domain is believed to constitute the predominant binding region of the enzyme and is composed of an α helix terminating with a loop. The loop region is composed of a cluster of positively charged amino acids that are believed to bind electrostatistically to the minor groove of the DNA/RNA heteroduplex substrate. Although the conformation of the RNA/DNA substrate can vary, from A-form to B-form depending on the sequence composition, in general RNA/DNA heteroduplexes adopt an A-like geometry (Pardi et al., Biochemistry, 1981, 20, 3986–3996; Hall, K. B., and Mclaughlin, L. W., Biochemistry, 1991, 30, 10606–10613; Lane et al., Eur. J. Biochem., 1993, 215, 297–306). The entire binding interaction appears to comprise a single helical turn of the substrate duplex. Recently the binding characteristics, substrate requirements, cleavage products and effects of various chemical modifications of the substrates on the kinetic characteristics of E.coli RNase HI have been studied in more detail (Crooke, S. T. et al., Biochem. J., 1995, 312, 599–608; Lima, W. F. and Crooke, S. T., Biochemistry, 1997, 36, 390–398; Lima, W. F. et al., J. Biol. Chem., 1997, 272, 18191–18199; Tidd, D. M. and Worenius, H. M., Br. J. Cancer, 1989, 60, 343; Tidd, D. M. et al., Anti-Cancer Drug Des., 1988, 3, 117.

In addition to RNase HI, a second E.coli RNase H, RNase HII has been cloned and characterized (Itaya, M., Proc. Natl. Acad. Sci. USA, 1990, 87, 8587–8591). It is comprised of 213 amino acids while RNase HI is 155 amino acids long. E. coli RNase HIM displays only 17% homology with E.coli RNase HI. An RNase H cloned from S. typhimurium differed from E.coli RNase HI in only 11 positions and was 155 amino acids in length (Itaya, M. and Kondo K., Nucleic Acids Res., 1991, 19, 4443–4449; Itaya et al., Mol. Gen. Genet., 1991, 227, 438–445). An enzyme cloned from S. cerevisae was 30% homologous to E.coli RNase HI (Itaya, M. and Kondo K., Nucleic Acids Res., 1991, 19, 4443–4449; Itaya et al., Mol. Gen. Genet., 991, 227, 438–445). Thus, to date, no enzyme cloned from a species other than E. coli has displayed substantial homology to E.coli RNase HII.

Proteins that display RNase H activity have also been cloned and purified from a number of viruses, other bacteria and yeast (Wintersberger, *U. Pharmac. Ther.*, 1990, 48, 259–280). In many cases, proteins with RNase H activity appear to be fusion proteins in which RNase H is fused to the amino or carboxy end of another enzyme, often a DNA or RNA polymerase. The RNase H domain has been consistently found to be highly homologous to *E.coli* RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., *Eur. J. Biochem.*, 1977, 74, 203–208). RNase H Type 1 enzymes are reported to have molecular weights in the 68–90 kDa range, be activated by either $Mn^{2+}$ or $Mg^{2+}$ and be insensitive to sulfhydryl agents. In contrast, RNase H Type 2 enzymes have been reported to have molecular weights ranging from 31–45 kDa, to require $Mg^{2+}$ to be highly sensitive to sulfhydryl agents and to be inhibited by $Mn^{2+}$ (Busen, W., and Hausen, P., *Eur. J. Biochem.*, 1975, 52, 179–190; Kane, C. M., *Biochemistry*, 1988, 27, 3187–3196; Busen, W., *J. Biol. Chem.*, 1982, 257, 7106–7108.).

An enzyme with Type 2 RNase H characteristics has been purified to near homogeneity from human placenta (Frank et al., *Nucleic Acids Res.*, 1994, 22, 5247–5254). This protein has a molecular weight of approximately 33 kDa and is active in a pH range of 6.5–10, with a pH optimum of 8.5–9. The enzyme requires $Mg^{2+}$ and is inhibited by $Mn^{2+}$ and n-ethyl maleimide. The products of cleavage reactions have 3' hydroxyl and 5' phosphate termini.

Despite the substantial information about members of the RNase family and the cloning of a number of viral, prokaryotic and yeast genes with RNase H activity, until now, no mammalian RNase H had been cloned. This has hampered efforts to understand the structure of the enzyme(s), their distribution and the functions they may serve.

In the present invention, a cDNA of human RNase H with Type 2 characteristics and the protein expressed thereby are provided.

SUMMARY OF THE INVENTION

The present invention provides oligonucleotides that can serve as substrates for human RNase H1. These oligonucleotides are mixed sequence oligonucleotides comprising at least two portions wherein a first portion is capable of supporting human RNase H1 cleavage of a complementary target RNA and a further portion which is not capable of supporting such human RNase H1 cleavage.

The present invention provides a mixed sequence oligonucleotide comprising at least 12 nucleotides and having a 3' end and a 5' end, said oligonucleotide being divided into a first portion and a further portion, said first portion being capable of supporting cleavage of a complementary target RNA by human RNase H1 polypeptide, said further portion being incapable of supporting said RNase H cleavage;

wherein said first portion comprises at least 6 nucleotides and is positioned in said oligonucleotide such that at least one of said 6 nucleotides is 8 to 12 nucleotides from the 3' end of said oligonucleotide.

In a preferred embodiment the oligonucleotide comprises at least one CA nucleotide sequence. In another embodiment the first portion of the mixed sequence oligonucleotide of the present invention comprises nucleotides having a B-form conformational geometry. In a further embodiment each of the nucleotides of the first portion of the oligonucleotide are 2'-deoxyribonucleotides. In a still further embodiment each of the nucleotides of the first portion of the oligonucleotide is a 2'-F arabinonucleotide or a 2'-OH arabinonucleotide. In yet another embodiment the nucleotides of the first portion are joined together in a continuous sequence by phosphate, phosphorothioate, phosphorodithioate or boranophosphate linkages. In yet a further embodiment all of the nucleotides of the further portion of the oligonucleotide are joined together in a continuous sequence by 3'-5' phosphodiester, 2'-5' phosphodiester, phosphorothioate, Sp phosphorothioate, Rp phosphorothioate, phosphorodithioate, 3'-deoxy-3'-amino phosphoroamidate, 3'-methylenephosphonate, methylene(methylimino), dimethylhydrazino, amide 3, amide 4 or boranophosphate linkages.

Yet another object of the present invention is to provide methods for identifying agents which modulate activity and/or levels of human RNase H1. In accordance with this aspect, the polynucleotides and polypeptides of the present invention are useful for research, biological and clinical purposes. For example, the polynucleotides and polypeptides are useful in defining the interaction of human RNase H1 and antisense oligonucleotides and identifying means for enhancing this interaction so that antisense oligonucleotides are more effective at inhibiting their target mRNA.

Yet another object of the present invention is to provide a method of prognosticating efficacy of antisense therapy of a selected disease which comprises measuring the level or activity of human RNase H in a target cell of the antisense therapy. Similarly, oligonucleotides can be screened to identify those oligonucleotides which are effective antisense agents by measuring binding of the oligonucleotide to the human RNase H1.

BRIEF DESCRIPTION OF THE DRAWINGS

FIG. 6 provides the human Type 2 RNase H primary sequence (286 amino acids; SEQ ID NO: 1) and sequence comparisons with chicken (293 amino acids; SEQ ID NO: 2), yeast (348 amino acids; SEQ ID NO: 3) and *E. coli* RNase H1 (155 amino acids; SEQ ID NO: 4) as well as an EST deduced mouse RNase H homolog (GenBank accession no. AA389926 and AA518920; SEQ ID NO: 5). Boldface type indicates amino acid residues identical to human. "@" indicates the conserved amino acid residues implicated in *E. coli* RNase H1 $Mg^{2+}$ binding site and catalytic center (Asp-10, Gly-11, Glu-48 and Asp-70). "*" indicates the conserved residues implicated in *E. coli* RNases H1 for substrate binding.

DETAILED DESCRIPTION OF PREFERRED EMBODIMENTS

Figure 1:
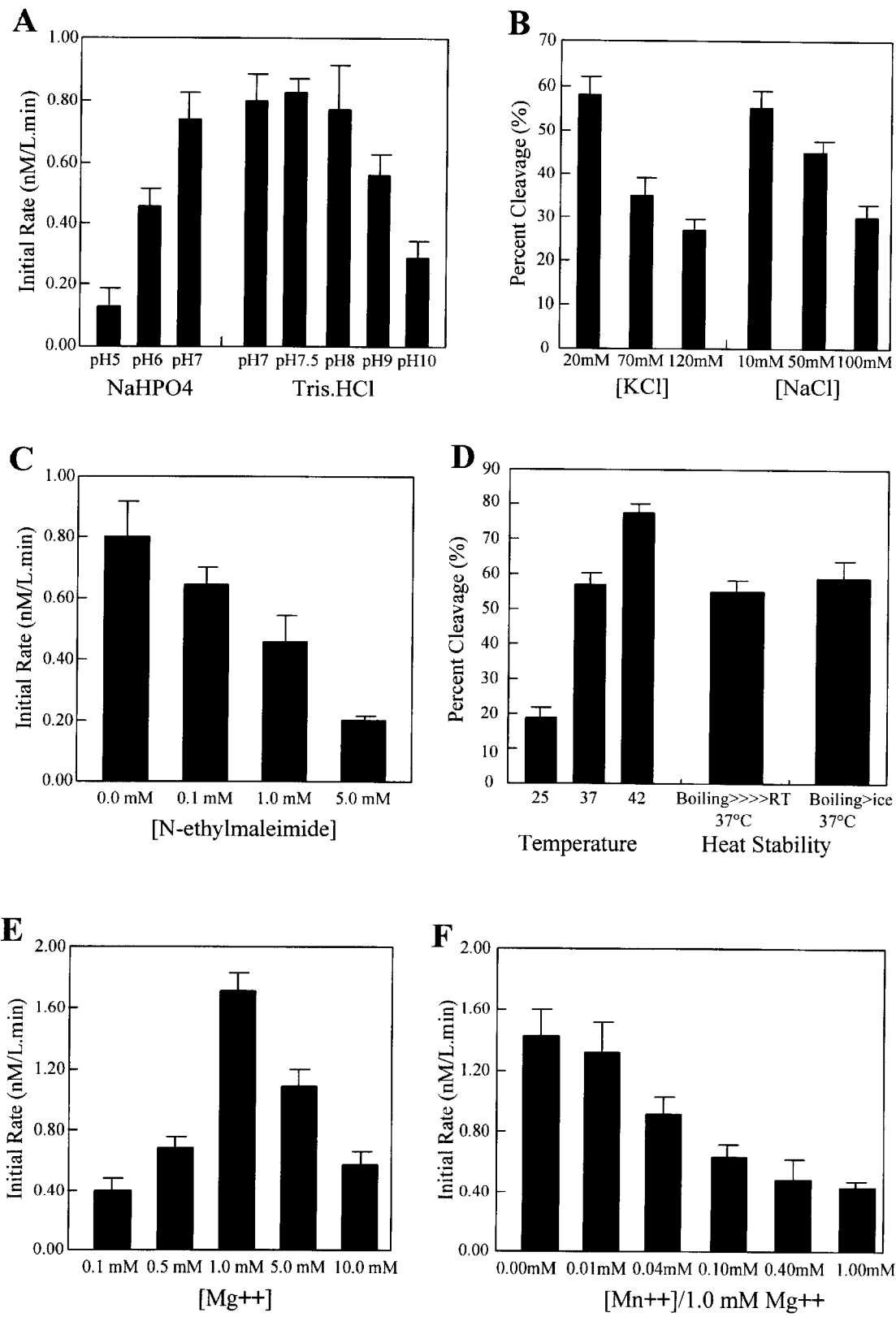
FIG. 1 shows the effects of conditions on human RNase H1 activity.

A Type 2 human RNase H has now been cloned and expressed. The enzyme encoded by this cDNA is inactive against single-stranded RNA, single-stranded DNA and double-stranded DNA. However, this enzyme cleaves the RNA in an NA/DNA duplex and cleaves the RNA in a duplex comprised of NA and a chimeric oligonucleotide with 2' methoxy flanks and 5-deoxynucleotide center gap. The rate of cleavage of the NA duplexed with this so-called "deoxy gapmer" was significantly slower than observed with the full RNA/DNA duplex. These properties are consistent with those reported for E.coli RNase H1 (Crooke et al., Biochem. J., 1995, 312, 599–608; Lima, W. F. and Crooke, S. T., Biochemistry, 1997, 36, 390–398). They are also consistent with the properties of a human Type 2 RNase H protein purified from placenta, as the molecular weight (32 kDa) is similar to that reported by Frank et al., Nucleic Acids Res., 1994, 22, 5247–5254) and the enzyme is inhibited by $Mn^{2+}$.

Thus, in accordance with one aspect of the present invention, there are provided isolated polynucleotides which encode human Type 2 RNase H polypeptides having the deduced amino acid sequence of FIG. 6. By "polynucleotides" it is meant to include any form of RNA or DNA such as mRNA or cDNA or genomic DNA, respectively, obtained by cloning or produced synthetically by well known chemical techniques. DNA may be double- or single-stranded. Single-stranded DNA may comprise the coding or sense strand or the non-coding or antisense strand.

Methods of isolating a polynucleotide of the present invention via cloning techniques are well known. For example, to obtain the cDNA contained in ATCC Deposit No. 98536, primers based on a search of the XREF database were used. An approximately 1 Kb cDNA corresponding to the carboxy terminal portion of the protein was cloned by 3' RACE. Seven positive clones were isolated by screening a liver cDNA library with this 1 Kb cDNA. The two longest clones were 1698 and 1168 base pairs. They share the same 5' untranslated region and protein coding sequence but differ in the length of the 3' UTR. A single reading frame encoding a 286 amino acid protein (calculated mass: 32029.04 Da) was identified (FIG. 6). The proposed initiation codon is in agreement with the mammalian translation initiation consensus sequence described by Kozak, M., J. Cell Biol., 1989, 108, 229–241, and is preceded by an in-frame stop codon. Efforts to clone cDNA's with longer 5' UTR's from both human liver and lymphocyte cDNA's by 5' PACE failed, indicating that the 1698-base-pair clone was full length.

In a preferred embodiment, the polynucleotide of the present invention comprises the nucleic acid sequence of the cDNA contained within ATCC Deposit No. 98536. The deposit of E. coli DH5α containing a BLUESCRIPT® plasmid containing a human Type 2 RNase H cDNA was made with the American Type Culture Collection, 12301 Park Lawn Drive, Rockville, Md. 20852, USA, on Sep. 4, 1997 and assigned ATCC Deposit No. 98536. The deposited material is a culture of E. coli DH5α containing a BLUE-SCRIPT® plasmid (Stratagene, La Jolla Calif.) that contains the full-length human Type 2 RNase H cDNA. The deposit has been made under the terms of the Budapest Treaty on the international recognition of the deposit of microorganisms for the purposes of patent procedure. The culture will be released to the public, irrevocably and without restriction to the public upon issuance of this patent. The sequence of the polynucleotide contained in the deposited material and the amino acid sequence of the polypeptide encoded thereby are controlling in the event of any conflict with the sequences provided herein. However, as will be obvious to those of skill in the art upon this disclosure, due to the degeneracy of the genetic code, polynucleotides of the present invention may comprise other nucleic acid sequences encoding the polypeptide of FIG. 6 and derivatives, variants or active fragments thereof.

Another aspect of the present invention relates to the polypeptides encoded by the polynucleotides of the present invention. In a preferred embodiment, a polypeptide of the present invention comprises the deduced amino acid sequence of human Type 2 RNase H provided in FIG. 6 as SEQ ID NO: 1. However, by "polypeptide" it is also meant to include fragments, derivatives and analogs of SEQ ID NO: 1 which retain essentially the same biological activity and/or function as human Type 2 RNase H. Alternatively, polypeptides of the present invention may retain their ability to bind to an antisense-RNA duplex even though they do not function as active RNase H enzymes in other capacities. In another embodiment, polypeptides of the present invention may retain nuclease activity but without specificity for the RNA portion of an RNA/DNA duplex. Polypeptides of the present invention include recombinant polypeptides, isolated natural polypeptides and synthetic polypeptides, and fragments thereof which retain one or more of the activities described above.

In a preferred embodiment, the polypeptide is prepared recombinantly, most preferably from the culture of E. coli of ATCC Deposit No. 98536. Recombinant human RNase H fused to histidine codons (his-tag; in the present embodiment six histidine codons were used) expressed in E.coli can be conveniently purified to electrophoretic homogeneity by chromatography with Ni-NTA followed by C4 reverse phase HPLC. The purified recombinant polypeptide of SEQ ID NO: 1 is highly homologous to E.coli RNase H, displaying nearly 34% amino acid identity with E.coli RNase H1. FIG. 6 compares the protein sequences deduced from human RNase H cDNA (SEQ ID NO: 1) with those of chicken (SEQ ID NO: 2), yeast (SEQ ID NO: 3) and E.coli RNase HI (Gene Bank accession no. 1786408; SEQ ID NO: 4), as well as an EST deduced mouse RNase H homolog (Gene Bank accession no. AA389926 and AA518920; SEQ ID NO: 5). The deduced amino acid sequence of human RNase H (SEQ ID NO: 1) displays strong homology with yeast (21.8% amino acid identity), chicken (59%), E.coli RNase HI (33.6%) and the mouse EST homolog (84.3%). They are all small proteins (<40 KDa) and their estimated pIs are all 8.7 and greater. Further, the amino acid residues in E.coli RNase HI thought to be involved in the $Mg^{2+}$ binding site, catalytic center and substrate binding region are completely conserved in the cloned human RNase H sequence (FIG. 6).

The human Type 2 RNase H of SEQ ID NO: 1 is expressed ubiquitously. Northern blot analysis demonstrated that the transcript was abundant in all tissues and cell lines except the MCR-5 line. Northern blot analysis of total RNA from human cell lines and Poly A containing RNA from human tissues using the 1.7 kb full length probe or a 332-nucleotide probe that contained the 5' UTR and coding region of human RNase H cDNA revealed two strongly positive bands with approximately 1.2 and 5.5 kb in length and two less intense bands approximately 1.7 and 4.0 kb in length in most cell lines and tissues. Analysis with the 332-nucleotide probe showed that the 5.5 kb band contained the 5' UTR and a portion of the coding region, which suggests that this band represents a pre-processed or partially processed transcript, or possibly an alternatively spliced transcript. Intermediate sized bands may represent processing intermediates. The 1.2 kb band represents the full length transcripts. The longer transcripts may be processing intermediates or alternatively spliced transcripts.

RNase H is expressed in most cell lines tested; only MRC5, a breast cancer cell line, displayed very low levels of RNase H. However, a variety of other malignant cell lines including those of bladder (T24), breast (T-47D, HS578T), lung (A549), prostate (LNCap, DU145), and myeloid lineage (HL-60), as well as normal endothelial cells (HUVEC), expressed RNase H. Further, all normal human tissues tested expressed RNase H. Again, larger transcripts were present as well as the 1.2 kb transcript that appears to be the mature mRNA for RNase H. Normalization based on G3PDH levels showed that expression was relatively consistent in all of the tissues tested.

The Southern blot analysis of EcoRI digested human and various mammalian vertebrate and yeast genomic DNAs probed with the 1.7 kb probe shows that four EcoRI digestion products of human genomic DNA (2.4, 4.6, 6.0, 8.0 Kb) hybridized with the 1.7 kb probe. The blot re-probed with a 430 nucleotide probe corresponding to the C-terminal portion of the protein showed only one 4.6 kbp EcoRI digestion product hybridized. These data indicate that there is only one gene copy for RNase H and that the size of the gene is more than 10 kb. Both the full length and the shorter probe strongly hybridized to one EcoRI digestion product of yeast genomic DNA (about 5 kb in size), indicating a high degree of conservation. These probes also hybridized to the digestion product from monkey, but none of the other tested mammalian genomic DNAs including the mouse which is highly homologous to the human RNase H sequence.

A recombinant human RNase H (his-tag fusion protein) polypeptide of the present invention was expressed in *E.coli* and purified by Ni-NTA agarose beads followed by C4 reverse phase column chromatography. A 36 kDa protein copurified with activity measured after renaturation. The presence of the his-tag was confirmed by Western blot analyses with an anti-penta-histidine antibody (Qiagen, Germany).

Renatured recombinant human RNase H displayed RNase H activity. Incubation of 10 ng purified renatured RNase H with RNA/DNA substrate for 2 hours resulted in cleavage of 40% of the substrate. The enzyme also cleaved RNA in an oligonucleotide/RNA duplex in which the oligonucleotide was a gapmer with a 5-deoxynucleotide gap, but at a much slower rate than the full RNA/DNA substrate. This is consistent with observations with *E.coli* RNase H1 (Lima, W. F. and Crooke, S. T., Biochemistry, 1997, 36, 390–398). It was inactive against single-stranded RNA or double-stranded RNA substrates and was inhibited by $Mn^{2+}$. The molecular weight (~36kDa) and inhibition by $Mn^{2+}$ indicate that the cloned enzyme is highly homologous to *E.coli* RNase HI and has properties consistent with those assigned to Type 2 human RNase H.

The sites of cleavage in the RNA in the full RNA/DNA substrate and the gapmer/RNA duplexes (in which the oligonucleotide gapmer had a 5-deoxynucleotide gap) resulting from the recombinant enzyme were determined. In the full RNA/DNA duplex, the principal site of cleavage was near the middle of the substrate, with evidence of less prominent cleavage sites 3' to the primary cleavage site. The primary cleavage site for the gapmer/RNA duplex was located across the nucleotide adjacent to the junction of the 2' methoxy wing and oligodeoxy nucleotide gap nearest the 3' end of the RNA. Thus, the enzyme resulted in a major cleavage site in the center of the RNA/DNA substrate and less prominent cleavages to the 3' side of the major cleavage site. The shift of its major cleavage site to the nucleotide in apposition to the DNA 2' methoxy junction of the 2' methoxy wing at the 5' end of the chimeric oligonucleotide is consistent with the observations for *E.coli* RNase HI (Crooke et al. (1995) Biochem. J. 312, 599–608; Lima, W. F. and Crooke, S. T. (1997) Biochemistry 36, 390–398). The fact that the enzyme cleaves at a single site in a 5-deoxy gap duplex indicates that the enzyme has a catalytic region of similar dimensions to that of *E.coli* RNase HI.

Accordingly, expression of large quantities of a purified human RNase H polypeptide of the present invention is useful in characterizing the activities of a mammalian form of this enzyme. In addition, the polynucleotides and polypeptides of the present invention provide a means for identifying agents which enhance the function of antisense oligonucleotides in human cells and tissues.

For example, a host cell can be genetically engineered to incorporate polynucleotides and express polypeptides of the present invention. Polynucleotides can be introduced into a host cell using any number of well known techniques such as infection, transduction, transfection or transformation. The polynucleotide can be introduced alone or in conjunction with a second polynucleotide encoding a selectable marker. In a preferred embodiment, the host comprises a mammalian cell. Such host cells can then be used not only for production of human Type 2 RNase H, but also to identify agents which increase or decrease levels of expression or activity of human Type 2 RNase H in the cell. In these assays, the host cell would be exposed to an agent suspected of altering levels of expression or activity of human Type 2 RNase in the cells. The level or activity of human Type 2 RNase in the cell would then be determined in the presence and absence of the agent. Assays to determine levels of protein in a cell are well known to those of skill in the art and include, but are not limited to, radioimmunoassays, competitive binding assays, Western blot analysis and enzyme linked immunosorbent assays (ELISAs). Methods of determining increase activity of the enzyme, and in particular increased cleavage of an antisense-mRNA duplex can be performed in accordance with the teachings of Example 5. Agents identified as inducers of the level or activity of this enzyme may be useful in enhancing the efficacy of antisense oligonucleotide therapies.

The present invention also relates to prognostic assays wherein levels of RNase in a cell type can be used in predicting the efficacy of antisense oligonucleotide therapy in specific target cells. High levels of RNase in a selected cell type are expected to correlate with higher efficacy as compared to lower amounts of RNase in a selected cell type which may result in poor cleavage of the mRNA upon binding with the antisense oligonucleotide. For example, the MRC5 breast cancer cell line displayed very low levels of RNase H as compared to other malignant cell types. Accordingly, in this cell type it may be desired to use antisense compounds which do not depend on RNase H activity for their efficacy.

Similarly, oligonucleotides can be screened to identify those which are effective antisense agents by contacting human Type 2 RNase H with an oligonucleotide and measuring binding of the oligonucleotide to the human Type 2 RNase H. Methods of determining binding of two molecules are well known in the art. For example, in one embodiment, the oligonucleotide can be radiolabeled and binding of the oligonucleotide to human Type 2 RNase H can be determined by autoradiography. Alternatively, fusion proteins of human Type 2 RNase H with glutathione-S-transferase or small peptide tags can be prepared and immobilized to a solid phase such as beads. Labeled or unlabeled oligonucleotides to be screened for binding to this enzyme can then be incubated with the solid phase. Oligonucleotides which bind to the enzyme immobilized to the solid phase can then be identified either by detection of bound label or by eluting specifically the bound oligonucleotide from the solid phase. Another method involves screening of oligonucleotide libraries for binding partners. Recombinant tagged or labeled human Type 2 RNase H is used to select oligonucleotides from the library which interact with the enzyme. Sequencing of the oligonucleotides leads to identification of those oligonucleotides which will be more effective as antisense agents.

The oligonucleotides of the present invention are formed from a plurality of nucleotides that are joined together via internucleotide linkages. While joined together as a unit in the oligonucleotide, the individual nucleotides of oligonucleotides are of several types. Each of these types contribute unique properties to the oligonucleotide. A first type of nucleotides are joined together in a continuous sequence that forms a first portion of the oligonucleotide. The remaining nucleotides are of at least one further type and are located in one or more remaining portions or locations within the oligonucleotide. Thus, the oligonucleotides of the invention include a nucleotide portion that contributes one set of attributes and a further portion (or portions) that contributes another set of attributes.

One attribute that is desirable is eliciting RNase H activity. To elicit RNase H activity, a portion of the oligonucleotides of the invention is selected to have B-form like conformational geometry. The nucleotides for this B-form portion are selected to specifically include ribopentofuranosyl and arabino-pentofuranosyl nucleotides. 2'-Deoxy-erythro-pentfuranosyl nucleotides also have B-form geometry and elicit RNase H activity. While not specifically excluded, if 2'-deoxy-erythro-pentfuranosyl nucleotides are included in the B-form portion of an oligonucleotide of the invention, such 2'-deoxy-erythro-pentfuranosyl nucleotides preferably does not constitute the totality of the nucleotides of that B-form portion of the oligonucleotide, but should be used in conjunction with ribonucleotides or an arabino nucleotides. As used herein, B-form geometry is inclusive of both C2'-endo and O4'-endo pucker, and the ribo and arabino nucleotides selected for inclusion in the oligonucleotide B-form portion are selected to be those nucleotides having C2'-endo conformation or those nucleotides having O4'-endo conformation. This is consistent with Berger, et. al., *Nucleic Acids Research*, 1998, 26, 2473–2480, who pointed out that in considering the furanose conformations in which nucleosides and nucleotides reside, B-form consideration should also be given to a O4'-endo pucker contribution.

A-form nucleotides are nucleotides that exhibit C3'-endo pucker, also known as north, or northern, pucker. In addition to the B-form nucleotides noted above, the A-form nucleotides can be C3'-endo pucker nucleotides or can be nucleotides that are located at the 3' terminus, at the 5' terminus, or at both the 3' and the 5' terminus of the oligonucleotide. Alternatively, A-form nucleotides can exist both in a C3'-endo pucker and be located at the ends, or termini, of the oligonucleotide. In selecting nucleotides that have C3'-endo pucker or in selecting nucleotides to reside at the 3' or 5' ends of the oligonucleotide, consideration is given to binding affinity and nuclease resistance properties that such nucleotides need to impart to the resulting the oligonucleotide.

Nucleotides selected to reside at the 3' or 5' termini of oligonucleotides of the invention are selected to impart nuclease resistance to the oligonucleotide. This nuclease resistance can also be achieved via several mechanisms, including modifications of the sugar portions of the nucleotide units of the oligonucleotides, modification of the internucleotide linkages or both modification of the sugar and the internucleotide linkage.

A particularly useful group of nucleotides for use in increasing nuclease resistance at the termini of oligonucleotides are those having 2'-O-alkylamino groups thereon. The amino groups of such nucleotides can be groups that are protonated at physiological pH. These include amines, monoalkyl substituted amines, dialkyl substituted amines and heterocyclic amines such as imidazole. Particularly useful are the lower alkyl amines including 2'-O-ethylamine and 2'-O-propylamine. Such O-alkylamines can also be included on the 3' position of the 3' terminus nucleotide. Thus the 3' terminus nucleotide could include both a 2' and a 3'-O-alkylamino substituent.

In selecting for nuclease resistance, it is important not to detract from binding affinity. Certain phosphorus based linkage have been shown to increase nuclease resistance. The above described phosphorothioate linkage increase nuclease resistance, however, it also causes loss of binding affinity. Thus, generally for use in this invention, if phosphorothioate internucleotide linkage are used, other modification will be made to nucleotide units that increase binding affinity to compensate for the decreased affinity contribute by the phosphorothioate linkages.

Other phosphorus based linkages having increase nuclease resistance that do not detract from binding affinity include 3'-methylene phosphonates and 3'-deoxy-3'-amino-phosphoroamidate linkages. A further class of linkages that contribute nuclease resistance but do not detract from binding affinity are non-phosphate in nature. Preferred among these are methylene(methylimino) linkages, dimethylhydraxino linkages, and amine 3 and amide 4 linkages as described (Freier and Altmann, *Nucleic Acid Research*, 1997, 25, 4429–4443).

There are a number of potential items to consider when designing oligonucleotides having improved binding affinities. It appears that one effective approach to constructing modified oligonucleotides with very high RNA binding affinity is the combination of two or more different types of modifications, each of which contributes favorably to various factors that might be important for binding affinity.

Freier and Altmann, *Nucleic Acids Research*, (1997) 25:4429–4443, recently published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and $T_m$. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Numerous backbone modifications were also investigated including backbones bearing phosphorus, backbones that did not bear a phosphorus atom, and backbones that were neutral.

Four general approaches might be used to improve hybridization of oligonucleotides to RNA targets. These include: preorganization of the sugars and phosphates of the oligodeoxynucleotide strand into conformations favorable for hybrid formation, improving stacking of nucleobases by the addition of polarizable groups to the heterocycle bases of the nucleotides of the oligonucleotide, increasing the number of H-bonds available for A-U pairing, and neutralization of backbone charge to facilitate removing undesirable repulsive interactions. We have found that by utilizing the first of these, preorganization of the sugars and phosphates of the oligodeoxynucleotide strand into conformations favorable for hybrid formation, to be a preferred method to achieve improve binding affinity. It can further be used in combination with the other three approaches.

Sugars in DNA:RNA hybrid duplexes frequently adopt a C3' endo conformation. Thus modifications that shift the conformational equilibrium of the sugar moieties in the single strand toward this conformation should preorganize the antisense strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

As used herein, the terms "substituent" and "substituent group" refers to groups that are attached to nucleosides of the invention. Substituent groups are preferably attached to selected sugar moieties but can alternatively be attached to selected heterocyclic base moieties. Selected nucleosides may have substituent groups at both the heterocyclic base and the sugar moiety, however a single substituent group is preferred at a sugar 2', 3' or 5'-positions with the 2'-position being particularly preferred.

Substituent groups include fluoro, O-alkyl, O-alkylamino, O-alkylalkoxy, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser No. 08/398,901, filed Mar. 6, 1995, entitled Oligomeric Compounds having Pyrimidine Nucleotide(s) with 2' and 5' Substitutions, hereby incorporated by reference in its entirety.

Additional substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further representative substituent groups include hydrogen, hydroxyl, $C_1$–$C_{20}$ alkyl, $C_2$–$C_{20}$ alkenyl, $C_2$–$C_{20}$ alkynyl, halogen, amino, thiol, keto, carboxyl, nitro, nitroso, nitrile, trifluoromethyl, trifluoromethoxy, O-alkyl, O-alkenyl, O-alkynyl, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or each substituent group has one of formula I or II:

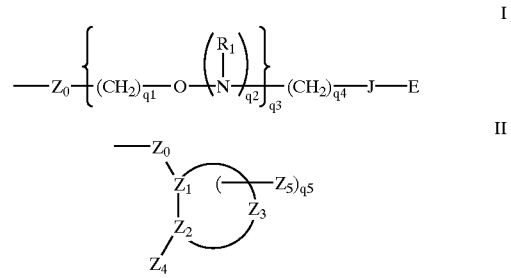

wherein:
$Z_0$ is O, S or NH;
J is a single bond, O or C(=O);
E is $C_1$–$C_{10}$ alkyl, N(R$_1$)(R$_2$), N(R$_1$)(R$_5$), N=C(R$_1$)(R$_2$), N=C(R$_1$)(R$_5$) or has one of formula III or IV;

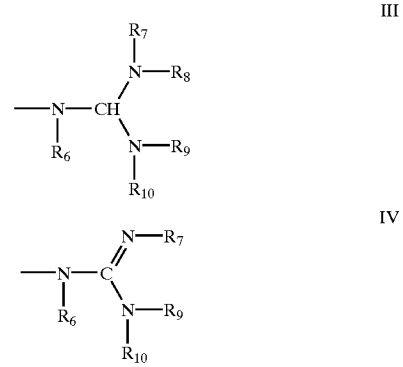

each R$_6$, R$_7$, R$_8$, R$_9$ and R$_{10}$ is, independently, hydrogen, C(O)R$_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_7$ and R$_8$, together form a phthalimido moiety with the nitrogen atom to which they are attached;

or optionally, R$_9$ and R$_{10}$, together form a phthalimido moiety with the nitrogen atom to which they are attached;

each R$_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—L,
  T is a bond or a linking moiety;
  L is a chemical functional group, a conjugate group or a solid support material;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;

each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, C(=NH)N(H)$R_5$, C(=O)N(H) $R_5$ or OC(=O)N(H)$R_5$;

$R_5$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and
provided that when $q_3$ is 0, $q_4$ is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred substituent groups include O[$(CH_2)_n$O]$_m$$CH_3$, O$(CH_2)_n$OCH$_3$, O$(CH_2)_n$NH$_2$, O$(CH_2)$CH$_3$, O$(CH_2)_n$ONH$_2$, and O$(CH_2)_n$ON[$(CH_2)_n$CH$_3$]$_2$, where n and m are from 1 to about 10.

Some preferred oligomeric compounds of the invention contain, at least one nucleoside having one of the following substituent groups: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a O$(CH_2)_2$ON$(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and a United States Patent Application entitled "Aminooxy-Functionalized Oligomers and Methods for Making Same," filed Aug. 9, 1999, hereby incorporated by reference in their entirety.

Other preferred modifications include 2'-methoxy (2'-O—CH$_3$), 2'-aminopropoxy (2'-OCH$_2$CH$_2$NH$_2$) and 2'-fluoro (2'-F). Similar modifications may also be made at other positions on nucleosides and oligomers, particularly the 3' position of the sugar on the 3' terminal nucleoside or in 2'-5' linked oligomers and the 5' position of 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040 entitled "Functionalized Oligomers," filed Jul. 7, 1999, hereby incorporated by reference in its entirety.

Representative acetamido substituent groups are disclosed in a United States Patent Application entitled "2'-O-Acetamido Modified Monomers and Oligomers," filed Aug. 19, 1999, hereby incorporated by reference in its entirety.

Representative dimethylaminoethyloxyethyl substituent groups are disclosed in an International Patent Application entitled "2'-O-Dimethylaminoethyloxyethyl-Modified Oligonucleotides," filed Aug. 6, 1999, hereby incorporated by reference in its entirety.

Several 2'-substituents confer a 3'-endo pucker to the sugar where they are incorporated. This pucker conformation further assists in increasing the Tm of the oligonucleotide with its target.

The high binding affinity resulting from 2' substitution has been partially attributed to the 2' substitution causing a C3' endo sugar pucker which in turn may give the oligomer a favorable A-form like geometry. This is a reasonable hypothesis since substitution at the 2' position by a variety of electronegative groups (such as fluoro and O-alkyl chains) has been demonstrated to cause C3' endo sugar puckering (De Mesmaeker et al., *Acc. Chem. Res.*, 1995, 28, 366–374; Lesnik et al., *Biochemistry*, 1993, 32, 7832–7838).

In addition, for 2'-substituents containing an ethylene glycol motif, a gauche interaction between the oxygen atoms around the O—C—C—O torsion of the side chain may have a stabilizing effect on the duplex (Freier et al., *Nucleic Acids*

Research, (1997) 25:4429–4442). Such gauche interactions have been observed experimentally for a number of years (Wolfe et al., *Acc. Chem. Res.*, 1972, 5, 102; Abe et al., *J. Am. Chem. Soc.*, 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

To better understand the higher RNA affinity of 2'-O-methoxyethyl substituted RNA and to examine the conformational properties of the 2'-O-methoxyethyl substituent, a self-complementary dodecamer oligonucleotide 2'-O-MOE r(CGCGAAUUCGCG) (SEQ ID NO: 13) SEQ ID NO: 1 was synthesized, crystallized and its structure at a resolution of 1.7 Ångstrom was determined. The crystallization conditions used were 2 mM oligonucleotide, 50 mM Na Hepes pH 6.2–7.5, 10.50 MM $MgCl_2$, 15% PEG 400. The crystal data showed: space group C2, cell constants a=41.2 Å, b=34.4 Å, c=46.6 Å, β=92.4°. The resolution was 1.7 Å at −170° C. The current R=factor was 20% ($R_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'—B' bond, as depicted in Structure II below, of the ethylene glycol linker has a gauche conformation. For 2'-O-MOE, A' and B' of Structure II below are methylene moieties of the ethyl portion of the MOE and R' is the methoxy portion.

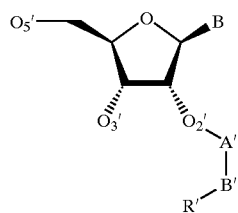

II

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. $g^+$ or $g^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other antisense modifications.

In extending the crystallographic structure studies, molecular modeling experiments were performed to study further enhanced binding affinity of oligonucleotides having 2'-O-modifications of the invention. The computer simulations were conducted on compounds of SEQ ID NO: 1, above, having 2'-O-modifications of the invention located at each of the nucleoside of the oligonucleotide. The simulations were performed with the oligonucleotide in aqueous solution using the AMBER force field method (Cornell et al., *J. Am. Chem. Soc.*, 1995, 117, 5179–5197) (modeling software package from UCSF, San Francisco, Calif.). The calculations were performed on an Indigo2 SGI machine (Silicon Graphics, Mountain View, Calif.).

Further 2'-O-modifications of the inventions include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

The ring structure can be further modified with a group useful for modifying the hydrophilic and hydrophobic properties of the ring to which it is attached and thus the properties of an oligonucleotide that includes the 2'-O-modifications of the invention. Further groups can be selected as groups capable of assuming a charged structure, e.g. an amine. This is particularly useful in modifying the overall charge of an oligonucleotide that includes a 2'-O-modifications of the invention. When an oligonucleotide is linked by charged phosphate groups, e.g. phosphorothioate or phosphodiester linkages, location of a counter ion on the 2'-O-modification, e.g. an amine functionality, locally naturalizes the charge in the local environment of the nucleotide bearing the 2'-O-modification. Such neutralization of charge will modulate uptake, cell localization and other pharmacokinetic and pharmacodynamic effects of the oligonucleotide.

Preferred ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly preferred 2'-O-substituent groups of the invention are listed below including an abbreviation for each:

2'-O-(trans 2-methoxy cyclohexyl)—2'-O-(TMCHL)
2'-O-(trans 2-methoxy cyclopentyl)—2'-O-(TMCPL)
2'-O-(trans 2-ureido cyclohexyl)—2'-O-(TUCHL)
2'-O-(trans 2-methoxyphenyl)—2'-O-(2MP)

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-O-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Preferred for use as the B-form nucleotides for eliciting RNase H are ribonucleotides having 2'-deoxy-2'-S-methyl, 2'-deoxy-2'-methyl, 2'-deoxy-2'-amino, 2'-deoxy-2'-mono or dialkyl substituted amino, 2'-deoxy-2'-fluoromethyl, 2'-deoxy-2'-difluoromethyl, 2'-deoxy-2'-trifluoromethyl, 2'-deoxy-2'-methylene, 2'-deoxy-2'-fluoromethylene, 2'-deoxy-2'-difluoromethylene, 2'-deoxy-2'-ethyl, 2'-deoxy-2'-ethylene and 2'-deoxy-2'-acetylene. These nucleotides can alternately be described as 2'-$SCH_3$ ribonucleotide, 2'-$CH_3$ ribonucleotide, 2'-$NH_2$ ribonucleotide 2'-$NH(C_1$–$C_2$ alkyl) ribonucleotide, 2'-$N(C_1$–$C_2$ alkyl)$_2$ ribonucleotide, 2'-$CH_2F$ ribonucleotide, 2'-$CHF_2$ ribonucleotide, 2'-$CF_3$ ribonucleotide, 2'=$CH_2$ ribonucleotide, 2'=CHF ribonucleotide, 2'=$CF_2$ ribonucleotide, 2'-$C_2H_5$ ribonucleotide, 2'-CH=$CH_2$ ribonucleotide, 2'-C≡CH ribonucleotide. A further useful ribonucleotide is one having a ring located on the ribose ring in a cage-like structure including 3',O,4'-C-methyleneribonucleotides. Such cage-like structures will physically fix the ribose ring in the desired conformation.

Additionally, preferred for use as the B-form nucleotides for eliciting RNase H are arabino nucleotides having 2'-deoxy-2'-cyano, 2'-deoxy-2'-fluoro, 2'-deoxy-2'-chloro, 2'-deoxy-2'-bromo, 2'-deoxy-2'-azido, 2'-methoxy and the unmodified arabino nucleotide (that includes a 2'-OH projecting upwards towards the base of the nucleotide). These arabino nucleotides can alternately be described as 2'-CN arabino nucleotide, 2'-F arabino nucleotide, 2'-Cl arabino nucleotide, 2'-Br arabino nucleotide, 2'-$N_3$ arabino nucleotide, 2'-O—$CH_3$ arabino nucleotide and arabino nucleotide.

Such nucleotides are linked together via phosphorothioate, phosphorodithioate, boranophosphate or phosphodiester linkages, particularly preferred is the phosphorothioate linkage.

Illustrative of the B-form nucleotides for use in the invention is a 2'-S-methyl (2'-SMe) nucleotide that resides in C2' endo conformation. It can be compared to 2'-O-methyl (2'-OMe) nucleotides that resides in a C3' endo conformation. Particularly suitable for use in comparing these two nucleotides are molecular dynamic investigations using a SGI [Silicon Graphics, Mountain View, Calif.] computer and the AMBER [UCSF, San Francisco, Calif.] modeling software package for computer simulations.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O- and 2'-S-methylguanosine, along with normal deoxyguanosine and riboguanosine, starting from both C2'-endo and C3'-endo conformations using ab initio quantum mechanical calculations. All the structures were fully optimized at HF/6-31G* level and single point energies with electron-correlation were obtained at the MP2/6-31G*//HF/6-31G* level. As shown in Table 1, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6-31G*//

HF/6-31G* values which also predict the same difference in energy. The opposite trend is noted for riboguanosine. At the HF/6-31G* and MP2/6-31G*//HF/6-31G* levels, the C3'-endo form of riboguanosine is shown to be about 0.65 and 1.41 kcal/mol more stable than the C2' endo form, respectively.

TABLE 1

Relative energies* of the C3'-endo and C2'-endo conformations of representative nucleosides.

|  | HF/6-31G | MP2/6-31-G | CONTINUUM MODEL | AMBER |
| --- | --- | --- | --- | --- |
| dG | 0.60 | 0.56 | 0.88 | 0.65 |
| rG | −0.65 | −1.41 | −0.28 | −2.09 |
| 2'-O—MeG | −0.89 | −1.79 | −0.36 | −0.86 |
| 2'-S—MeG | 2.55 | 1.41 | 3.16 | 2.43 |

*energies are in kcal/mol relative to the C2'-endo conformation

Table 1 also includes the relative energies of 2'-O-methylguanosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6-31G* and MP2/6-31G*//HF/6-31G* levels. In contrast, the 2'-S-methyl group reverses the trend. The C2'-endo conformation is favored by about 2.6 kcal/mol at the HF/6-31G* level, while the same difference is reduced to 1.41 kcal/mol at the MP2/6-31G*//HF/6-31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 1 indicate that the calculated relative energies of these nucleosides compare qualitatively well with the ab initio calculations.

Additional calculations were also performed to gauge the effect of solvation on the relative stability of nucleoside conformations. The estimated solvation effect using HF/6-31G* geometries confirms that the relative energetic preference of the four nucleosides in the gas-phase is maintained in the aqueous phase as well (Table 1). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker [Fraser, A., Wheeler, P., Cook, P. D. and Sanghvi, Y. S., *J. Heterocycl. Chem.*, 1993, 30, 1277–1287]. It was observed that the 2'-S-methyl substitution in deoxynucleoside confers more conformational rigidity to the sugar conformation when compared with deoxyribonucleosides.

Structural features of DNA:RNA, OMe_DNA:RNA and SMe_DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe_DNA:RNA is approximately 1.2 Å from the starting A-form conformation; while the SMe_DNA:RNA shows a slightly higher deviation (approximately 1.8 Å) from the starting hybrid conformation. The SMe_DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe_DNA and SMe_DNA strands, with the former adopting C3'-endo, and the latter, C1'-exo/C2'-endo conformations.

An analysis of the helicoidal parameters for all three hybrid structures has also been performed to further characterize the duplex conformation. Three of the more important axis-basepair parameters that distinguish the different forms of the duplexes, X-displacement, propeller twist, and inclination, are reported in Table 2. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA: RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe_DNA, DNA, and SMe_DNA strands, respectively. All RNA complements adopt an X angle close to −160°. In addition, "crankshaft" transitions were also noted in the backbone torsions of the central UpU steps of the RNA strand in the SMe_DNA:RNA and DNA;RNA hybrids. Such transitions suggest some local conformational changes may occur to relieve a less favorable global conformation. Taken overall, the results indicate the amount of A-character decreases as OMe_DNA:RNA>DNA:RNA>SMe_DNA:RNA, with the latter two adopting more intermediate conformations when compared to A- and B-form geometries.

TABLE 2

Average helical parameters derived from
the last 500 ps of simulation time.
(canonical A-and B-form values are given for comparison)

| Helicoidal Parameter | B-DNA (x-ray) | B-DNA (fiber) | A-DNA (fiber) | DNA:RNA | OMe_DNA: RNA | SMe_DNA: RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π_interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 3. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

TABLE 3

Minor groove widths averaged
over the last 500 ps of simulation time

| Phosphate Distance | DNA: RNA | OMe_DNA: RNA | SMe_DNA: RNA | DNA: RNA (B-form) | RNA: RNA (A-form) |
|---|---|---|---|---|---|
| P5-P20 | 15.27 | 16.82 | 13.73 | 14.19 | 17.32 |
| P6-P19 | 15.52 | 16.79 | 15.73 | 12.66 | 17.12 |
| P7-P18 | 15.19 | 16.40 | 14.08 | 11.10 | 16.60 |
| P8-P17 | 15.07 | 16.12 | 14.00 | 10.98 | 16.14 |
| P9-P16 | 15.29 | 16.25 | 14.98 | 11.65 | 16.93 |
| P10-P15 | 15.37 | 16.57 | 13.92 | 14.05 | 17.69 |

In addition to the modifications described above, the nucleotides of the oligonucleotides of the invention can have a variety of other modification so long as these other modifications do not significantly detract from the properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at their 2' position, sugars having substituent groups at their 3' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as being structurally distinguishable from, yet functionally interchangeable with, naturally occurring or synthetic wild type oligonucleotides. All such oligonucleotides are comprehended by this invention so long as they function effectively to mimic the structure of a desired RNA or DNA strand. A class of representative base modifications include tricyclic cytosine analog, termed "G clamp" (Lin, et al., *J. Am. Chem. Soc.* 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The oligonucleotides of the invention also can include phenoxazine-substituted bases of the type disclosed by Flanagan, et al., *Nat. Biotechnol.* 1999, 17(1), 48–52.

Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Human RNase H1 displays a strong positional preference for cleavage, i.e., it cleaves between 8–12 nucleotides from the 5'-RNA:3'-DNA terminus of the duplex. Within the preferred cleavage site, the enzyme displays modest sequence preference with GU being a preferred dinucleotide. The minimum RNA:DNA duplex length that supports cleavage is 6-base pairs and the minimum RNA:DNA "gap size" that supports cleavage is 5-base pairs.

Properties of Purified Human RNase H1

The effects of various reaction conditions on the activity of Human RNase H1 were evaluated (FIG. 1). The optimal pH for the enzyme in both Tris HCl and phosphate buffers was 7.0–8.0. At pH's above pH8.0, enzyme activity was reduced. However, this could be due to instability of the substrate or effects on the enzyme, or both. To evaluate the potential contribution of changes in ionic strength to the activities observed at different pHs, two buffers, $NaHPO_4$ and Tris HCl were studied at pH 7.0 and gave the same enzyme activity even though the ionic strengths differed. Enzyme activity was inhibited by increasing ionic strength (FIG. 1B) and N-ethymaleamide (FIG. 1C). Enzyme activity increased as the temperature was raised from 25–42° C. (FIG. 1D). $Mg^{2+}$ stimulated enzyme activity with an optimal concentration of 1 mM. At higher concentrations, $Mg^{2+}$ was inhibitory (FIG. 1E). In the presence of 1 mM $Mg^{2+}$, $Mn^{2+}$ was inhibitory at all concentrations tested (FIG. 1F). The purified enzyme was quite stable and easily handled. In fact, the enzyme could be boiled and rapidly or slowly cooled without significant loss of activity (FIG. 1D). The initial rates of cleavage were determined for four duplex substrates studied simultaneously. The initial rate of cleavage for a phosphodiester DNA:RNA duplex was 1050±203 pmol $L^{-1}min^{-1}$ (Table 4A). The initial rate of cleavage of a phosphorothioate oligodeoxynucleotide duplex was approximately four-fold faster than that of the same duplex comprised of a phosphodiester antisense oligodeoxynucleotide (Table 4A). The initial rates for 17-mer and 20-mer substrates of different sequences were equal (Table 4B). However, when a 25-mer heteroduplex, containing the 17-mer sequence in the center of the duplex was digested (RNA 3), the rate was 50% faster. Interestingly, the Km of the enzyme for the 25 mer duplex was 40% lower than that for the 17 mer while the Vmax's for both duplexes were the same (see Table 6), suggesting that with the increase in length, a larger number of cleavage sites are available resulting in an increase in the number of productive binding interactions between the enzyme and substrate. As a result, a lower substrate concentration is required for the longer duplex to achieve a cleavage rate equal to that of the shorter duplex.

To better characterize the substrate specificity of Human RNase H1, duplexes in which the antisense oligonucleotide was modified in the 2'-position were studied. As previously reported for *E. coli* RNase H1, Human RNase H1 was unable to cleave substrates with 2'-modifications at the cleavage site of the antisense DNA strand or the sense RNA strand (Table 5). For example, the initial rate of cleavage of a duplex containing a phosphorothioate oligodeoxynucleotide and its complement was 3400 pmol $L^{-1}min^{-1}$ while that of its 2'-propoxy modified analog was undetectable (Table 5). A duplex comprised of a fully modified 2'-methoxy antisense strand also failed to support any cleavage (Table 5). The placement of 2'-methoxy modifications around a central region of oligodeoxynucleotides reduced the initial rate (Table 5). The smaller the central oligodeoxynucleotide "gap" the lower the initial rate. The smallest "gapmer" for which cleavage could be measured was a 5 deoxynucleotide gap. These data are highly consistent with observations we have previously reported for *E. coli* RNase H1 except that for the bacterial enzyme the minimum gap size was 4 deoxynucleotides.

The Km and Vmax of Human RNase H1 for three substrates are shown in Table 6. The Km valves for all three substrates were substantially lower than those of *E. coli* RNase H1 (Table 6). As previously reported for *E. coli* RNase H1, the Km for a phosphorothioate containing duplex was lower than that of a phosphodiester duplex. The Vmax of the human enzyme was 30 fold lower than that of the *E. coli* enzyme. The Vmax for the phosphorothioate containing substrate was less than the phosphodiester duplex. This is probably due to inhibition of the enzyme at higher concentrations by excess phosphorothioate single strand oligonucleotide as the initial rate of cleavage for a phosphorothioate containing duplex was, in fact, greater than the phosphodiester (Table 4).

Binding Affinity and Specificity

To evaluate the binding affinity of Human RNase H1, a competitive cleavage assay in which increasing concentrations of noncleavable substrates were added was used. Using this approach, the Ki is formally equivalent to the Kd for the competing substrates. Of the noncleavable substrates studied, Lineweaver-Burk analyses demonstrated that all inhibitors shown in Table. 7 were competitive (data not shown). A duplex containing a phosphodiester oligodeoxynucleotide hybridized to a phosphodiester 2'-methoxy oligonucleotide as the noncleavable substrate is considered most like DNA:RNA. Table 7 shows the results of these studies and compares them to previously reported results for the *E. coli* enzyme performed under similar conditions. Clearly, the affinity of the human enzyme for its DNA:RNA like substrate (DNA:2'-O-Me) was substantially greater than that of the *E. coli* enzyme, consistent with the differences observed in Km (Table 6).

*E. coli* RNase H1 displays approximately equal affinity for RNA:RNA, RNA:2'-O-Me and DNA:2'-O-Me duplexes (Table 7). The human enzyme displays similar binding properties, but is more able to discriminate between various duplexes. For example, the Kd for RNA:RNA was approximately 5 fold lower than the Kd for DNA:2'-O-Me. This is further demonstrated by the Kd for the RNA:2' F duplex. The Kd for the DNA:2'-F duplex was slightly greater than for the RNA:2'-F duplex and the RNA:RNA duplex, but clearly lower than for other duplexes. Thus, both enzymes can be considered double strand RNA binding proteins. However, Human RNase H1 is somewhat less specific for duplexes as compared to single.strand oligonucleotides than the E. coli enzyme. The enzyme bound to single strand RNA and DNA only 20 fold less well than an RNA:RNA duplex while the E. coli enzyme bound to single strand DNA nearly 600 fold less than to an RNA:RNA duplex (Table 7). The affinity of a single strand phosphorothioate oligodeoxynucleotide for both enzymes was significant relative to the affinity for the natural substrate and accounts for the inhibition of the enzymes by members of this class oligonucleotides. Remarkably, Human RNase H1 displayed the highest affinity for a single strand phosphorothioate oligodeoxynucleotide. Thus, this noncleavable substrate is a very effective inhibitor of the enzyme and excess phosphorothioate antisense drug in cells might be highly inhibitory.

Site and Sequence Preferences for Cleavage

Figure 2:
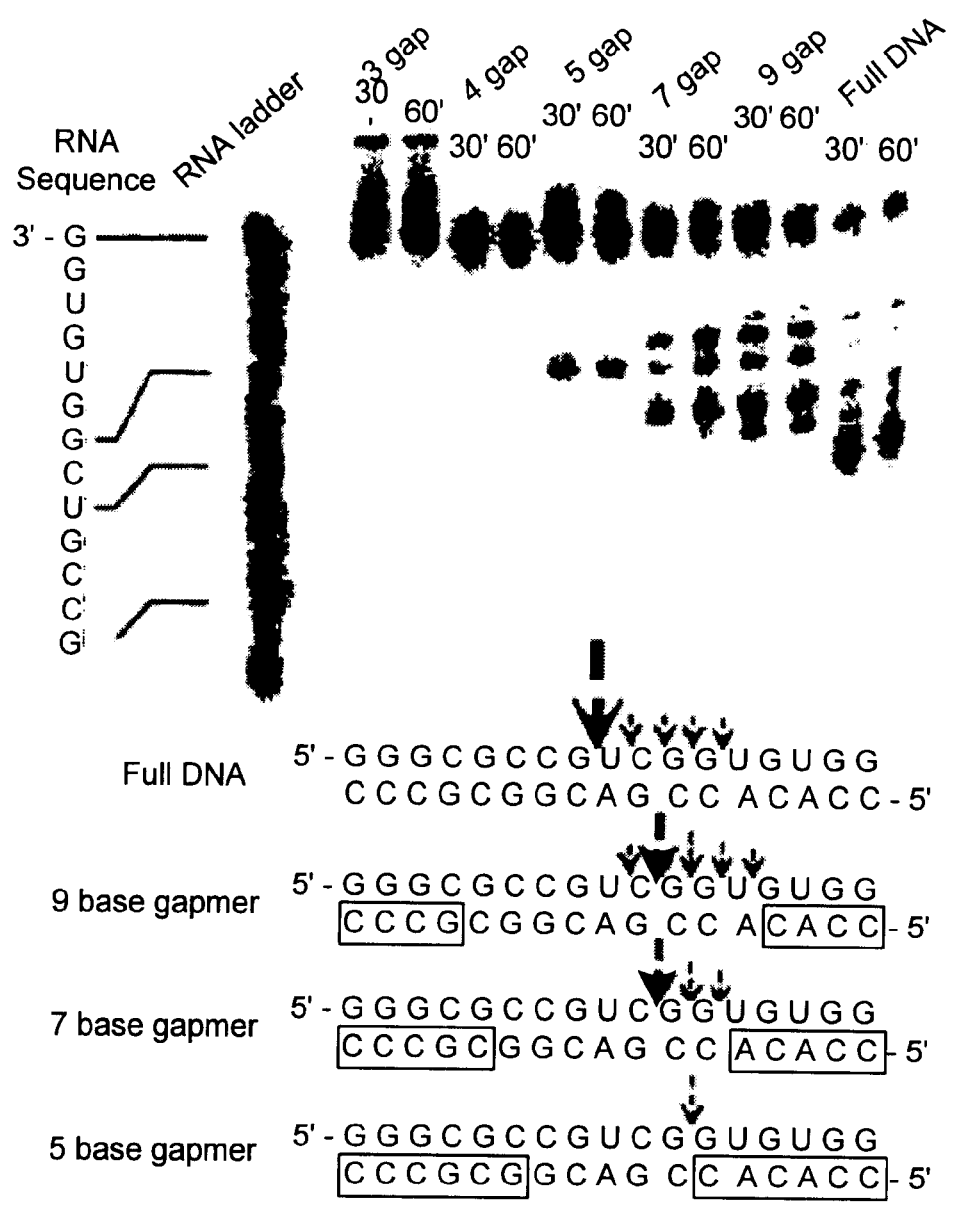
FIG. 2 shows a denaturing polyacrylamide gel analysis of human RNase H1 cleavage of a 17-mer RNA-DNA gapmer duplex.

FIG. 2 shows the cleavage pattern for RNA duplexed with its phosphorothioate oligodeoxynucleotide and the pattern for several gapmers. In the parent duplex, RNA cleavage occurred at a single major site with minor cleavage noted at several sites 3' to this major cleavage site that was 8 nucleotides from 5'-terminus of the RNA. Note that the preferred site occured at a GU dinucleotide. Cleavage of several "gapmers" occurred more slowly and the major cleavage site was at a different position from that of the parent duplex. Further, in contrast to the observations we have made for E. coli RNase H1, the major cleavage site in gapmers treated with Human RNase H1 did not occur at the nucleotide apposed to the nucleotide adjacent to the first 2' methoxy nucleotide in the wing hybridized to the 3' portion of the RNA.

Figure 3:
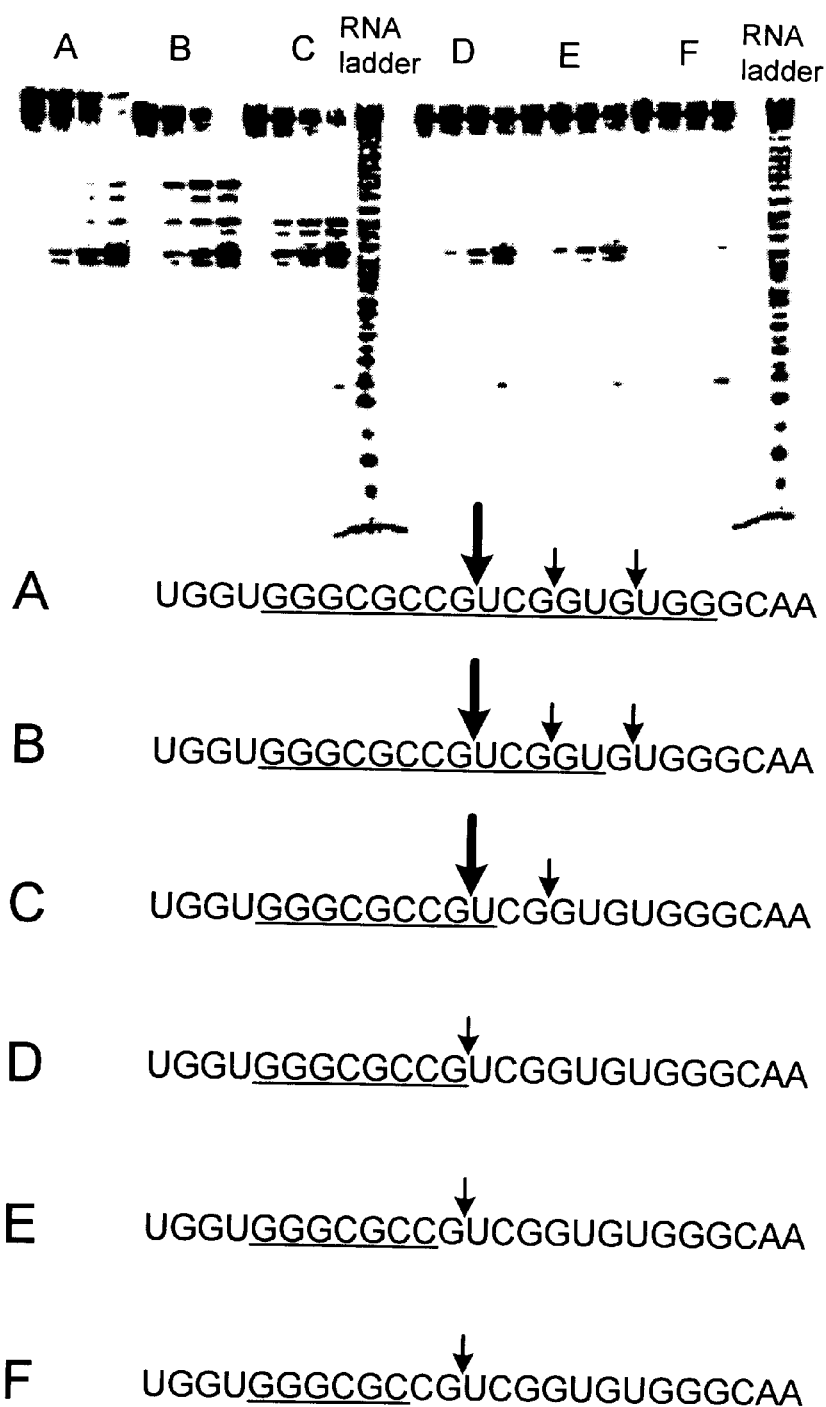
FIG. 3 shows analysis of human Rnase H1 cleavage of a 25-mer Ras RNA hybridized with phosphodiester oligodeoxynucleotides of different lengths.
Figure 4:
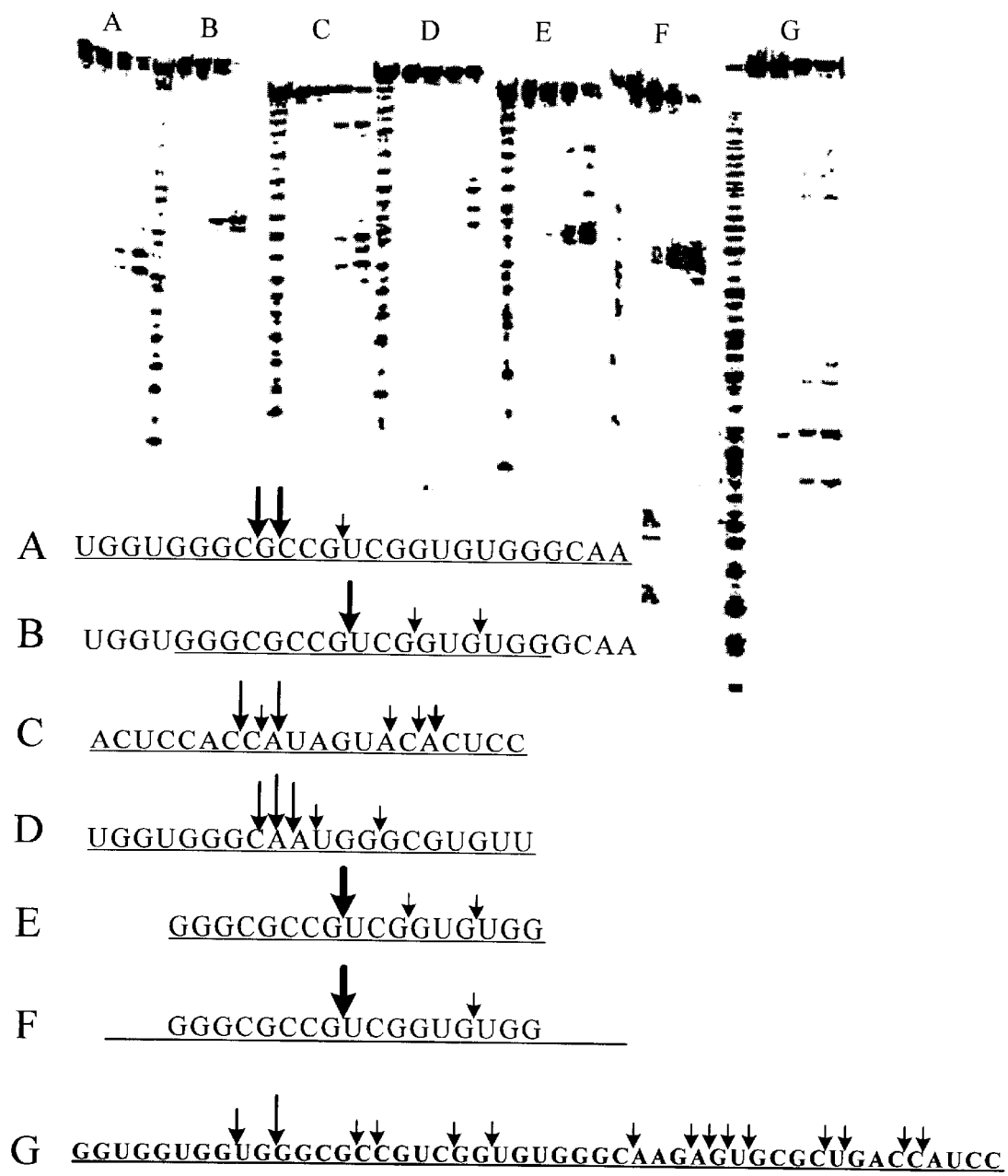
FIG. 4 shows analysis of human RNase H1 cleavage of RNA-DNA duplexes with different sequences, length and 3' or 5' overhangs. The sequence represented by G corresponds to SEQ ID NO: 33.

To further evaluate the site and sequence specificities of Human RNase H1, cleavage of substrates shown in FIG. 3 and FIG. 4 was studied. In FIG. 3, the sequence of the RNA is displayed below the sequencing gels and the length and position of the complementary phosphodiester oligodeoxynucleotide indicated by the solid line below the RNA sequence. This figure demonstrates several important properties of the enzyme. First, the main cleavage site was consistently observed 8–9 nucleotides from the 5'-RNA:3'-DNA terminus of the duplex irrespective of whether there were 5' or 3'-RNA single strand overhangs. Second, the enzyme, like E. coli RNase H1 was capable of cleaving single strand regions of RNA adjacent to the 3'-terminus of an RNA:DNA duplex. Third, the minimum duplex length that supported any cleavage was approximately 6 nucleotides. RNase protection assays were used to confirm that under conditions of the assay the shorter duplexes were fully hybridized, so the differences observed were not due to the failure to hybridize. To assure that the 6-nucleotide duplex was fully hybridized, the reactions were carried out at a 50:1 DNA:RNA ratio (data not shown). Fourth, the figure shows that for duplexes smaller than the nine base pairs, the smaller the duplex, the slower the cleavage rate. Fifth, the preferred cleavage site was located at a GU dinucleotide.

The site and sequence specificities are further explored in FIG. 4. That the enzyme displays little sequence preference is demonstrated by comparing the rates and sites of cleavage for duplexes A, C and D. In all cases, the preferred site of cleavage was 8–12 nucleotides from the 5'-RNA:3'-DNA terminus of the duplex irrespective of the sequence. Comparison of the cleavage pattern for duplexes A and B shows that cleavage occurred at the 8–12 nucleotide position even when there were RNA overhangs also as shown in FIG. 3. Cleavage of duplex F demonstrated that the site of cleavage was retained even if there were 5'- and 3'-DNA overhangs. In a longer substrate, duplex G, the main site of cleavage was still 8–12 nucleotides from the terminus of the duplex. However, minor cleavage sites were observed throughout the RNA suggesting that this substrate might support binding of more than one enzyme molecule per substrate, but that the preferred site was near the 5'-RNA:3'-DNA terminus. Finally, optimal cleavage seemed to occur when a GU dinucleotide was located 8–12 nucleotides from the 5'-RNA:3'-DNA terminus of the duplex.

Figure 5:
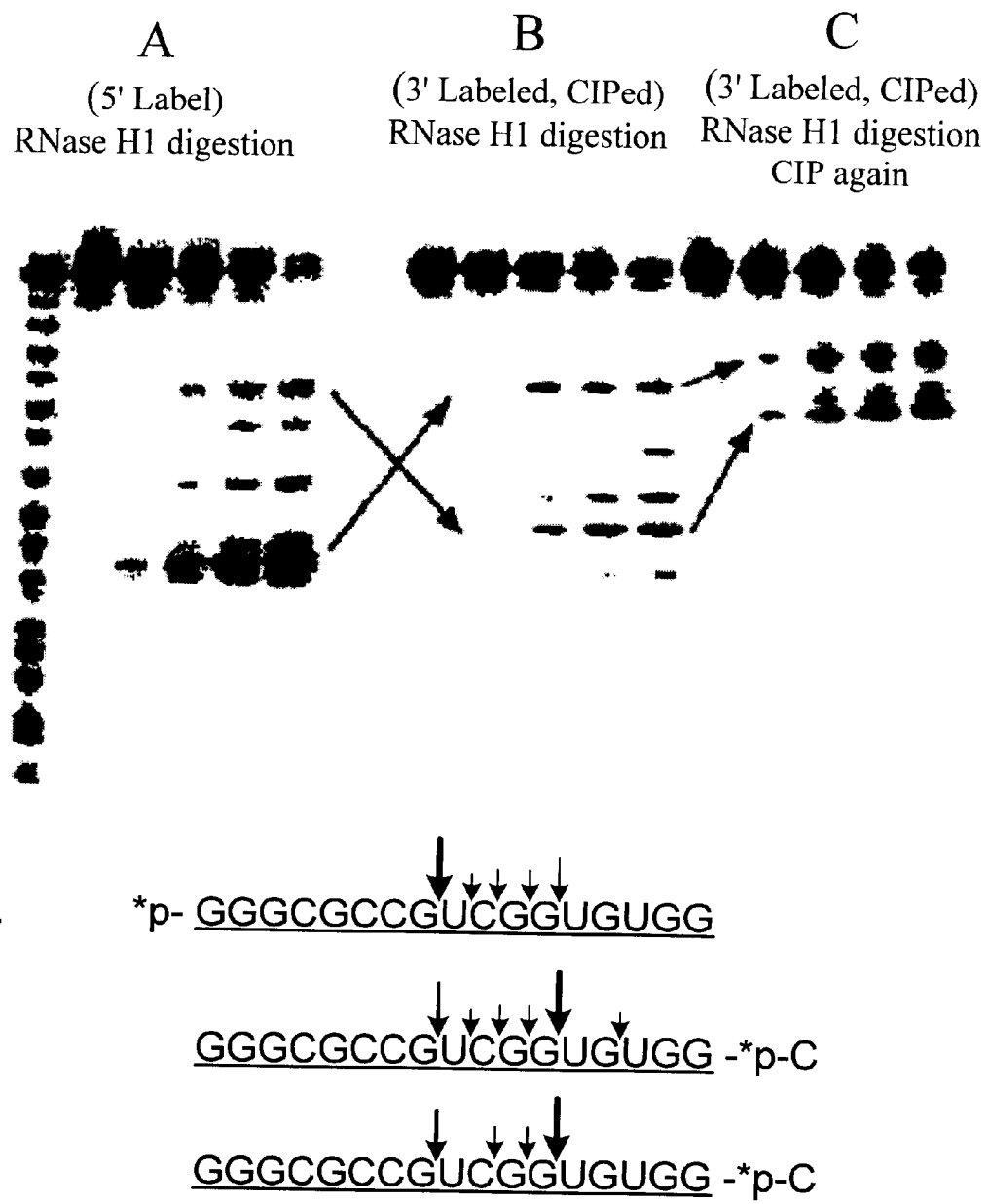
FIG. 5 shows product and processivity analysis of human RNase H1 cleavage on 17-mer Ras RNA-DNA duplexes.

To address both the mechanism of cleavage and processivity, the cleavage of 5'-labeled and 3'-labeled substrates was compared (FIG. 5). Lane C shows that CIP treatment prior to and after digestion with Human RNase H1 resulted in a shift in the mobility of the digested fragments suggesting that Human RNase H1 generates cleavage products with 5'-phosphates. Thus, it is similar to E. coli RNase H1 in this regard. A second intriguing observation is that the addition of pC to the 3'-end of the RNA caused a shift in the position of the preferred cleavage site (A vs B or C). The four cleavage sites in the center of the duplex observed with a 5'-phosphate labeled RNA were observed in 3' pC-labeled substrates. However, the main cleavage site shifted from base pair 8 to base pair 12. Interestingly, the sequence at both sites was GU. Thus, it is conceivable that the enzyme selects a position 8–12 nucleotide from the 5'-RNA:3'-DNA terminus, then cleaves at a preferred dinucleotide such as GU. Third, this figure considered along with the cleavage patterns shown in FIGS. 3 and 4 demonstrates that this enzyme displays minimal processivity in either the 5' or 3'-direction. In no time course experiment using any substrate have we observed a pattern that would be consistent with processivity. The possibility that the failure to observe processivity in FIGS. 3 and 4 was due to processivity in the 3' to 5'-direction is excluded by the results in FIG. 5. Again, this is significantly different from observations we have previously reported for E. coli RNase H1.

General Properties of Human RNase H1 Activity

The present invention also describes the properties of human RNase H1 that have been characterized. As the protein studied is a his-tag fusion and was denatured and refolded, it is possible that the activity of the enzyme in its native state might be greater than we have observed. However, basic properties are certainly likely to reflect the basic properties of the native enzyme. Numerous studies have shown that a his-tag does not interfere with protein folding and crystallization, kinetic and catalytic properties, or nucleic acid binding properties since it is very small (few amino acids) and its pK is near neutral. It is shown in the present invention that the his-tag fusion protein behaves like other RNase H's. It cleaved specifically the RNA strand in RNA:DNA duplexes, resulted in cleavage products with 5'-phosphate termini (FIG. 5) and was affected by divalent cations (FIG. 1). Optimal conditions for Human RNase H1 were similar to, but not identical to, E. coli RNase H1. For the human enzyme, he $Mg^{2+}$ optimum was 1 mM and 5 mM $Mg^{2+}$ was inhibitory. In the presence of $Mg^{2+}$, both enzymes were inhibited by $Mn^{2+}$. The human enzyme was inhibited by n-ethylmaleimide and was quite stable, easily handled and did not form multimeric structures (FIG. 1). The ease of handling, denaturation, refolding and stability in various conditions suggest that the Human RNase H1 was active as a monomer and has a relatively stable preferred conformation.

Studies on the structure and enzymatic activities of a number of mutants of *E. coli* RNase H1 have recently led to a hypothesis to explain the effects of divalent cations termed an activation/attenuation model. The effects of divalent cations on Human RNase H1 are complex and are consistent with the suggested activation/attenuation model. The amino acids proposed to be involved in both cation binding sites are conserved in Human RNase H1.

Positional and Sequence Preferences and Processivity

The site and sequence specificity of Human RNase H1 differ substantially from *E. coli* RNase H1. Although neither enzyme displays significant sequence specificity and FIGS. 2–5 this manuscript, the human enzyme displays remarkable site specificity. FIGS. 2–4 show that Human RNase H1 preferentially cleaved 8–12 nucleotides 3' from the 5'-RNA:3'-DNA terminus of a DNA:RNA duplex irrespective of whether there were 5' or 3'-RNA or DNA overhangs. The process by which a position is selected and then within that position on the duplex a particular dinucleotide is cleaved preferentially must be relatively complex and influenced by sequence. Clearly, the dinucleotide, GU, is a preferred sequence. In FIG. 3, for example, all the duplexes contained a GU sequence near the optimal position for the enzyme and in all cases the preferential cleavage site was GU. Additionally, in duplexes A and B a second GU was also cleaved, albeit at a very slow rate. The third site in duplexes A and B cleaved was a GG dinucleotide 7 base pairs from the 3'-RNA:5'-DNA terminus. Thus, the data suggest that the enzyme displays strong positional preference and within the appropriate site, slight preference for GU dinucleotides.

The strong positional preference exhibited by Human RNase H1 suggests that the enzyme fixes its position on the duplex via the 5'-RNA:3'-DNA terminus. Interestingly, the in-vitro cleavage pattern observed for the enzyme is compatible with its proposed in-vivo role, namely, the removal of RNA primers during DNA replication of the lagging strand. The average length of the RNA primer ranges from 7–14 nucleotides. Consequently, synthesis of the lagging strand results in chimeric sequences consisting of 7–14 ribonucleotides at the 5'-terminus with contiguous stretches of DNA extending in the 3' direction. The positional preference observed for Human RNase H1, (i.e., 8–12 residues from the 5'-terminus of the RNA), would suggest that cleavage of the chimeric lagging strand by RNase H1 would occur at or near the RNA:DNA junction. The removal of residual ribonucleatides following RNase H digestion has been shown to be performed by the endonuclease FEN1.

FIG. 4 provides additional insight into the positional and sequence preferences of the enzyme. When there was a GU dinucleotide present in the correct position in the duplex, it was cleaved preferentially. When a GU dinucleotide was absent, AU was cleaved as well as other dinucleotides. For duplex G both a GU and a GG dinucleotide were present within the preferred site, and in this case the GG dinucleotide was cleaved slightly more extensively than the GU dinucleotide. Clearly, additional duplexes of different sequences must be studied before definitive conclusions concerning the roles of various sequences within the preferred cleavage sites can be drawn.

In FIG. 5, the 3'-terminus of the RNA was labeled with $^{32}$pC. In this case the same four nucleotides were cleaved as when the RNA was 5' labeled (FIG. 5, panels B & C). However, the GU closer to the 3'-terminus of the RNA was cleaved at least as rapidly as the 5'-GU. Interestingly in studies on the partially purified enzyme, differences in the cleavage pattern were also observed when 5'-labeled substrates were compared to 3'-labeled substrates. A possible explanation for this observation is that the presence of a 3'-phosphate on an oligonucleotide substrate affects the scanning mechanism the enzyme uses to select preferred positions for cleavage.

In a duplex comprised of RNA annealed to a chimeric oligonucleotide with an oligodeoxynucleotide center flanked by 2'-modified nucleotide wings, the cleavage by Human RNase H1 was directed to the DNA:RNA portion of the duplex as was observed for *E. coli* RNase H1. However, within this region, the preferred sites of cleavage for the human enzyme differed from *E. coli* RNase H1. *E. coli* RNase H1 preferentially cleaved at the ribonucleotide apposed to first 2'-modified nucleotide in the wing of antisense oligonucleotide at the 3'-end of the RNA. In contrast, the human enzyme preferentially cleaved at sites more centered within the gap until the gap was reduced to 5 nucleotides. Further, the minimum gap size for the human enzyme was 5 nucleotides while that of *E. coli* RNase H1 was 4 nucleotides. These differences in behavior suggest differences in the structures of the enzymes and their interactions with substrate that will require additional study.

Although *E. coli* RNase H1 degrades the heteroduplex substrate in a predominantly distributive manner, the enzyme displays modest 5'-3'-processivity. In contrast, Human RNase H1 evidences no 5'-3' or 3'-5'-processivity suggesting that the human enzyme hydrolyzes the substrate in an exclusively distributive manner. The lack of processivity observed with the Human RNase H1 may be a function of the significantly tighter binding affinity (Table 7), thereby reducing the ability of the enzyme to move on the substrate. Alternatively, Human RNase H1 appears to fix its position on the substrate with respect to the 5'-RNA:3'-DNA terminus and this strong positional preference may preclude cleavage of the substrate in a processive manner. (FIG. 5). Thus, despite the fact that the enzymes are both metal-dependent endonucleases that result in cleavage products with 5'-phosphates (FIG. 5) and both can cleave single-strand 3'-RNA overhangs (FIG. 5), these enzymes display substantial differences.

*E. coli* RNase H1 has been suggested to exhibit "binding directionality" with respect to the RNA of the substrate such that the primary binding region of the enzyme is positioned several nucleotides 5' to the catalytic center. This results in cleavage sites being restricted from the 5'-RNA:3'-DNA end of a duplex, and cleavage sites occurring at the 3'-RNA:5'-DNA end of the duplex and in 3'-single-strand overhangs. The human enzyme behaves entirely analogously. Thus, we conclude that Human RNase H1 likely has the same binding directionality as the *E. coli* enzyme.

Substrate Binding

RNA:RNA duplexes have been shown to adopt an A-form conformation. Many 2'-modifications shift the sugar conformation into a 3'-endo pucker characteristic of RNA. Consequently, when hybridized to RNA, the resulting duplex is "A" form and this is manifested in a more stable duplex. 2'-F Oligonucleotides display duplex forming properties most like RNA, while 2'-methoxy oligonucleotides result in duplexes intermediate information between DNA:RNA and RNA:RNA duplexes.

The results shown in Table 7 demonstrate that like the *E. coli* enzyme, Human RNase H1 is a double strand RNA binding protein. Moreover, it displays some ability to discriminate between various A-form duplexes (Table 7). The observation that the Kd for an RNA:2'-F duplex is equal to that for an RNA:RNA dupex suggests that 2'-hydroxy group is not required for binding to the enzyme. Nevertheless, we cannot exclude the possibility that bulkier 2'-modifications, e.g. 2'-methoxy or 2'-propyl might sterically inhibit the binding of the enzyme as well as alter the A-form quality of the duplex. The human enzyme displays substantially greater affinity for all oligonucleotides than the *E. coli* enzyme and this is reflected in a lower Km for cleavable substrates (Tables 6 and 7). In addition, the tighter binding affinity observed for Human RNase H1 may be responsible for the 20-fold lower Vmax when compared to the *E. coli* enzyme. In this case, assuming that the *E. coli* and human enzymes exhibit similar catalytic rates (Kcat), then an increase in the binding affinity would result in a lower turnover rate and ultimately a lower Vmax.

The principal substrate binding site in *E. coli* RNase H1 is thought to be a cluster of lysines that are believed to bind to the phosphates of the substrates. The interaction of the binding surface of the enzyme and substrate is believed to occur within the minor groove. This region is highly conserved in the human enzyme. In addition, eukaryotic enzymes contain an extra N-terminal region of variable length containing an abundance of basic amino acids. This region is homologous with a double strand RNA binding motif and indeed in the *S. cerevasiae* RNase H has been shown to bind to double strand RNA. The N-terminal extension in Human RNase H1 is longer than that in the *S. cerevasiae* enzyme and appears to correspond to a more complete double strand RNA binding motif. Consequently, the enhanced binding of Human RNase H1 to various nucleic acids may be due to the presence of this additional binding site.

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocyclic ring" denotes a carbon-based ring system having one or more heteroatoms (i.e., non-carbon atoms). Preferred heterocyclic rings include, for example but not limited to imidazole, pyrrolidine, 1,3-dioxane, piperazine, morpholine rings. As used herein, the term "heterocyclic ring" also denotes a ring system having one or more double bonds, and one or more heteroatoms. Preferred heterocyclic rings include, for example but not limited to the pyrrolidino ring.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

As used herein, "human type 2 RNase H" and "human RNase H1" refer to the same human RNase H enzyme. Accordingly, these terms are meant to be used interchangeably.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The following nonlimiting examples are provided to further illustrate the present invention.

EXAMPLES

Example 1

5'-O-DMT-2'-O-(2-Methoxyethyl)-5-methyl Uridine and 5'-O-DMT-3'-O-(2-Methoxyethyl)5-methyl Uridine 2',3'-O-dibutylstannylene 5-methyl uridine (345 g) (prepared as per: Wagner et al., *J. Org. Chem.*, 1974, 39, 24) was alkylated with 2-methoxyethyl bromide (196 g) in the presence of tetrabutylammonium iodide (235 g) in DMF (3 L) at 70° C. to give a mixture of 2'-O- and 3'-O-(2-methoxyethyl)-5-methyl uridine (150 g) in nearly 1:1 ratio of isomers. The mixture was treated with DMT chloride (110 g, DMT-Cl) in pyridine (1 L) to give a mixture of the 5'-O-DMT-nucleosides. After the standard work-up the isomers were separated by silica gel column chromatography. The 2'-isomer eluted first, followed by the 3'-isomer.

Example 2

5'-O-DMT-3'-O-(2-Methoxyethyl)-5-methyl-uridine-2'-O-(2-cyanoethyl-N,N-diisopropyl) phosphoramidite 5'-O-DMT-3'-O-(2-methoxyethyl)-5-methyluridine (5 g, 0.008 mol) was dissolved in $CH_2Cl_2$ (30 mL) and to this solution, under argon, diisopropylaminotetrazolide (0.415 g) and 2-cyanoethoxy-N,N-diisopropyl phosphoramidite (3.9 mL) were added. The reaction was stirred overnight. The solvent was evaporated and the residue was applied to silica column and eluted with ethyl acetate to give 3.75 g title compound.

Example 3

5'-O-DMT-3'-O-(2-Methoxyethyl)-$N^4$-benzoyl-5-methyl-cytidine

5'-O-DMT-3'-O-(2-methoxyethyl)-5-methyl uridine (15 g) was treated with 150 mL anhydrous pyridine and 4.5 mL of acetic anhydride under argon and stirred overnight. Pyridine was evaporated and the residue was partitioned between 200 mL of saturated $NaHCO_3$ solution and 200 mL of ethylacetate. The organic layer was dried (anhydrous $MgSO_4$) and evaporated to give 16 g of 2'-acetoxy-5'-O-(DMT)-3'-O-(2-methoxyethyl)-5-methyl uridine.

To an ice-cold solution of triazole (19.9 g) in triethylamine (50 mL) and acetonitrile (150 mL), with mechanical stirring, 9 mL of $POCl_3$ was added dropwise. After the addition, the ice bath was removed and the mixture stirred for 30 min. The 2'-acetoxy-5'-O-(DMT)-3'-O-(2-methoxyethyl)-5-methyl uridine (16 g in 50 mL $CH_3CN$) was added dropwise to the above solution with the receiving flask kept at ice bath temperatures. After 2 hrs, TLC indicated a faster moving nucleoside, C-4-triazole-derivative. The reaction flask was evaporated and the nucleoside was partitioned between ethylacetate (500 mL) and $NaHCO_3$ (500 mL). The organic layer was washed with saturated NaCl solution, dried (anhydrous $NgSO_4$) and evaporated to give 15 g of C-4-triazole nucleoside. This compound was then dissolved in 2:1 mixture of $NH_4OH$/dioxane (100 mL:200 mL) and stirred overnight. TLC indicated disappearance of the starting material. The solution was evaporated and dissolved in methanol to crystallize out 9.6 g of 5'-O-(DMT)-3'-O-(2-methoxyethyl)5-methyl cytidine.

5'-O-DMT-3'-O-(2-methoxyethyl)-5-methyl cytidine (9.6 g, 0.015 mol) was dissolved in 50 mL of DMF and treated with 7.37 g of benzoic anhydride. After 24 hrs of stirring, DMF was evaporated and the residue was loaded on silica column and eluted with 1:1 hexane:ethylacetate to give the desired nucleoside.

Example 4

5'-O-DMT-3'-O-(2-Methoxyethyl)-$N^4$-benzoyl-5-methyl-cytidine-2'-O-(2-cyanoethyl-N,N-diisopropyl)phosphoramidite 5'-O-DMT-3'-O-(2-methoxyethyl)-$N^4$-benzoyl-5-methyl-cytidine-2'-O-(2-cyanoethyl-N,N-diisopropyl) phosphoramidite was obtained from the above nucleoside using the phosphitylation protocol described for the corresponding 5-methyl-uridine derivative.

Example 5

$N^6$-Benzoyl-5'-O-(DMT)-3'-O-(2-methoxyethyl) adenosine

A solution of adenosine (42.74 g, 0.16 mol) in dry dimethyl formamide (800 mL) at 5° C. was treated with sodium hydride (8.24 g, 60% in oil prewashed thrice with hexanes, 0.21 mol). After stirring for 30 min, 2-methoxyethyl bromide (0.16 mol) was added over 20 min. The reaction was stirred at 5° C. for 8 h, then filtered through Celite. The filtrate was concentrated under reduced pressure followed by coevaporation with toluene (2×100 mL). The residue was adsorbed on silica gel (100 g) and chromatographed (800 g, chloroform-methanol 9:14:1). Selected fractions were concentrated under reduced pressure and the residue was a mixture of 2'-O-(2-(methoxyethyl)adenosine and 3'-O-(2-methoxyethyl)adenosine in the ratio of 4:1.

The above mixture (0.056 mol) in pyridine (100 mL) was evaporated under reduced pressure to dryness. The residue was redissolved in pyridine (560 mL) and cooled in an ice water bath. Trimethylsilyl chloride (36.4 mL, 0.291 mol) was added and the reaction was stirred at 5° C. for 30 min. Benzoyl chloride (33.6 mL, 0.291 mol) was added and the reaction was allowed to warm to 25° C. for 2 h and then cooled to 5° C. The reaction was diluted with cold water (112 mL) and after stirring for 15 min, concentrated ammonium hydroxide (112 Ml) was added. After 30 min, the reaction was concentrated under reduced pressure (below 30° C.) followed by coevaporation with toluene (2×100 mL). The residue was dissolved in ethyl acetate-methanol (400 mL, 9:1) and the undesired silyl by-products were removed by filtration. The filtrate was concentrated under reduced pressure and then chromatographed on silica gel (800 g, chloroform-methanol 9:1). Selected fractions were combined, concentrated under reduced pressure and dried at 25° C./0.2 mmHg for 2 h to give pure $N^6$-Benzoyl-2'-O-(2-methoxyethyl)adenosine and pure $N^6$-Benzoyl-3'-O-(2-methoxyethyl)adenosine.

A solution of $N^6$-Benzoyl-3'-O-(2-methoxyethyl) adenosine (11.0 g, 0.285 mol) in pyridine (100 mL) was evaporated under reduced pressure to an oil. The residue was redissolved in dry pyridine (300 mL) and DMT-Cl (10.9 g, 95%, 0.31 mol) was added. The mixture was stirred at 25° C. for 16 h and then poured onto a solution of sodium bicarbonate (20 g) in ice water (500 mL). The product was extracted with ethyl acetate (2×150 mL). The organic layer was washed with brine (50 mL), dried over sodium sulfate (powdered) and evaporated under reduced pressure (below 40C). The residue was chromatographed on silica gel (400 g, ethyl acetate-acetonitrile-triethylamine 99:1:195:5:1). Selected fractions were combined, concentrated under reduced pressure and dried at 25° C./0.2 mmHg to give 16.8 g (73%) of the title compound as a foam. The TLC was homogenous.

Example 6

[N6-Benzoyl-5'-O-(DMT)-3'-O-(2-methoxyethyl) adenosin-2'-O-(2-cyanoethyl-N,N-diisopropyl) phosphoramidite The title compound was prepared in the same manner as the 5-methyl-cytidine and 5-methyluridine analogs of Examples 2 and 4 by starting with the title compound of Example 5. Purification using ethyl acetate-hexanes-triethylamine 59:40:1 as the chromatography eluent gave 67% yield of the title compound as a solid foam. The TLC was homogenous. $^{31}$P-NMR (CDCl$_3$, H$_3$PO$_4$ std.) δ 147.89; 148.36 (diastereomers).

Example 7

5'-O-(DMT)-$N^2$-Isobutyryl-3'-O-(2-methoxyethyl) guanosine

A. 2,6-Diaminopurine Riboside

To a 2 L stainless steel Parr bomb was added guanosine hydrate (100 g, 0.35 mol, Aldrich), hexamethyl) disilazane (320 mL, 1.52 mol, 4.4 eq.), trimethyl) silyl triflouromethanesulfonate (8.2 mL), and toluene (350 mL). The bomb was sealed and partially submerged in an oil bath (170° C.; internal T 150° C., 150 psi) for 5 days. The bomb was cooled in a dry ice/acetone bath and opened. The contents were transferred with methanol (300 mL) to a flask and the solvent was evaporated under reduced pressure. Aqueous methanol (50%, 1.2 L) was added. The resulting brown suspension was heated to reflux for 5 h. The suspension was concentrated under reduced pressure to one half volume in order to remove most of the methanol. Water (600 mL) was added and the solution was heated to reflux, treated with charcoal (5 g) and hot filtered through Celite. The solution was allowed to cool to 25° C. The resulting precipitate was collected, washed with water (200 mL) and dried at 90° C./0.2 mmHg for 5 h to give a constant weight of 87.4 g (89%) of tan, crystalline solid; mp 247° C. (shrinks), 255° C. (dec, lit. (1) mp 250–252° C.); TLC homogenous (Rf 0.50, isopropanol-ammonium hydroxide-water 16:3:1 ); PMR (DMSO), δ 5.73 (d, 2, 2-NH$_2$), 5.78 (s, 1, H-1), 6.83 (br s, 2, 6-NH$_2$).

B. 2'-O-(2-Methoxyethyl)-2,6-diaminopurine Riboside and 3'-O-(2-Methoxyethyl)-2,6-diaminopurine Riboside To a solution of 2,6-diaminopurine riboside (10.0 g, 0.035 mol) in dry dimethyl formamide (350 mL) at 0° C. under an argon atmosphere was added sodium hydride (60% in oil, 1.6 g, 0.04 mol). After 30 min., 2-methoxyethyl bromide (0.44 mol) was added in one portion and the reaction was stirred at 25° C. for 16 h. Methanol (10 mL) was added and the mixture was concentrated under reduced pressure to an oil (20 g). The crude product, containing a ratio of 4:1 of the 2'/3' isomers, was chromatographed on silica gel (500 g, chloroform-methanol 4:1). The appropriate fractions were combined and concentrated under reduced pressure to a semi-solid (12 g). This was triturated with methanol (50 mL) to give a white, hygroscopic solid. The solid was dried at 40° C./0.2 mmHg for 6 h to give a pure 2' product and the pure 3' isomer, which were confirmed by NMR.

C. 3'-O-2-(Methoxyethyl)guanosine

With rapid stirring, 3'-O-(2-methoxyethyl)-2,6-diaminopurine riboside (0.078 mol) was dissolved in monobasic sodium phosphate buffer (0.1 M, 525 mL, pH 7.3–7.4) at 25° C. Adenosine deaminase (Sigma type II, 1 unit/mg, 530 mg) was added and the reaction was stirred at 25° C. for 60 h. The mixture was cooled to 5° C. and filtered. The solid was washed with water (2×25 mL) and dried at 60° C./0.2 mmHg for 5 h to give 10.7 g of first crop material. A second crop was obtained by concentrating the mother liquors under reduced pressure to 125 mL, cooling to 5° C., collecting the solid, washing with cold water (2×20 mL) and drying as above to give 6.7 g of additional material for a total of 15.4 g (31% from guanosine hydrate) of light tan solid; TLC purity 97%.

D. $N^2$-Isobutyryl-3'-O-2-(methoxyethyl)guanosine

To a solution of 3'-O-2-(methoxyethyl)guanosine (18.1 g, 0.0613 mol) in pyridine (300 mL) was added trimethyl silyl chloride (50.4 mL, 0.46 mol). The reaction was stirred at 25° C. for 16 h. Isobutyryl chloride (33.2 mL, 0.316 mol) was added and the reaction was stirred for 4 h at 25° C. The reaction was diluted with water (25 mL). After stirring for 30 min, ammonium hydroxide (concentrated, 45 mL) was added until pH 6 was reached. The mixture was stirred in a water bath for 30 min and then evaporated under reduced pressure to an oil. The oil was suspended in a mixture of ethyl acetate, (600 mL) and water (100 mL) until a solution formed. The solution was allowed to stand for 17 h at 25° C. The resulting precipitate was collected, washed with ethyl acetate (2×50 mL) and dried at 60° C./0.2 mmHg for 5 h to give 16.1 g (85%) of tan solid; TLC purity 98%.

E. 5'-O-(DMT)-$N^2$-Isobutyryl-3'-O-(2-methoxyethyl) guanosine

A solution of $N^2$-Isobutyryl-3'-O-(2-methoxyethyl) guanosine (0.051 mol) in pyridine (150 mL) was evaporated under reduced pressure to dryness. The residue was redissolved in pyridine (300 mL) and cooled to 10–15° C. DMT-Cl (27.2 g, 95%, 0.080 mol) was added and the reaction was stirred at 25° C. for 16 h. The reaction was evaporated under reduced pressure to an oil, dissolved in a minimum of methylene chloride and applied on a silica gel column (500 g) The product was eluted with a gradient of methylene chloride-triethylamine (99:1) to methylene chloride-methanol-triethylamine (99:1:1). Selected fractions were combined, concentrated under reduced pressure and dried at 40° C./0.2 mmHg for 2 h to afford 15 g (15.5% from guanosine hydrate) of tan foam; TLC purity 98%.

Example 8

[5'-O-(DMT)-$N^2$-Isobutyryl-3'-O-(2-methoxyethyl) guanosin-2'-O-(2-cyanoethyl-N,N-diisopropyl) phosphoramidite The protected nucleoside from Example 7 (0.0486 mol) was placed in a dry 1 L round bottom flask containing a Teflon stir-bar. The flask was purged with argon. Anhydrous methylene chloride (400 mL) was cannulated into the flask to dissolve the nucleoside. Previously vacuum dried N,N-diisopropylaminohydrotetrazolide (3.0 g, 0.0174 mol) was added under argon. With stirring, bis-N,N-diisopropyl-aminocyanoethylphosphoramidite (18.8 g, 0.0689 mol) was added via syringe over 1 min (no exotherm noted). The reaction was stirred under argon at 25° C. for 16 h. After verifying the completion of the reaction by TLC, the reaction was transferred to a separatory funnel (1 L). The reaction flask was rinsed with methylene chloride (2×50 mL). The combined organic layer was washed with saturated aq. sodium bicarbonate (200 mL) and then brine (200 mL). The organic layer was dried over sodium sulfate (50 g, powdered) for 2 h. The solution was filtered and concentrated under reduced pressure to a viscous oil. The resulting phosphoramidite was purified by silica gel flash chromatography (800 g, ethyl acetate-triethylamine 99:1). Selected fractions were combined, concentrated under reduced pressure, and dried at 25C/0.2 mmHg for 16 h to give 18.0 g (46%, 3% from guanosine hydrate) of solid foam TLC homogenous. $^{31}$P-NMR (CDCl$_3$, H$_3$PO$_4$ std.) δ 147.96; 148.20 (diastereomers).

Example 9

5'-O-DMT-3'-O-(2-Methoxyethyl)-5-methyl-uridine-2'-O-succinate

5'-O-DMT-3'-O-(2-methoxyethyl)-thymidine was first succinylated on the 2'-position. Thymidine nucleoside (4 mmol) was reacted with 10.2 mL dichloroethane, 615 mg (6.14 mmol) succinic anhydride, 570 μL (4.09 mmol) triethylamine, and 251 mg (2.05 mmol) 4-dimethylaminopyridine. The reactants were vortexed until dissolved and placed in heating block at 55° C. for approximately 30 minutes. Completeness of reaction checked by thin layer chromatography (TLC). The reaction mixture was washed three times with cold 10% citric acid followed by three washes with water. The organic phase was removed and dried under sodium sulfate. Succinylated nucleoside was dried under P$_2$O$_5$ overnight in vacuum oven.

Example 10

5'-O-DMT-3'-O-Methoxyethyl-5-methyl-uridine-2'-O-succinoyl Linked LCA CPG

5'-O-DMT-3'-O-(2-methoxyethyl)-2'-O-succinyl-thymidine was coupled to controlled pore glass (CPG). 1.09 g (1.52 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). After about 24 hours, DMAP (1.52 mmol, 186 mg) and acetonitrile (13.7 mL) were added to the succinate. The mixture was stirred under an atmosphere of argon using a magnetic stirrer. In a separate flask, dTNP (1.52 mmol, 472 mg) was dissolved in acetonitrile (9.6 mL) and dichloromethane (4.1 mL) under argon. This reaction mixture was then added to the succinate. In another separate flask, TPP (1.52 mmol, 399 mg) was dissolved in acetonitrile (37 mL) under argon. This mixture was then added to the succinate/DMAP/dTNP reaction mixture. Finally, 12.23 g pre-acid washed LCA CPG (loading=115.2 μmol/g) was added to the main reaction mixture, vortexed shortly and placed on shaker for approximately 3 hours. The mixture was removed from the shaker after 3 hours and the loading was checked. A small sample of CPG was washed with copious amounts of acetonitrile, dichloromethane, and then with ether. The initial loading was found to be 63 μmol/g (3.9 mg of CPG was cleaved with trichloroacetic acid, the absorption of released trityl cation was read at 503 nm on a spectrophotometer to determine the loading.) The whole CPG sample was then washed as described above and dried under P$_2$O$_5$ overnight in vacuum oven. The following day, the CPG was capped with 25 mL CAP A (tetrahydrofuran/acetic anhydride) and 25 mL CAP B (tetrahydrofuran/pyridine/1-methyl imidazole) for approximately 3 hours on shaker. Filtered and washed with dichloromethane and ether. The CPG was dried under P$_2$O$_5$ overnight in vacuum oven. After drying, 12.25 g of CPG was isolated with a final loading of 90 μmol/g.

Example 11

3'-O-Methoxyethyl-5-methyl-N-benzoyl-cytidine-2'-O-succinate

5'-O-DMT-3'-O-(2-methoxy)ethyl-N-benzoyl-cytidine was first succinylated on the 2'-position. Cytidine nucleoside (4 mmol) was reacted with 10.2 mL dichloroethane, 615 mg (6.14 mmol) succinic anhydride, 570 μL (4.09 mmol) triethylamine, and 251 mg (2.05 mmol) 4-dimethylaminopyridine. The reactants were vortexed until dissolved and placed in a heating block at 55° C. for approximately 30 minutes. Completeness of reaction was checked by thin layer chromatography (TLC). The reaction mixture was washed three times with cold 10% citric acid followed by three washes with water. The organic phase was removed and dried under sodium sulfate. The succinylated nucleoside was dried under P$_2$O$_5$ overnight in vacuum oven.

Example 12

5'-O-DMT-3'-O-Methoxyethyl-5-methyl-N-benzoyl-cytidine-2'-O-succinoyl Linked LCA CPG 5'-O-DMT-3'-O-(2-methoxyethyl)-2'-O-succinyl-N$^4$-benzoyl cytidine was coupled to controlled pore glass (CPG). 1.05 g (1.30 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (1.30 mmol, 159 mg) and acetonitrile (11.7 mL) were added to the succinate. The mixture was "mixed" by a magnetic stirrer under argon. In a separate flask, dTNP (1.30 mmol, 400 mg) was dissolved in acetonitrile (8.2 mL) and dichloromethane (3.5 mL) under argon. This reaction mixture was then added to the succinate. In another separate flask, TPP (1.30 mmol, 338 mg) was dissolved in acetonitrile (11.7 mL) under argon. This mixture was then added to the succinate/DMAP/dTNP reaction mixture. Finally, 10.46 g pre-acid washed LCA CPG (loading=115.2 μmol/g) were added to the main reaction mixture, vortexed shortly and placed on shaker for approximately 2 hours. A portion was removed from shaker after 2 hours and the loading was checked. A small sample of CPG was washed with copious amounts of acetonitrile, dichloromethane, and then with ether. The initial loading was found to be 46 μmol/g. (3.4 mg of CPG were cleaved with trichloroacetic acid). The absorption of released trityl cation was read at 503 nm on a spectrophotometer to determine the loading. The whole CPG sample was then washed as described above and dried under P$_2$O$_5$ overnight in vacuum oven. The following day, the CPG was capped with 25 mL CAP A (tetrahydrofuran/acetic anhydride) and 25 mL CAP B (tetrahydrofuran/ pyridine/1-methyl imidazole) for approximately 3 hours on a shaker. The material was filtered and washed with dichloromethane and ether. The CPG was dried under $P_2O_5$ overnight in vacuum oven. After drying, 10.77 g of CPG was isolated with a final loading of 63 µmol/g.

Example 13

5'-DMT-3'-O-Methoxyethyl-N6-benzoyl-adenosine-2'-O-succinate

5'-O-DMT-3'-O-(2-methoxyethyl)-$N^6$-benzoyl adenosine was first succinylated on the 2'-position. 3.0 g (4.09 mmol) of the adenosine nucleoside were reacted with 10.2 mL dichloroethane, 615 mg (6.14 mmol) succinic anhydride, 570 µL (4.09 mmol) triethylamine, and 251 mg (2.05 mmol) 4-dimethylaminopyridine. The reactants were vortexed until dissolved and placed in heating block at 55° C. for approximately 30 minutes. Completeness of reaction was checked by thin layer chromatography (TLC). The reaction mixture was washed three times with cold 10% citric acid followed by three washes with water. The organic phase was removed and dried under sodium sulfate. Succinylated nucleoside was dried under $P_2O_5$ overnight in vacuum oven.

Example 14

5'-O-DMT-3'-O-(2-Methoxyethyl)-N6-benzoyl-adenosine-2'-O-succinoyl Linked LCA CPG Following succinylation, 5'-O-DMT-3'-O-(2-methoxyethyl)-2'-O-succinyl-$N^6$-benzoyl adenosine was coupled to controlled pore glass (CPG). 3.41 g (4.10 mmol) of the succinate were dried overnight in a vacuum oven along with 4-dimethylaminopyridine (DMAP), 2,2'-dithiobis (5-nitropyridine) (dTNP), triphenylphosphine (TPP), and pre-acid washed CPG (controlled pore glass). The following day, DMAP (4.10 mmol, 501 mg) and acetonitrile (37 mL) were added to the succinate. The mixture was "mixed" by a magnetic stirrer under argon. In a separate flask, dTNP (4.10 mmol, 1.27g) was dissolved in acetonitrile (26 mL) and dichloromethane (11 mL) under argon. This reaction mixture was then added to the succinate. In another separate flask, TPP (4.10 mmol, 1.08 g) was dissolved in acetonitrile (37 mL) under argon. This mixture was then added to the succinate/DMAP/dTNP reaction mixture. Finally, 33 g pre-acid washed LCA CPG (loading=115.2 µmol/g) were added to the main reaction mixture, vortexed shortly and placed on shaker for approximately 20 hours. Removed from shaker after 20 hours and the loading was checked. A small sample of CPG was washed with copious amounts of acetonitrile, dichloromethane, and then with ether. The initial loading was found to be 49 µmol/g. (2.9 mg of CPG were cleaved with trichloroacetic acid). The absorption of released trityl cation was read at 503 nm on a spectrophotometer to determine the loading. The whole CPG sample was then washed as described above and dried under $P_2O_5$ overnight in vacuum oven. The following day, the CPG was capped with 50 mL CAP A (tetrahydrofuran/acetic anhydride) and 50 mL CAP B (tetrahydrofuran/pyridine/1-methyl imidazole) for approximately 1 hour on the shaker. The material was filtered and washed with dichloromethane and ether. The CPG was dried under $P_2O_5$ overnight in vacuum oven. After drying, 33.00 g of CPG was obtained with a final loading of 66 µmol/g.

Example 15

5'-O-DMT-3'-O-(2-Methoxyethyl)-N2-isobutyryl-guanosine-2'-O-succinate

5'-O-DMT-3'-O-(2-methoxyethyl)-$N^2$-isobutyryl guanosine was succinylated on the 2'-sugar position. 3.0 g (4.20 mmol) of the guanosine nucleoside were reacted with 10.5 mL dichloroethane, 631 mg (6.30 mmol) succinic anhydride, 585 µL (4.20 mmol) triethylamine, and 257 mg (2.10 mmol) 4-dimethylaminopyridine. The reactants were vortexed until dissolved and placed in heating block at 55° C. for approximately 30 minutes. Completeness of reaction checked by thin layer chromatography (TLC). The reaction mixture was washed three times with cold 10% citric acid followed by three washes with water. The organic phase was removed and dried under sodium sulfate. The succinylated nucleoside was dried under $P_2O_5$ overnight in vacuum oven.

Example 16

5'-O-DMT-3'-O-Methoxyethyl-N2-isobutyryl-guanosine-2'-O-succinoyl Linked LCA CPG Following succinylation, 5'-O-DMT-3'-O-(2-methoxyethyl)-2'-O-succinyl-$N^2$-benzoyl guanosine was coupled to controlled pore glass (CPG). 3.42 g (4.20 mmol) of the succinate were dried overnight in a vacuum oven along with 4-dimethylaminopyridine (DMAP), 2,2'-dithiobis (5-nitropyridine) (dTNP), triphenylphosphine (TPP), and pre-acid washed CPG (controlled pore glass). The following day, DMAP (4.20 mmol, 513 mg) and acetonitrile (37.5 mL) were added to the succinate. The mixture was "mixed" by a magnetic stirrer under argon. In a separate flask, dTNP (4.20 mmol, 1.43 g) was dissolved in acetonitrile (26 mL) and dichloromethane (11 mL) under argon. This reaction mixture was then added to the succinate. In another separate flask, TPP (4.20 mmol, 1.10 g) was dissolved in acetonitrile (37. 5 mL) under argon. This mixture was then added to the succinate/DMAP/dTNP reaction mixture. Finally, 33.75 g pre-acid washed LCA CPG (loading=115.2 µmol/g) were added to the main reaction mixture, vortexed shortly and placed on shaker for approximately 20 hours. Removed from shaker after 20 hours and the loading was checked. A small sample of CPG was washed with copious amounts of acetonitrile, dichloromethane, and then with ether. The initial loading was found to be 64 µmol/g. (3.4 mg of CPG were cleaved with trichloroacetic acid). The absorption of released trityl cation was read at 503 nm on a spectrophotometer to determine the loading. The CPG was then washed as described above and dried under $P_2O_5$ overnight in vacuum oven. The following day, the CPG was capped with 50 mL CAP A (tetrahydrofuran/acetic anhydride) and 50 mL CAP B (tetrahydrofuran/pyridine/1-methyl imidazole) for approximately 1 hour on a shaker. The material was filtered and washed with dichloromethane and ether. The CPG was dried under $P_2O_5$ overnight in vacuum oven. After drying, 33.75 g. of CPG was isolated with a final loading of 72 µmol/g.

Example 17

5'-O-DMT-3'-O-[Hexyl-(6-phthalimido)]-uridine

2',3'-O-Dibutyl stannylene-uridine was synthesized according to the procedure of Wagner et. al., *J. Org. Chem.*, 1974, 39, 24. This compound was dried over $P_2O_5$ under vacuum for 12 hours. To a solution of this compound (29 g, 42.1 mmol) in 200 mL of anhydrous DMF were added (16.8 g, 55 mmol) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2 L of EtOAc followed by eluting with 10% methanol (MeOH):90% EtOAc. The product, 2'- and 3'-isomers of O-hexyl-6-N-phthalimido uridine, eluted as an inseparable mixture ($R_f$=0.64 in 10% MeOH in EtOAc). By $^{13}$C NMR, the isomeric ration was about 55% of the 2' isomer and about 45% of the 3' isomer. The combined yield was 9.2 g (46.2%). This mixture was dried under vacuum and re-evaporated twice with pyridine. It was dissolved in 150 mL anhydrous pyridine and treated with 7.5 g of DMT-Cl (22.13 mmol) and 500 mg of dimethylaminopyridine (DMAP). After 2 hours, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of CH$_3$OH and evaporated under reduced pressure. The residue was dissolved in 300 mL CH$_2$Cl$_2$, washed successively with saturated NaHCO$_3$ followed by saturated NaCl solution. It was dried over Mg$_2$SO$_4$ and evaporated to give 15 g of a brown foam which was purified on a silica gel (500 g) to give 6.5 g of the 2'-isomer and 3.5 g of the 3' isomer.

Example 18

5'-O-DMT-3'-O-[Hexyl-(6-phthalimido)]-uridine-2'-O-(2-cyanoethyl-N,N,-diisopropyl)phosphoramidite 5'-DMT-3'-O-[hexyl-(6-phthalimido)]uridine (2 g, 2.6 mmol) was dissolved in 20 mL anhydrous CH$_2$Cl$_2$. To this solution diisopropylaminotetrazolide (0.2 g, 1.16 mmol) and 2.0 mL 2-cyanoethyl-N,N,N',N'-tetraisopropyl phosphoramidite (6.3 mmol) were added with stirred overnight. TLC (1:1 EtOAc/hexane) showed complete disappearance of starting material. The reaction mixture was transferred with CH$_2$Cl$_2$ and washed with saturated NaHCO$_3$ (100 mL), followed by saturated NaCl solution. The organic layer was dried over anhydrous Na$_2$SO$_4$ and evaporated to yield 3.8 g of a crude product, which was purified in a silica column (200 g) using 1:1 hexane/EtOAc to give 1.9 g (1.95 mmol, 74% yield) of the desired phosphoramidite.

Example 19

Preparation of 5'-O-DMT-3'-O-[Hexyl-(6-phthalimido)]-uridine-2'-O-succinoyl-aminopropyl CPG Succinylated and capped aminopropyl controlled pore glass (CPG; 500 Å pore diameter, aminopropyl CPG, 1.0 grams prepared according to Damha et. al., *Nucl. Acids Res.* 1990, 18, 3813.) was added to 12 mL anhydrous pyridine in a 100 mL round-bottom flask. 1-(3-Dimethylaminopropyl)-3-ethyl-carbodiimide (DEC; 0.38 grams, 2.0 mmol)], triethylamine (TEA; 100 μl, distilled over CaH$_2$), dimethylaminopyridine (DMAP; 0.012 grams, 0.1 mmol) and nucleoside 5'-O-DMT-3'-O-[hexyl-(6-phthalimido)]uridine (0.6 grams, 0.77 mmol) were added under argon and the mixture shaken mechanically for 2 hours. Additional nucleoside (0.20 grams) was added and the mixture shaken for 24 hours. The CPG was filtered off and washed successively with dichloromethane, triethylamine, and dichloromethane. The CPG was then dried under vacuum, suspended in 10 mL piperidine and shaken 15 minutes. The CPG was filtered off, washed thoroughly with dichloromethane and again dried under vacuum. The extent of loading (determined by spectrophotometric assay of DMT cation in 0.3 M p-toluenesulfonic acid at 498 nm) was approximately 28 μmol/g. The 5'-O-(DMT)-3'-O-[hexyl-(6-phthalimido] uridine-2'-O-succinyl-aminopropyl controlled pore glass was used to synthesize the oligomers in an ABI 380B DNA synthesizer using phosphoramidite chemistry standard conditions. A four base oligomer 5'-GACU*-3' was used to confirm the structure of 3'-O-hexylamine tether introduced into the oligonucleotide by NMR. As expected a multiplet signal was observed between 1.0–1.8 ppm in $^1$H NMR.

Example 20

5'-O-DMT-3'-O-[Hexylamino]-uridine

5'-O-(DMT)-3'-O-[hexyl-(6-phthalimido)]uridine (4.5 grams, 5.8 mmol) is dissolved in 200 mL methanol in a 500 mL flask. Hydrazine (1 ml, 31 mmol) is added to the stirring reaction mixture. The mixture is heated to 60–65° C. in an oil bath and refluxed 14 hours. The solvent is evaporated in vacuo and the residue is dissolved in dichloromethane (250 mL) and extracted twice with an equal volume NH$_4$OH. The organic layer is evaporated to yield the crude product which NMR indicates is not completely pure. $R_f$=0 in 100% ethyl acetate. The product is used in subsequent reactions without further purification.

Example 21

3'-O-[Propyl-(3-phthalimido)]-adenosine

To a solution of adenosine (20.0 g, 75 mmol) in dry dimethylformamide (550 ml) at 5° C. was added sodium hydride (60% oil, 4.5 g, 112 mmol). After one hour, N-(3-bromopropyl)phthalimide (23.6 g, 86 mmol) was added and the temperature was raised to 30° C. and held for 16 hours. Ice is added and the solution evaporated in vacuo to a gum. The gum was partitioned between water and ethyl acetate (4×300 mL). The organic phase was separated, dried, and evaporated in vacuo and the resultant gum chromatographed on silica gel (95/5 CH$_2$Cl$_2$/MeOH) to give a white solid (5.7 g) of the 2'-O-(propylphthalimide)adenosine. Thee fractions containing the 3'-O-(propylphthalimide)adenosine were chromatographed a second time on silica gel using the same solvent system.

Crystallization of the 2'-O-(propylphthalimide)adenosine fractions from methanol gave a crystalline solid, m.p. 123–124C. $^1$H NMR (400 MHZ: DMSO-d$_6$) δ 1.70(m, 2H, CH$_2$), 3.4–3.7 (m, 6H, C$_5$, CH$_2$, OCH$_2$, Phth CH$_2$), 3.95 (q, 1H, C$_4$,H), 4.30 (q, 1H, C$_5$,H), 4.46 (t, 1H, C$_2$,H), 5.15 (d, 1H, C$_3$,OH), 5.41 (t, 1H, C$_5$,OH), 5.95 (d, 1H, C$_1$,H) 7.35 (s, 2H, NH$_2$), 7.8 (brs, 4H, Ar), 8.08 (s, 1H, C$_2$H) and 8.37 (s, 1H, C$_8$H). Anal. Calcd. C$_{21}$H$_{22}$N$_6$O$_6$: C, 55.03; H, 4.88; N, 18.49. Found: C, 55.38; H, 4.85; N, 18.46.

Crystallization of the 3'-O-(propylphthalimide)adenosine fractions from H$_2$O afforded an analytical sample, m.p. 178–179C. $^1$H NMR (400 MHZ: DMSO-d$_6$) δ 5.86 (d, 1H, H-1').

Example 22

3'-O-[Propyl-(3-phthalimido)]-N6-benzoyl-adenosine

3'-O-(3-propylphthalimide)adenosine is treated with benzoyl chloride in a manner similar to the procedure of Gaffney, et al., *Tetrahedron Lett.* 1982, 23, 2257. Purification of crude material by chromatography on silica gel (ethyl acetate-methanol) gives the title compound.

Example 23

3'-O-[Propyl-(3-phthalimido)]-5'-O-DMT-N6-benzoyl-adenosine

To a solution of 3'-O-(propyl-3-phthalimide)-N$^6$-benzoyladenosine (4.0 g) in pyridine (250 ml) is added DMT-Cl (3.3 g). The reaction is stirred for 16 hours. The reaction is added to ice/water/ethyl acetate, the organic layer separated, dried, and concentrated in vacuo and the resultant gum chromatographed on silica gel (ethyl acetate-methanol triethylamine) to give the title compound.

Example 24

3'-O-[Propyl-(3-phthalimido)]-5'-O-DMT-N6-Benzoyl-adenosine-2'-O-(2-cyanoethyl-N,N-diisopropyl)phosphoramidite 3'-O-(Propyl-3-phthalimide)-5'-O-DMT-$N^6$-benzoyladenosine is treated with (β-cyanoethoxy)chloro-N,N-diisopropyl)aminophosphane in a manner similar to the procedure of Seela, et al., *Biochemistry* 1987, 26, 2233. Chromatography on silica gel (EtOAc/hexane) gives the title compound as a white foam.

Example 25

3'-O-(Aminopropyl)-adenosine

A solution of 3'-O-(propyl-3-phthalimide)adenosine (8.8 g, 19 mmol), 95% ethanol (400 mL) and hydrazine (10 mL, 32 mmol) is stirred for 16 hrs at room temperature. The reaction mixture is filtered and filtrate concentrated in vacuo. Water (150 mL) is added and acidified with acetic acid to pH 5.0. The aqueous solution is extracted with EtOAc (2×30 mL) and the aqueous phase is concentrated in vacuo to afford the title compound as a HOAc salt.

Example 26

3'-O-[3-(N-Trifluoroacetamido)propyl]-adenosine

A solution of 3'-O-(propylamino)adenosine in methanol (50 mL) and triethylamine (15 mL, 108 mmol) is treated with ethyl trifluoroacetate (18 mL, 151 mmol). The reaction is stirred for 16 hrs and then concentrated in vacuo and the resultant gum chromatographed on silica gel (9/1, EtOAc/MeOH) to give the title compound.

Example 27

N6-Dibenzoyl-3'-O-[3-(N-trifluoroacetamido)propyl]-adenosine

3'-O-[3-(N-trifluoroacetamido)propyl]adenosine is treated as per Example 22 using a Jones modification wherein tetrabutylammonium fluoride is utilized in place of ammonia hydroxide in the work up. The crude product is purified using silica gel chromatography (EtOAc/MeOH 1/1) to give the title compound.

Example 28

N6-Dibenzoyl-5'-O-DMT-3'-O-[3-(N-trifluoroacetamido)propyl]-adenosine

DMT-Cl (3.6 g, 10.0 mmol) is added to a solution of $N^6$-(dibenzoyl)-3'-O-[3-(N-trifluoroacetamido)propyl)adenosine in pyridine (100 mL) at room temperature and stirred for 16 hrs. The solution is concentrated in vacuo and chromatographed on silica gel (EtOAc/TEA 99/1) to give the title compound.

Example 29

N6-Dibenzoyl-5'-O-DMT-3'-O-[3-(N-trifluoroacetamido)propyl]-adenosine-2'-O-(2-cyanoethyl-N,N-diisopropyl)phosphoramidite A solution of $N^6$-(dibenzoyl)-5'-O-(DMT)-3'-O-[3-(N-trifluoroacetamido)propyl]adenosine in dry $CH_2Cl_2$ is treated with bis-N,N-diisopropylamino cyanoethyl phosphite (1.1 eqiv) and N,N-diisopropylaminotetrazolide (catalytic amount) at room temperature for 16 hrs. The reaction is concentrated in vacuo and chromatographed on silica gel (EtOAc/hexane/TEA 6/4/1) to give the title compound.

Example 30

3'-O-(Butylphthalimido)-adenosine

The title compound is prepared as per Example 21, using N-(4-bromobutyl)phthalimide in place of the 1-bromopropane. Chromatography on silica gel (EtOAC-MeOH) gives the title compound. $^1$H NMR (200 MHZ, DMSO-$d_6$) δ 5.88 (d, 1H, $C_1$,H)

Example 31

N6-Benzoyl-3'-O-(butylphthalimido)-adenosine

Benzoylation of 3'-O-(butylphthalimide)adenosine as per Example 22 gives the title compound.

Example 32

N6-Benzoyl-5'-O-DMT-3'-O-(butylphthalimido)-adenosine

The title compound is prepared from 3'-O-(butylphthalimide)-$N^6$-benzoyladenosine as per Example 22.

Example 33

N6-Benzoyl-5'-O-DMT-3'-O-(butylphthalimido)-adenosine-2'-O-(2-cyanoethyl-N,N-diisopropyl) phosphoramidite The title compound is prepared from 3'-O-(butylphthalimide)-5'-O-DMT-$N^6$-benzoyladenosine as per Example 24.

Example 34

3'-O-(Pentylphthalimido)-adenosine

The title compound is prepared as per Example 21, using N-(5-bromopentyl)phthalimide. The crude material from the extraction is chromatographed on silica gel using $CHCl_3$/MeOH (95/5) to give a mixture of the 2' and 3' isomers. The 2' isomer is recrystallized from EtOH/MeOH 8/2. The mother liquor is rechromatographed on silica gel to afford the 3' isomer. 2'-O-(Pentylphthalimido)adenosine: M.P. 159–160° C. Anal. Calcd. for $C_{23}H_{24}N_6O_5$: C, 57.26; H, 5.43; N, 17.42. Found: C,57.03; H, 5.46; N, 17.33. 3'-O-(Pentylphthalimido)adenosine: $^1$H NMR (DMSO-$d_6$) δ 5.87 (d, 1H, H-1').

Example 35

N6-Benzoyl-3'-O-(pentylphthalimido)-adenosine

Benzoylation of 3'-O-(pentylphthalimide)adenosine is achieved as per the procedure of Example 22 to give the title compound.

Example 36

N6-Benzoyl-5'-O-DMT-3'-O-(pentylphthalimido)-adenosine

The title compound is prepared from 3'-O-(pentylphthalimide)-$N^6$-benzoyladenosine as per the procedure of Example 23. Chromatography on silica gel (ethylacetate, hexane, triethylamine), gives the title compound.

Example 37

N6-Benzoyl-5'-O-DMT-3'-O-(pentylphthalimido)-adenosine-2'-O-(2-cyanoethyl-N,N-diisopropyl) phosphoramidite The title compound is prepared from 3'-O-(pentylphthalimide)-5'-O-(DMT)-N$^6$-benzoyladenosine as per the procedure of Example 24 to give the title compound.

Example 38

3'-O-(Propylphthalimido)uridine

A solution of uridine-tin complex (48.2 g, 115 mmol) in dry DMF (150 ml) and N-(3-bromopropyl)phthalimide (46 g, 172 mmol) was heated at 130° C. for 6 hrs. The crude product was chromatographed directly on silica gel CHCl$_3$/MeOH 95/5. The isomer ratio of the purified mixture was 2'/3' 81/19. The 2' isomer was recovered by crystallization from MeOH. The filtrate was rechromatographed on silica gel using CHCl$_3$CHCl$_3$/MeOH (95/5) gave the 3' isomer as a foam. 2'-O-(Propylphthalimide)uridine: Analytical sample recrystallized from MeOH, m.p. 165.5–166.5C, $^1$H NMR (200 MHZ, DMSO-d$_6$) δ 1.87 (m, 2H, CH$_2$), 3.49–3.65 (m, 4H, C$_2$H), 3.80–3.90 (m, 2H, C$_3$H$_1$C$_4$H), 4.09(m, 1H, C$_2$H), 5.07 (d, 1h, C$_3$OH), 5.16 (m, 1H, C$_5$OH), 5.64 (d, 1H, CH=), 7.84 (d, 1H, C$_1$H), 7.92 (bs, 4H, Ar), 7.95 (d, 1H, CH=) and 11.33 (s, 1H, ArNH). Anal. C$_{20}$H$_{21}$N$_3$H$_8$, Calcd. C, 55.69; H, 4.91; N, 9.74. Found, C, 55.75; H, 5.12; N, 10.01. 3'-O-(Propylphthalimide)uridine: $^1$H NMR (DMSO-d$_6$) δ 5.74 (d, 1H, H-1').

Example 39

3'-O-(Aminopropyl)-uridine

The title compound is prepared as per the procedure of Example 25.

Example 40

3'-O-[3-(N-Trifluoroacetamido)propyl]-uridine

3'-O-(Propylamino)uridine is treated as per the procedure of Example 26 to give the title compound.

Example 41

5'-O-DMT-3'-O-[3-(N-Trifluoroacetamido)propyl]-uridine

3'-O-[3-(N-trifluoroacetamido)propyl]uridine is treated as per the procedure of Example 28 to give the title compound.

Example 42

5'-O-DMT-3'-O-[3-(N-Trifluoroacetamido)propyl]-uridine-2'-O-(2-cyanoethyl-N,N-diisopropyl) phosphoramidite 5'-O-(DMT)-3'-O-[3-(N-trifluoroacetamido)propyl] uridine is treated as per the procedure of Example 29 to give the title compound.

Example 43

3'-O-(Propylphthalimido)-cytidine

The title compounds were prepared as per the procedure of Example 21.

2'-O-(propylphthalimide)cytidine: $^1$H NMR (200 MHZ, DMSO-d$_6$) δ 5.82 (d, 1H, C$_1$H).
3'-O-(propylphthalimide)cytidine: $^1$H NMR (200 MHZ, DMSO-d$_6$) δ 5.72 (d, 1H, C$_1$H).

Example 44

3'-O-(Aminopropyl)-cytidine

3'-O-(Propylphthalimide)cytidine is treated as per the procedure of Example 25 to give the title compound.

Example 45

3'-O-[3-(N-Trifluoroacetamido)propyl]-cytidine

3'-O-(Propylamino)cytidine is treated as per the procedure of Example 26 to give the title compound.

Example 46

N4-Benzoyl-3'-O-[3-(N-trifluoroacetamido)propyl]-cytidine

3'-O-[3-(N-trifluoroacetamido)propyl]cytidine is treated as per the procedure of Example 27 to give the title compound.

Example 47

N4-Benzoyl-5'-O-DMT-3'-O-[3-(N-trifluoroacetamido)propyl]-cytidine

N$^4$-(Benzoyl)-3'-O-[3-(N-trifluoroacetamido)propyl]-cytidine is treated as per the procedure of Example 28 to give the title compound.

Example 48

N4-Benzoyl-5'-O-DMT-3'-O-[3-(N-trifluoroacetamido)propyl]-cytidine-2'-O-(2-cyanoethyl-N,N-diisopropyl)phosphoramidite N$^4$-(Benzoyl)-5'-O-(DMT)-3'-O-[3-(N-trifluoroacetamido)propyl]cytidine is treated as per the procedure of Example 29 to give the title compound.

Example 49

General Procedures for Oligonucleotide Synthesis

Oligonucleotides were synthesized on a Perseptive Biosystems Expedite 8901 Nucleic Acid Synthesis System. Multiple 1-μmol syntheses were performed for each oligonucleotide. Trityl groups were removed with trichloroacetic acid (975 μL over one minute) followed by an acetonitrile wash. All standard amidites (0.1M) were coupled twice per cycle (total coupling time was approximately 4 minutes). All novel amidites were dissolved in dry acetonitrile (100 mg of amidite/1 mL acetonitrile) to give approximately 0.08–0.1 M solutions. Total coupling time was approximately 6 minutes (105 μL of amidite delivered). 1-H-tetrazole in acetonitrile was used as the activating agent. Excess amidite was washed away with acetonitrile. (1S)-(+)-(10-camphorsulfonyl)oxaziridine (CSO, 1.0 g CSO/8.72 mL dry acetonitrile) was used to oxidize (4 minute wait step) phosphodiester linkages while 3H-1,2-benzodithiole-3-one-1,1-dioxide (Beaucage reagent, 3.4 g Beaucage reagent/200 mL acetonitrile) was used to oxidize (one minute wait step) phosphorothioate linkages. Unreacted functionalities were capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. The oligonucleotides were deprotected in 1 mL 28.0–30% ammonium hydroxide (NH$_4$OH) for approximately 16 hours at 55° C. Oligonucleotides were also made on a larger scale (20 μmol/synthesis). Trityl groups were removed with just over 8 mL of trichloroacetic acid. All standard amidites (0.1M) were coupled twice per cycle (13 minute coupling step). All novel amidites were also coupled four times per cycle but the coupling time was increased to approximately 20 minutes (delivering 480 μL of amidite). Oxidation times remained the same but the delivery of oxidizing agent increased to approximately 1.88 mL per cycle. Oligonucleotides were cleaved and deprotected in 5 mL 28.0–30% NH$_4$OH at 55° C., for approximately 16 hours.

TABLE I

3'-O-(2-methoxyethyl) containing 2'–5' linked oligonucleotides.

| ISIS # | Sequence (5'–3')[1] | Backbone | Chemistry |
|---|---|---|---|
| 17176 | ATG-CAT-TCT-GCC-CCC-AAG-GA* | P=S | 3'-O—MOE |
| 17177 | ATG-CAT-TCT-GCC-CCC-AAG-G*A* | P=S | 3'-O—MOE |
| 17178 | ATG-CAT-TCT-GCC-CCC-AAG$_o$-G*$_o$A* | P=S/P=O | 3'-O—MOE |
| 17179 | A*TG-CAT-TCT-GCC-CCC-AAG-GA* | P=S | 3'-O—MOE |
| 17180 | A*TG-CAT-TCT-GCC-CCC-AAG-G*A* | P=S | 3'-O—MOE |
| 17181 | A*$_o$TG-CAT-TCT-GCC-AAA-AAG$_o$-G*$_o$A* | P=S/P=O | 3'-O—MOE |
| 21415 | A*T*G-CAT-TCT-GCC-AAA-AAG-G*A* | P=S | 3'-O—MOE |
| 21416 | A*$_o$T*$_o$G-CAT-TCT-GCC-AAA-AAG$_o$-G*$_o$A* | P=S/P=O | 3'-O—MOE |
| 21945 | A*A*A* | P=O | 3'-O—MOE |
| 21663 | A*A*A*A* | P=O | 3'-O—MOE |
| 20389 | A*U*C*G* | P=O | 3'-O—MOE |
| 20390 | C*G*C*-G*A*A*-T*T*C*-G*C*G* | P=O | 3'-O—MOE |

[1]All nucleosides with an asterisk contain 3'-O-(2-methoxyethyl).

Example 50

General Procedure for Purification of Oligonucleotides

Following cleavage and deprotection step, the crude oligucleotides (such as those synthesized in Example 49) were filtered from CPG using Gelman 0.45 μm nylon acrodisc syringe filters. Excess NH$_4$OH was evaporated away in a Savant AS160 automatic speed vac. The crude yield was measured on a Hewlett Packard 8452A Diode Array Spectrophotometer at 260 nm. Crude samples were then analyzed by mass spectrometry (MS) on a Hewlett Packard electrospray mass spectrometer and by capillary gel electrophoresis (CGE) on a Beckmann P/ACE system 5000. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Larger oligo yields from the larger 20 μmol syntheses were purified on larger HPLC columns (Waters Bondapak HC18HA) and the flow rate was increased to 5.0 mL/min. Appropriate fractions were collected and solvent was dried down in speed vac. Oligonucleotides were detritylated in 80% acetic acid for approximately 45 minutes and lyophilized again. Free trityl and excess salt were removed by passing detritylated oligonucleotides through Sephadex G-25 (size exclusion chromatography) and collecting appropriate samples through a Pharmacia fraction collector. Solvent again evaporated away in speed vac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm.

TABLE II

Physical characteristics of 3'-O-(2-methoxyethyl) containing 2'–5' linked oligonucleotides.

| | | | HPLC[2] | |
|---|---|---|---|---|
| | Expected Mass | Observed Mass | T$_R$ (min.) | #Ods(260 nm) Purified |
| 17176 | 6440.743 | 6440.300 | 23.47 | 3006 |
| 17177 | 6514.814 | 6513.910 | 23.67 | 3330 |
| 17178 | 6482.814 | 6480.900 | 23.06 | 390 |
| 17179 | 6513.798 | 6513.560 | 23.20 | 3240 |
| 17180 | 6588.879 | 6588.200 | 23.96 | 3222 |
| 17181 | 6540.879 | 6539.930 | 23.01 | |
| 21415 | 6662.976 | 6662.700 | 24.18 | 4008 |
| 21416 | 6598.969 | 6597.800 | 23.01 | 3060 |
| 21945 | 1099.924 | 1099.300 | 19.92 | 121 |
| 21663 | 1487.324 | 1486.800 | 20.16 | 71 |
| 20389 | 1493.000 | 1482.000 | | 62 |
| 20390 | 4588.000 | 4591.000 | | 151 |

[2]Conditions: Waters 600E with detector 991; Waters C4 column (3.9 × 300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

Example 51

T$_m$ on Modified Oligonucleotides

Oligoucleotides synthesized in Examples 49 and 50 were evaluated for their relative ability to bind to their complementary nucleic acids by measurement of their melting temperature (T$_m$) The melting temperature (T$_m$), a characteristic plysical property of double helices, denotes the temperature (in degrees centigrade) at which 50% helical (hybridized) versus coil (unhybridized) forms are present. $T_m$ is measured by using the UV spectrum to determine the formulation and breakdown (melting) of the hybridization complex. Base stacking, which occurs during hybridization, is accomanied by a reduction in UV absorption (hypochromicity). Consequently, a reduction in UV absorption indicates a higher $T_m$. The higher the $T_m$, the greater the strength of the bonds between the strands.

Selected test oligonucleotides and their complementary nucleic acids were incubated at a standard concentration of 4 μM for each oligonucleotide in buffer (100 mM NaCl, 10 mM sodium phosphate, pH 7.0, 0.1 mM EDTA). Samples were heated to 90° C. and the initial absorbance taken using a Guilford Response II Spectrophotometer (Corning). Samples were then slowly cooled to 15° C. and then the change in absorbance at 260 nm was monitored with heating during the heat denaturation procedure. The temperature was increased by 1 degree ° C./absorbance reading and the denaturation profile analyzed by taking the $1^{st}$ derivative of the melting curve. Data was also analyzed using a two-state linear regression analysis to determine the Tm=s. The results of these tests for the some of the oligonucleotides from Examples 49 and 50 are shown in Table III below.

2'-5' linked have different retention times in RP HPLC and hence different lipophilicities, implying potentially different extent of interactions with cell membranes.

Example 53

$T_m$ Analysis of 2',5'-Linked Oligonucleotides Versus 3',5'-Linked Oligonucleotides Thermal melts were done as per standardized literature procedures. Oligonucleotide identity is as follows: Oligonucleotide A is a normal 3'-5' linked phosphodiester oligodeoxyribonucleotide of the sequence d(GGC TGU* CTG CG) (SEQ ID NO: 16) where the * indicates the attachment site of a 2'-aminolinker. bligonucleotide B is a normal 3'-5' linked phosphodiester oligoribonucleotide of the sequence d(GGC TGU* CTG CG) where the * indicates the attachment site of a 2'-aminolinker. Each of the ribonucleotides of the oligonucleotide, except the one bearing the * substituent, are 2'-O-methyl ribonucleotides. Oligonucleotide C has 2'-5' linkage at the * position in addition to a 3'-aminolinker at this site. The remainder of the oligonucleotide is a phosphodiester oligodeoxyribonucleotide of the sequence d(GGC TGU* CTG CG). The base oligonucleotide (no 2'-aminolinker) was not included in the study.

TABLE III

Tm Analysis of Oligonucleotides

| ISIS # | Sequence (5'–3') | Backbone | $T_m$ | # Mods | # 2'–5' Linkages |
|---|---|---|---|---|---|
| 11061 | ATG-CAT-TCT-GCC-CCC-AAG-GA (SEQ ID NO: 14) | P=S | 61.4 | 0 | 0 |
| 17176 | ATG-CAT-TCT-GCC-CCC-AAG-GA* | P=S | 61.4 | 1 | 0 |
| 17177 | ATG-CAT-TCT-GCC-CCC-AAG-G*A* | P=S | 61.3 | 2 | 1 |
| 17178 | ATG-CAT-TCT-GCC-CCC-AAG$_o$-G*$_o$A* | P=S/P=O | 61.8 | 2 | 1 |
| 17179 | A*TG-CAT-TCT-GCC-CCC-AAG-GA* | P=S | 61.1 | 2 | 1 |
| 17180 | A*TG-CAT-TCT-GCC-CCC-AAG-G*A* | P=S | 61.0 | 3 | 2 |
| 17181 | A*$_o$TG-CAT-TCT-GCC-AAA-AAG$_o$-G*$_o$A* (SEQ ID NO: 15) | P=S/P=O | 61.8 | 3 | 2 |
| 21415 | A*T*G-CAT-TCT-GCC-AAA-AAG-G*A* | P=S | 61.4 | 4 | 3 |
| 21416 | A*$_o$T*$_o$G-CAT-TCT-GCC-AAA-AAG$_o$-G*$_o$A* | P=S/P=O | 61.7 | 4 | 3 |

[1]All nucleosides with an asterisk contain 3'-O-(2-methoxyethyl).

Example 52

NMR Experiments on Modified Oligonucleotides Comparison of 3',5' Versus 2',5' Internucleotide Linkages and 2'-Substituents Versus 3'-Substituents by NMR The 400 MHz $^1$H spectrum of oligomer d(GAU$_2$*CT), where U$_2$*=2'-O-aminohexyluridine showed 8 signals between 7.5 and 9.0 ppm corresponding to the 8 aromatic protons. In addition, the anomeric proton of U* appears as a doublet at 5.9 ppm with $J_{1',2'}$=7.5 Hz, indicative of C2'-endo sugar puckering. The corresponding 2'-5' linked isomer shows a similar structure with $J_{1',2'}$=3.85 Hz at 5.75 ppm, indicating an RNA type sugar puckering at the novel modification site favorable for hybridization to an mRNA target. The proton spectrum of the oligomer d(GACU$_3$*), where U$_3$*=3'-O-hexylamine, showed the expected 7 aromatic proton signals between 7.5 and 9.0 ppm and the anomeric proton doublet at 5.9 ppm with $J_{1',2'}$=4.4 Hz. This suggests more of a C3'-endo puckering for the 3'-O-alkylamino compounds compared to their 2' analogs. $^{31}$P NMR of these oligonucleotides showed the expected 4 and 3 signals from the internucleotide phosphate linkages for d(GAU*CT) and d(GACU*), respectively. 3'-5' Linked vs.

TABLE IIIa

| OLIGONUCLEOTIDE | MODIFICATION | DNA TARGET | RNA TARGET |
|---|---|---|---|
| A | none | 52.2 | 54.1 |
|  | 2'-aminolinker | 50.9 | 55.5 |
| B | none | 51.5 | 72.3 |
|  | 2'-aminolinker | 49.8 | 69.3 |
| C | none | NA |  |
|  | 3'-aminolinker | 42.7 | 51.7 |

The 2'-5' linkages demonstrated a higher melting temperature against an RNA target compared to a DNA target.

Example 54

Snake Venom Phosphodiesterase and Liver Homogenate Experiments on Oligonucleotide Stability The following oligonucleotides were synthesized following the procedure of Example 49.

TABLE IV

Modified Oligonucleotides synthesized to evaluate stability

| ISIS # | Sequence (5'–3') | Backbone | Chemistry |
|---|---|---|---|
| 22110 | TTT-TTT-TTT-TTT-TTT-T*T*T*-T* (SEQ ID NO: 17) | P=O | 3'-O—MOE |
| 22111 | TTT-TTT-TTT-TTT-TTT-T#T#T#-U# (SEQ ID NO: 18) | P=O | 3'-O—MOE |
| 22112 | TTT-TTT-TTT-TTT-TTT-T*T*T*-T* | P=S | 3'-O—MOE |
| 22113 | TTT-TTT-TTT-TTT-TTT-T#T#T#-U# | P=S | 3'-O—MOE |
| 22114 | TTT-TTT-TTT-TTT-TTT$_o$-T*$_o$T*$_o$T*$_o$T* | P=S/ P=O | 3'-O—MOE |
| 22115 | TTT-TTT-TTT-TTT-TTT$_o$-T#$_o$T#$_o$T#$_o$-U# | P=S/ P=O | 3'-O—MOE |

All nucleosides with an asterisk contain 3'-O-(2-methoxyethyl). All nucleosides with a # contain 2'-O-(2-methoxyethyl).

The oligonucleotides were purified following the procedure of Example 50 and analyzed for their structure.

TABLE V

Properties of Modified Oligonucleotides

| ISIS # | Sequence (5'–3')[1] | Expected Mass | Observed Mass | HPLC[2] $T_R$ (min.) | # Ods(260 nm) Purified |
|---|---|---|---|---|---|
| 22110 | TTT-TTT-TTT-TTT-TTT-T*T*T*-T* | 6314.189 | 6315.880 | 20.39 | 174 |
| 22111 | TTT-TTT-TTT-TTT-TTT-T#T#T#-U# | 6004.777 | 5997.490 | 20.89 | 147 |
| 22112 | TTT-TTT-TTT-TTT-TTT-T*T*T*-T* | 6298.799 | 6301.730 | 25.92 | 224 |
| 22113 | TTT-TTT-TTT-TTT-TTT-T#T#T#-U# | 6288.745 | 6286.940 | 24.77 | 209 |
| 22114 | TTT-TTT-TTT-TTT-TTT$_o$-T*$_o$T*$_o$T*$_o$-T* | 6234.799 | 6237.150 | 24.84 | 196 |
| 22115 | TTT-TTT-TTT-TTT-TTT$_o$-T#$_o$T#$_o$T#$_o$-U# | 6224.745 | 6223.780 | 23.30 | 340 |

[1] All nucleosides with an asterisk contain 3'-O-(2-methoxyethyl). All nucleosides with a # contain 2'-O-(2-methoxy)ethyl. [2]Conditions: Waters 600E with detector 991; Waters C4 column (3.9×300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

Example 55

3'-O-Aminopropyl Modified Oligonucleotides

Following the procedures illustrated above for the synthesis of oligonucleotides, modified 3'-amidites were used in addition to conventional amidites to prepare the oligonucleotides listed in tables VI and VII. Nucleosides used include: N6-benzoyl-3'-O-propylphthalimido-A-2'-amidite, 2'-O-propylphthaloyl-A-3'-amidite, 2'-O-methoxyethyl-thymidine-3'-amidite (RIC, Inc.), 2'-O-MOE-G-3'-amidite (RI Chemical), 2'-O-methoxyethyl-5-methylcytidine-3'-amidite, 2'-O-methoxyethyl-adenosine-3'-amidite (RI Chemical), and 5-methylcytidine-3'-amidite. 3'-propylphthalimido-A and 2'-propylphthalimido-A were used as the LCA-CPG solid support. The required amounts of the amidites were placed in dried vials, dissolved in acetonitrile (unmodified nucleosides were made into 1M solutions and modified nucleosides were 100 mg/mL), and connected to the appropriate ports on a Millipore Expedite™ Nucleic Acid Synthesis System. Solid support resin (60 mg) was used in each column for 2×1 μmole scale synthesis (2 columns for each oligo were used). The synthesis was run using the IBP-PS(1 μmole) coupling protocol for phosphorothioate backbones and CSO-8 for phosphodiesters. The trityl reports indicated normal coupling results.

After synthesis the oligonucleotides were deprotected with conc. ammonium hydroxide(aq) containing 10% of a solution of 40% methylamine (aq) at 55° C. for approximately 16 hrs. Then they were evaporated, using a Savant AS160 Automatic SpeedVac, (to remove ammonia) and filtered to remove the CPG-resin. The crude samples were analyzed by MS, HPLC, and CE. Then they were purified on a Waters 600E HPLC system with a 991 detector using a Waters C4 Prep. scale column (Alice C4 Prep.) and the following solvents: A: 50 mM TEA-Ac, pH 7.0 and B: acetonitrile utilizing the AMPREP2@ method. After purification the oligonucleotides were evaporated to dryness and then detritylated with 80% acetic acid at room temp. for approximately 30 min. Then they were evaporated. The oligonucleotides were dissolved in conc. ammonium hydroxide and run through a column containing Sephadex G-25 using water as the solvent and a Pharmacia LKB SuperFrac fraction collector. The resulting purified oligonucleotides were evaporated and analyzed by MS, CE, and HPLC.

TABLE VI

Oligonucleotides bearing Aminopropyl Substituents

| ISIS # | Sequence (5'–3')[1] | Backbone |
|---|---|---|
| 23185-1 | A*TG-CAT-TCT-GCC-CCC-AAG-GA* | P=S |
| 23186-1 | A*<u>TG</u>-<u>CA</u>T-TCT-GCC-CCC-<u>AAG</u>-<u>GA</u>* | P=S |
| 23187-1 | A*$_o$<u>T</u>$_o$<u>G</u>$_o$-<u>C</u>$_o$<u>A</u>$_s$T$_s$-T$_s$C$_s$T$_s$-G$_s$C$_s$C$_s$-C$_s$C$_s$C$_s$-<u>A</u>$_o$<u>A</u>$_o$<u>G</u>$_o$-<u>G</u>$_o$A* | P=S/P=O |
| 23980-1 | A*$_o$<u>T</u>$_o$<u>G</u>$_o$-<u>C</u>$_o$<u>A</u>$_s$T$_s$-T$_s$C$_s$T$_s$-G$_s$C$_s$C$_s$-C$_s$C$_s$C$_s$-<u>A</u>$_o$<u>A</u>$_o$<u>G</u>$_o$-<u>G</u>$_o$A* | P=S/P=O |

TABLE VI-continued

Oligonucleotides bearing Aminopropyl Substituents

| ISIS # | Sequence (5'–3')[1] | Backbone |
|---|---|---|
| 23981-1 | A*TG-CAT-TCT-GCC-CCC-AAG-GA* | P=S |
| 23982-1 | A*TG-CAT-TCT-GCC-CCC-AAG-GA* | P=S |

[1]All underlined nucleosides bear a 2'-O-methoxyethyl substituent; internucleotide linkages in PS/PO oligonucleotides are indicated by subscript >s = and >o = notations respectively; A* = 3'-aminopropyl-A; A* = 2'-aminopropyl-A; C = 5-methyl-C

TABLE VII

Aminopropyl Modified Oligonucleotides

| ISIS # | Expected Mass (g/mol) | Observed Mass (g/mol) | HPLC Retention Time(min) | CE Retention Time(min) | Crude Yield (Ods) | Final Yield (Ods) |
|---|---|---|---|---|---|---|
| 23185-1 | 6612.065 | 6610.5 | 23.19 | 5.98 | 948 | 478 |
| 23186-1 | 7204.697 | 7203.1 | 24.99 | 6.18 | 1075 | 379 |
| 23187-1 | 7076.697 | 7072.33 | 23.36 | 7.56 | 838 | 546 |
| 23980-1 | 7076.697 | 7102.31 | 23.42 | 7.16 | 984 | 373 |
| 23981-1 | 7204.697 | 7230.14 | 25.36 | 7.18 | 1170 | 526 |
| 23982-1 | 6612.065 | 6635.71 | 23.47 | 7.31 | 1083 | 463 |

Example 56

In Vivo Stability of Modified Oligonucleotides

The in vivo stability of selected modified oligonucleotides synthesized in Examples 49 and 55 was determined in BALB/c mice. Following a single i.v. administration of 5 mg/kg of oligonucleotide, blood samples were drawn at various time intervals and analyzed by CGE. For each oligonucleotide tested, 9 male BALB/c mice (Charles River, Wilmington, Mass.) weighing about 25 g were used. Following a one week acclimatization the mice received a single tail-vein injection of oligonucleotide (5 mg/kg) administered in phosphate buffered saline (PBS), pH 7.0. One retro-orbital bleed (either at 0.25, 0.5, 2 or 4 h post-dose) and a terminal bleed (either 1, 3, 8, or 24 h post-dose) were collected from each group. The terminal bleed (approximately 0.6–0.8 mL) was collected by cardiac puncture following ketamine/xylazine anasthesia. The blood was transferred to an EDTA-coated collection tube and centrifuged to obtain plasma. At termination, the liver and kidneys were collected from each mouse. Plasma and tissue homogenates were used for analysis to determine intact oligonucleotide content by CGE. All samples were immediately frozen on dry ice after collection and stored at −80C until analysis.

The CGE analysis inidcated the relative nuclease resistance of 2',5'-linked oligomers compared to ISIS 11061 (Table III, Example 51) (uniformly 2'-deoxyphosphorothioate oligonucleotide targeted to mouse c-raf). Because of the nuclease resistance of the 2',5'-linkage, coupled with the fact that 3'-methoxyethoxy substituents are present and afford further nuclease protection the oligonucleotides ISIS 17176, ISIS 17177, ISIS 17178, ISIS 17180, ISIS 17181 and ISIS 21415 were found to be more stable in plasma, while ISIS 11061 (Table III) was not. Similar observations were noted in kidney and liver tissue. This implies that 2',5'-linkages with 3'-methoxyethoxy substituents offer excellent nuclease resistance in plasma, kidney and liver against 5'-exonucleases and 3'-exonucleases. Thus oligonucleotides with longer durations of action can be designed by incorporating both the 2',5'-linkage and 3'-methoxyethoxy motifs into their structure. It was also observed that 2',5'-phosphorothioate linkages are more stable than 2',5'-phosphodiester linkages. A plot of the percentage of full length oligonucleotide remaining intact in plasma one hour following administration of an i.v. bolus of 5 mg/kg oligonucleotide is shown in. FIG. 4.

A plot of the percentage of full length oligonucleotide remaining intact in tissue 24 hours following administration of an i.v. bolus of 5 mg/kg oligonucleotide is shown in FIG. 5.

CGE traces of test oligonucleotides and a standard phosphorothioate oligonucleotide in both mouse liver samples and mouse kidney samples after 24 hours are shown in FIG. 6. As is evident from these traces, there is a greater amount of intact oliogonucleotide for the oligonucleotides of the invention as compared to the standard seen in panel A. The oligonucleotide shown in panel B included one substituent of the invention at each of the 5' and 3' ends of a phosphorothioate oligonucleotide while the phosphorothioate oligonucleotide seen in panel C included one substituent at the 5' end and two at the 3' end. The oligonucleotide of panel D includes a substituent of the invention incorporated in a 2',5' phosphodiester linkage at both its 5' and 3' ends. While less stable than the oligonucleotide seen in panels B and C, it is more stable than the full phosphorothioate standard oligonucleotide of panel A.

Example 57

Control of c-raf Message in bEND Cells Using Modified Oligonucleotides

In order to assess the activity of some of the oligonucleotides, an in vitro cell culture assay was used that measures the cellular levels of c-raf expression in bEND cells.

Cells and Reagents

The bEnd.3 cell line, a brain endothelioma, was obtained from Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.). Sterile, 12 well tissue culture plates and Facsflow solution were purchased from Becton Dickinson (Mansfield, Mass.). Ultrapure formaldehyde was purchased from Polysciences (Warrington, Pa.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM prewarmed to 37° C. Oligonucleotide were premixed with a cationic lipid (Lipofectin reagent, (GIBCO/BRL) and, serially diluted to desired concentrations and transferred on to washed cells for a 4 hour incubation at 37° C. Media was then removed and replaced with normal growth media for 24 hours for northern blot analysis of mRNA.

Northern Blot Analysis

For determination of mRNA levels by Northern blot analysis, total RNA was prepared from cells by the guanidinium isothiocyanate procedure (Monia et al., *Proc. Natl. Acad. Sci. USA*, 1996, 93, 15481–15484) 24 h after initiation of oligonucleotide treatment. Total RNA was isolated by centrifugation of the cell lysates over a CsCl cushion. Northern blot analysis, RNA quantitation and normalization to G#PDH mRNA levels were done according to a reported procedure (Dean and McKay, *Proc. Natl. Acad. Sci. USA*, 1994, 91, 11762–11766). In bEND cells the 2-,5-linked-3'-O-methoxyethyl oligonucleotides showed reduction of c-raf message activity as a function of concentration. The fact that these modified oligonucleotides retained activity promises reduced frequency of dosing with these oligonucleotides which also show increased in vivo nuclease resistance. All 2',5'-linked oligonucleotides retained the activity of parent 11061 (Table III) oligonucleotide and improved the activity even further. A graph of the effect of the oligonucleotides of the present invention on c-raf expression (compared to control) in bEND cells is shown in FIG. 7.

Example 58

Synthesis of MMI-containing Oligonucleotides a. bis-2'-O-Methyl MMI Building Blocks The synthesis of MMI (i.e., R=CH$_3$) dimer building blocks have been previously described (see, e.g., Swayze, et al., *Synlett* 1997, 859; Sanghvi, et al., *Nucleosides & Nucleotides* 1997, 16 907; Swayze, et al., *Nucleosides & Nucleotides* 1997, 16, 971; Dimock, et al., *Nucleosides & Nucleotides* 1997, 16, 1629). Generally, 5'-O-(4,4'-dimethoxytrityl)-2'-O-methyl-3'-C-formyl nucleosides were condensed with 5'-O-(N-methylhydroxylamino)-2'-O-methyl-3'-O-TBDPS nucleosides using 1 equivalent of BH$_3$ pyridine/1 equivalent of pyridinium para-toluene sulfonate (PPTS) in 3:1 MeOH/THF. The resultant MMI dimer blocks were then deprotected at the lower part of the sugar with 15 equivalents of Et$_3$N-2HF in THF. Thus the T*G$^{iBu}$ dimer unit was synthesized and phosphitylated to give T*G(MMI) phosphoramidite. In a similar fashion, A$^{BZ}$*T(MMI) dimer was synthesized, succinylated and attached to controlled pore glass.

b. Oligonucleotide Synthesis

Oligonucleotides were synthesized on a Perseptive Biosystems Expedite 8901 Nucleic Acid Synthesis System. Multiple 1-μmol syntheses were performed for each oligonucleotide. A*$_{MMI}$T solid support was loaded into the column. Trityl groups were removed with trichloroacetic acid (975 μL over one minute) followed by an acetonitrile wash. The oligonucleotide was built using a modified thioate protocol. Standard amidites were delivered (210 μL) over a 3 minute period in this protocol. The T*$_{MMI}$G amidite was double coupled using 210 μL over a total of 20 minutes. The amount of oxidizer, 3H-1,2-benzodithiole-3-one-1,1-dioxide (Beaucage reagent, 3.4 g Beaucage reagent/200 mL acetonitrile), was 225 μL (one minute wait step). The unreacted nucleoside was capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. After the synthesis, the contents of the synthesis cartridge (1 μmole) were transferred to a Pyrex vial and the oligonucleotide was cleaved from the controlled pore glass (CPG) using 5 mL of 30% ammonium hydroxide (NH$_4$OH) for. approximately 16 hours at 55° C.

C. Oligonucleotide Purification

After the deprotection step, the samples were filtered from CPG using Gelman 0.45 μm nylon acrodisc syringe filters. Excess NH$_4$OH was evaporated away in a Savant AS160 automatic SpeedVac. The crude yield was measured on a Hewlett Packard 8452A Diode Array Spectrophotometer at 260 nm. Crude samples were then analyzed by mass spectrometry (MS) on a Hewlett Packard electrospray mass spectrometer. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Fractions containing the desired product (retention time=41 min. for DMT-ON-16314; retention time=42.5 min. for DMT-ON-16315) were collected and the solvent was dried off in the SpeedVac. Oligonucleotides were detritylated in 80% acetic acid for approximately 60 minutes and lyophilized again. Free trityl and excess salt were removed by passing detritylated oligonucleotides through Sephadex G-25 (size exclusion chromatography) and collecting appropriate samples through a Pharmacia fraction collector. The solvent was again evaporated away in a SpeedVac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm.

The synthesized oligonucleotides and their physical characteristics are shown, respectively, in Tables VIII and IX. All nucleosides with an asterisk contain MMI linkage.

TABLE VIII

ICAM-1 Oligonucleotides Containing MMI Dimers Synthesized for in Vivo Nuclease and Pharmacology Studies.

| ISIS # | Sequence (5'–3') | Backbone | 2'-Chemistry |
|---|---|---|---|
| 16314 | TGC ATC CCC CAG GCC ACC A*T (SEQ ID NO: 19) | P=S, MMI | Bis-2'-OMe-MMI, 2'-H |
| 16315 | T*GC ATC CCC CAG GCC ACC A*T | P=S, MMI | Bis-2'-OMe-MMI, 2'-H |
| 3082 mismatch | TGC ATC CCC CAG GCG ACC AT | P=S | 2'-H, single |
| 13001 | TGC ATC CCC CAG GCC ACC AT | P=S | 2'-H |

TABLE IX

Physical Characteristics of MMI Oligomers
Synthesized for Pharmacology, and In Vivo Nuclease Studies

| ISIS # Retn. (min) | Sequence (5'–3') | Expected Mass (g) | Observed Mass (g) | HPLC Time |
|---|---|---|---|---|
| 16314 | TGC ATC CCC CAG GCC ACC A*T | 6295 | 6297 | 23.9 |
| 16315 | T*G C ATC CCC CAG GCC ACC A*T | 6302 | 6303 | 24.75 |

HPLC Conditions: Waters 600E with detector 991; Waters C4 column (3.9×300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

Example 59

Synthesis of Sp Terminal Oligonucleotide a. 3'-t-Butyldiphenylsilyl-thymidine (1)

5'-O-Dimethoxytritylthymidine is silylated with 1 equivalent of t-butyldiphenylsilyl chloride (TBDPSCl) and 2 equivalents of imidazole in DMF solvent at room temperature. The 5'-protecting group is removed by treating with 3% dichloracetic acid in $CH_2Cl_2$.

b. 5'-O-Dimethoxytrityl-thymidin-3'-O-yl-N,N-diisopropylamino(S-pivaloyl-2-mercaptoethoxy) phosphoramidite (2)

5'-O-Dimethoxytrityl thymidine is treated with bis-(N,N-diisopropylamino)-S-pivaloyl-2-mercaptoethoxy phosphoramidite and tetrazole in $CH_2Cl_2/CH_3CN$ as described by Guzaev et al., Bioorganic & Medicinal Chemistry Letters 1998, 8, 1123) to yield the title compound.

c. 5'-O-Dimethoxytrityl-2'-deoxy-adenosin-3'-O-yl-N,N-diisopropylamino(S-pivaloyl-2-mercapto Ethoxy) phosphoramidite (3)

5'-O-Dimethoxytrityl-N-6-benzoyl-2'-deoxy-adenosine is phosphitylated as in the previous example to yield the desired amidite.

d. 31-O-t-Butyldiphenylsilyl-2'-deoxy-$N_2$-isobutyryl-guanosine (4)

5'-O-Dimethoxytrityl-2'-deoxy-$N_2$-isobutyryl-guanisine is silylated with TBDPSC1 and imidazole in DMF. The 5'-DMT is then removed with 3% DCA in $CH_2Cl_2$.

e. $T_{(Sp)}G$ Dimers and $T_{(S)}$ Phosphoramidite

Compounds 4 and 2 are condensed (1:1 equivalents) using 1H-tetrazole in $CH_3CN$ solvent followed by sulfurization employing Beaucage reagent (see, e.g., Iyer, et al., J. Org. Chem. 1990, 55, 4693). The dimers (TG) are separated by column chromatography and the silyl group is deprotected using t-butyl ammonium fluoride/THF to give Rp and Sp dimers of $T_SG$. Small amounts of these dimers are completely deprotected and treated with either P1 nuclease or snake venom phosphodiesterase. The R isomer is resistant to P1 nuclease and hydrolyzed by SVPD. The S isomer is resistant to SVPD and hydrolyzed P1 nuclease. The Sp isomer of the fully protected $T_SG$ dimer is phosphitylated to give DMT-T-Sp-G-phosphoramidite.

f. $A_ST$ Dimers and Solid Support Containing $A_{SP}T$ Dimer

Compounds 3 and 1 are condensed using 1H-tetrazole in $CH_3CN$ solvent followed by sulfurization to give AT dimers. The dimers are separated by column chromatography and the silyl group is deprotected with TBAF/THF. The configurational assignments are done generally as in the previous example. The Sp isomer is then attached to controlled pore glass according to standard procedures to give DMT-$A_{SP}$-T-CPG oligomerization with chirally pure Sp dimer units at the termini.

g. Oligonucleotide Synthesis

The oligonucleotide having the sequence T*GC ATC CCC CAG GCC ACC A*T is synthesized, where T*G and A*T represent chiral Sp dimer blocks described above. DMT-$A_{SP}$-T-CPG is taken in the synthesis column and the next 16b residues are built using standard phosphorothioate protocols and 3H-1,2-benzodithiol-3-one 1,1 dioxide as the sulfurizing agent. After building this 18 mer unit followed by final detritylation, the chiral Sp dimer phosphoramidite of 5'-DMT-$T_{SP}$-G amidite is coupled to give the desired antisense oligonucleotide. This compound is then deprotected in 30% $NH_4OH$ over 16 hours and the oligomer purified in HPLC and desalted in Sephader G-25 column. The final oligomer has Sp configuration at the 5'-terminus and 3'-terminus and the interior has diastereomeric mixture of Rp and Sp configurations.

Example 60

Evaluation of In Vivo Stability of MMI Capped Oligonucleotides Mouse Experiment Procedures For each oligonucleotide tested, 9 male BALB/c mice (Charles River, Wilmington, Mass.), weighing about 25 g was used (Crooke et al., J. Pharmacol. Exp. Ther., 1996, 277, 923). Following a 1-week acclimation, mice received a single tail vein injection of oligonucleotide (5 mg/kg) administered in phosphate buffered saline (PBS), pH 7.0 One retro-orbital bleed (either 0.25, 0.5, 2 or 4 lv post dose) and a terminal bleed (either 1, 3, 8 or 24 h post dose) were collected from each group. The terminal bleed (approximately 0.6–0.8 mL) was collected by cardiac puncture following ketamine/xylazine anesthesia. The blood was transferred to an EDTA-coated collection tube and centrifuged to obtain plasma. At termination, the liver and kidneys were collected from each mouse. Plasma and tissues homogenates were used for analysis for determination of intact oligonucleotide content by CGE. All samples were immediately frozen on dry ice after collection and stored at −80° C. until analysis.

The capillary gel electrophoretic analysis indicated the relative nuclease resistance of MMI capped oligomers compared to ISIS 3082 (uniform 2'-deoxy phosphorothioate). Because of the resistance of MMI linkage to nucleases, the compound 16314 was found to be stable in plasma while 3082 was not. However, in kidney and liver, the compound 16314 also showed certain amount of degradation. This implied that while 3'-exonuclease is important in plasma, 5'-exonucleases or endonucleases may be active in tissues. To distinguish between these two possibilities, the data from 16315 was analyzed. In plasma as well as in tissues, (liver and kidney) the compound was stable in various time points. (1, 3 and 24 hrs.). The fact that no degradation was detected proved that 5'-exonucleases and 3'-exonuclease are prevalent in tissues and endonucleases are not active. Furthermore, a single linkage (MMI or Sp thioate linkage) is sufficient as a gatekeeper against nucleases.

Control of ICAM-1 Expression Cells and Reagents

The bEnd.3 cell line, a brain endothelioma, was the kind gift of Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.).

Sterile, 12 well tissue culture plates and Facsflow solution were purchased from Becton Dickinson (Mansfield, Mass.). Ultrapure formaldehyde was purchased from Polysciences (Warrington, Pa.). Recombinant human TNF-a was purchased from R&D Systems (Minneapolis, Minn.). Mouse interferon-γ was purchased from Genzyme (Cambridge, Mass.). Fraction V, BSA was purchased from Sigma (St. Louis, Mo.). The mouse ICAM-1-PE, VCAM-1-FITC, hamster IgG-FITC and rat IgG$_{2a}$-PE antibodies were purchased from Pharmingen (San Diego, Calif.). Zeta-Probe nylon blotting membrane was purchased from Bio-Rad (Richmond, Calif.). QuickHyb solution was purchased from Stratagene (La Jolla, Calif.). A cDNA labeling kit, Prime-a-Gene, was purchased from ProMega (Madison, Wis.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM pre-warmed to 37° C. Oligonucleotide was premixed with Opti-MEM, serially diluted to desired concentrations and transferred onto washed cells for a 4 hour incubation at 37° C. Media was removed and replaced with normal growth media with or without 5 ng/mL TNF-α and 200 U/mL interferon-γ, incubated for 2 hours for northern blot analysis of mRNA or overnight for flow cytometric analysis of cell surface protein expression.

Flow Cytometry

After oligonucleotide treatment, cells were detached from the plates with a short treatment of trypsin-EDTA (1–2 min.). Cells were transferred to 12×75 mm polystyrene tubes and washed with 2% BSA, 0.2% sodium azide in D-PBS at 4° C. Cells were centrifuged at 1000 rpm in a Beckman GPR centrifuge and the supernatant was then decanted. ICAM-1, VCAM-1 and the control antibodies were added at 1 ug/mL in 0.3 mL of the above buffer. Antibodies were incubated with the cells for 30 minutes at 4° C. in the dark, under gentle agitation. Cells were washed again as above and then resuspended in 0.3 mL of FacsFlow buffer with 0.5% ultrapure formaldehyde. Cells were analyzed on a Becton Dickinson FACScan. Results are expressed as percentage of control expression, which was calculated as follows: [((CAM expression for oligonucleotide-treated cytokine induced cells)–(basal CAM expression))/((cytokine-induced CAM expression)–(basal CAM expression))]×100. For the experiments involving cationic lipids, both basal and cytokine-treated control cells were pretreated with Lipofectin for 4 hours in the absence of oligonucleotides.

The results reveal the following: 1) Isis 3082 showed an expected dose response (25–200 nM); 2) Isis 13001 lost its ability to inhibit ICAM-1 expression as expected from a mismatch compound, thus proving an antisense mechanism; 3) 3'-MMI capped oligomer 16314 improved the activity of 3082, and at 200 nM concentration, nearly twice as active as 3082; 4) 5'- and 3'-MMI capped oligomer is the most potent compound and it is nearly 4 to 5 times more efficacious than the parent compound at 100 and 200 nM concentrations. Thus, improved nuclease resistance increased the potency of the antisense oligonucleotides.

Example 61

Control of H-ras Expression

Antisense oligonucleotides targeting the H-ras message were tested for their ability to inhibit production of H-ras mRNA in T-24 cells. For these test, T-24 cells were plated in 6-well plates and then treated with various escalating concentrations of oligonucleotide in the presence of cationic lipid (Lipofectin, GIBCO) at the ratio of 2.5 μg/ml Lipofectin per 100 nM oligonucleotide. Oligonucleotide treatment was carried out in serum free media for 4 hours. Eighteen hours after treatment the total RNA was harvested and analyzed by northern blot for H-ras mRNA and control gene G3PDH. The data is presented in FIGS. 8 and 9 in bar graphs as percent control normalized for the G3PDH signal. As can be seen, the oligonucleotide having a single MMI linkage in each of the flank regions showed significant reduction of H-ras mRNA.

Example 62

5-Lipoxygenase Analysis and Assays

A. Therapeutics

For therapeutic use, an animal suspected of having a disease characterized by excessive or abnormal supply of 5-lipoxygenase is treated by administering a compound of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotides of the invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30 to about 50° C. The cleaved 5-lipoxygenase RNA can be analyzed by agarose gel electrophoresis and hybridization with radiolabeled DNA probes or by other standard methods.

C. Diagnostics

The oligonucleotides of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA. Tissue samples can be homogenized, and RNA extracted by standard methods. The crude homogenate or extract can be treated for example to effect cleavage of the target RNA. The product can then be hybridized to a solid support which contains a bound oligonucleotide complementary to a region n the 5' side of the cleavage site. Both the normal and normal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotides which interfere with 5-lipoxygenase synthesis in these cells.

A second test system for oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells. A direct effect which oligonucleotides can exert on intact cells and which can be easily be quantitated is specific inhibition of 5-lipoxygenase protein synthesis. To perform this technique, cells can be labeled with $^{35}$S-methionine (50 $\mu$Ci/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of the macromolecules of the invention for 48 hours would reduce immunoprecipitated 5-lipoxygenase by 5%, 25% and 75% of control, respectively. Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/mL phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 $\mu$M, 10 $\mu$M, and 30 $\mu$M would be as follows. Control cells oxidize 200 $\mu$mol arachidonic acid/5 min/$10^6$ cells. Cells treated with 1 $\mu$M, 10 $\mu$M, and 30 $\mu$M of an effective oligonucleotide would oxidize 195 $\mu$mol, 140 pmol, and 60 $\mu$mol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. Purified 5-lipoxygenase (25 ng) is bound to the microtiter plates overnight at 4° C. The wells are blocked for 90 min with 5% goat serum diluted in 20 mM Tris!HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 $\mu$L in the microtiter wells for 90 min. The antibodies are prepared by immunizing rabbits with purified human recombinant 5-lipoxygenase. The wells are washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labeled second antibody determined by development with tetramethylbenzidine.

Predicted results from such an assay using a 30 mer oligonucleotide at 1 $\mu$M, 10 $\mu$M, and 30 $\mu$M would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells (2×$10^5$ cells/mL) will be treated with increasing concentrations of the macromolecule for 48–72 hours in the presence of 1.3% DMSO. The cells are washed and resuspended at a concentration of 2×$10^6$ cell/mL in Dulbecco's phosphate buffered saline containing 1% delipidated bovine serum albumin. Cells are stimulated with 10 $\mu$M calcium ionophore A23187 for 15 min and the quantity of LTB4 produced from 5×$10^5$ cell determined by radioimmunoassay as described by the manufacturer.

Using this assay the following results would likely be obtained with an oligonucleotide directed to the 5-LO mRNA. Cells will be treated for 72 hours with either 1 $\mu$M, 10 $\mu$M or 30 $\mu$M of the macromolecule in the presence of 1.3% DMSO. The quantity of $LTB_4$ produced from 5×$10^5$ cells would be expected to be about 75 $\mu$g, 50 $\mu$g, and 35 pg, respectively with untreated differentiated cells producing 75 $\mu$g $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotides will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

Example 63

5'-O-DMT-2'-Deoxy-2'-methylene-5-methyl Uridine-3'-(2-cyanoethyl-N,N-diisoproppyl) phosphoramidite 2'-Deoxy-2'-methylene-3',5'-O-(tetraisopropyl disiloxane-1,3,diyl)-5-methyl uridine is synthesized following the procedures reported for the corresponding uridine derivative (Hansske, F.; Madej, D.; Robins, M. J. *Tetrahedron* (1984) 40, 125; Matsuda, A.; Takenusi, K.; Tanaka, S.; Sasaki, T.; Ueda, T. *J. Med. Chem.* (1991) 34, 812; See also Cory, A. H.; Samano, V.; Robins, M. J.; Cory, J. G. 2'-Deoxy-2'-methylene derivatives of adenosine, guanosine, tubercidin, cytidine and uridine as inhibitors of L1210 cell growth in culture. Biochem. Pharmacol. (1994), 47(2), 365–71.)

It is treated with 1M TBAF in THF to give 2'-deoxy-2'-methylene-5-methyl uridine. It is dissolved in pyridine and treated with DMT-Cl and stirred to give the 5'-O-DMT-2'-deoxy-2'-methylene-5-methyl uridine. This compound is treated with 2-cyanoethyl-N,N-diisopropyl phosphoramidite and diisopropylaminotetrazolide. In a similar manner the corresponding N-6 benzoyl adenosine, N-4-benzoyl cytosine, N-2-isobutyryl guanosine phosphoramidite derivatives are synthesized.

Example 63

Synthesis of 3'-O-4'-C-Methyleneribonucleoside

5'-O-DMT-3'-O-4'-C-methylene uridine and 5-methyl uridine are synthesized and phosphitylated according to the procedure of Obika et al. (Obika et al. *Bioorg. Med. Chem. Lett.* (1999) 9, 515–158). The amidites are incorporated into oligonucleotides using the protocols described above.

Example 64

Synthesis of 2'-Methylene Phosphoramidites

5'-O-DMT-2'-(methyl)-3'-O-(2-cyanoethyl-N,N-diisopropylamine)-5-methyluridine-phosphoramidite, 5'-O-DMT-2'-(methyl)-N-6-benzoyl adenosine (3'-O-2-cyanoethyl-N,N-diisopropylamino)phosphoramidite, 5'-O-DMT-2'-(methyl)-N2-isoburytyl guanosine-3'-O-(2-cyanoethyl-N,N-diisopropylamino)phosphoramidite and 5'-O-DMT-2'-(methyl)-N-4-benzoyl cytidine-3'-O-(2-cyanoethyl-N,N-diisopropylamino)phosphoramidites were obtained by the phosphitylation of the corresponding nucleosides. The nucleosides were synthesized according to the procedure described by Iribarren, Adolfo M.; Cicero, Daniel O.; Neuner, Philippe J. Resistance to degradation by nucleases of (2'S)-2'-deoxy-2'-C-methyloligonucleotides, novel potential antisense probes. Antisense Res. Dev., (1994), 4(2), 95–8; Schmit, Chantal; Bevierre, Marc-Olivier; De Mesmaeker, Alain; Altmann, Karl-Heinz. "The effects of 2'- and 3'-alkyl substituents on oligonucleotide hybridization and stability". Bioorg. Med. Chem. Lett. (1994), 4(16), 1969–74.

The phosphitylation is carried out by using the bisamidite procedure.

Example 65

Synthesis of 2'-S-Methyl Phosphoramidites

5'-O-DMT-2'-S-(methyl)-3'-O-(2-cyanoethyl-N,N-diisopropylamine)-5-methyl uridine-phosphoramidite, 5'-O-DMT-2'-S(methyl)-N-6-benzoyl adenosine (3'-O-2-cyanoethyl-N,N-diisopropylamino)phosphoramidite, 5'-O-DMT-2'-S-(methyl)-N2-isoburytyl guanosine-3'-O-(2-cyanoethyl-N,N-diisopropylamino)phosphoramidite and 5'-O-DMT-2'-S-(methyl)-N-4-benzoyl cytidine-3'-O-(2-cyanoethyl-N,N-diisopropylamino)phosphoramidites were obtained by the phosphitylation of the corresponding nucleosides. The nucleosides were synthesized according to the procedure described by Fraser et al. (Fraser, A.; Wheeler, P.; Cook, P. D.; Sanghvi, Y. S. *J. Heterocycl. Chem.* (1993) 31, 1277–1287). The phosphitylation is carried out by using the bisamidite procedure.

Example 66

Synthesis of 2'-O-Methyl-β-D-arabinofuranosyl Compounds

2'-O-Methyl-β-D-arabinofuranosyl-thymidine containing oligonucleotides were synthesized following the procedures of Gotfredson et. al. (Gotfredson, C. H. et. al. *Tetrahedron Lett.* (1994) 35, 6941–6944; Gotfredson, C. H. et. al. *Bioorg. Med. Chem.* (1996) 4, 1217–1225). 5'-O-DMT-2'-ara-(O-methyl)-3'-O-(2-cyanoethyl-N,N-diisopropylamine)-5-methyl uridine-phosphoramidite, 5'-O-DMT-2'-ara-(O-methyl)-N-6-benzoyl adenosine (3'-O-2-cyanoethyl-N,N-diisopropylamino)phosphoramidite, 5'-O-DMT-2'-ara-(O-methyl)-N2-isoburytyl guanosine-3'-O-(2-cyanoethyl-N,N-diisopropylamino)phosphoramidite and 5'-O-DMT-2'-ara-(O-methyl)-N-4-benzoyl cytidine-3'-O-(2-cyanoethyl-N,N-diisopropylamino)phosphoramidites are obtained by the phosphitylation of the corresponding nucleosides. The nucleosides are synthesized according to the procedure described by Gotfredson, C. H. et. al. *Tetrahedron Lett.* (1994) 35, 6941–6944; Gotfredson, C. H. et. al. *Bioorg. Med. Chem.* (1996) 4, 1217–1225. The phosphitylation is carried out by using the bisamidite procedure.

Example 67

Synthesis of 2'-Fluoro-β-D-arabinofuranosyl Compounds

2'-Fluoro-β-D-arabinofuranosyl oligonucleotides are synthesized following the procedures by Kois, P. et al., Nucleosides Nucleotides 12, 1093,1993 and Damha et al., J. Am. Chem. Soc., 120, 12976,1998 and references sited therein. 5'-O-DMT-2'-ara-(fluoro)-3'-O-(2-cyanoethyl-N,N-diisopropylamine)-5-methyl uridine-phosphoramidite, 5'-O-DMT-2'-ara-(fluoro)-N-6-benzoyl adenosine (3'-O-2-cyanoethyl-N,N-diisopropylamino)phosphoramidite, 5'-O-DMT-2'-ara-(fluoro)-N2-isoburytyl guanosine-3'-O-(2-cyanoethyl-N,N-diisopropylamino)phosphoramidite and 5'-O-DMT-2'-ara-(fluoro)-N-4-benzoyl cytidine-3'-O-(2-cyanoethyl-N,N-diisopropylamino)phosphoramidites are obtained by the phosphitylation of the corresponding nucleosides. The nucleosides are synthesized according to the procedure described by Kois, P. et al., Nucleosides Nucleotides 12, 1093, 1993 and Damha et al., J. Am. Chem. Soc., 120, 12976, 1998. The phosphitylation is carried out by using the bisamidite procedure.

Example 68

Synthesis of 2'-Hydroxyl-β-D-arabinofuranosyl Compounds

2'-Hydroxyl-β-D-arabinofuranosyl oligonucleotides are synthesized following the procedures by Resmini and Pfleiderer Helv. Chim. Acta, 76, 158, 1993; Schmit et al., Bioorg. Med. Chem. Lett. 4, 1969, 1994 Resmini, M.; Pfleiderer, W. Synthesis of arabinonucleic acid (tANA). Bioorg. Med. Chem. Lett. (1994), 16, 1910.; Resmini, Matthias; Pfleiderer, W. Nucleosides. Part LV. Efficient synthesis of arabinoguanosine building blocks (Helv. Chim. Acta, (1994), 77, 429–34; and Damha et al., J. Am. Chem. Soc., 1998, 120, 12976, and references sited therein).

5'-O-DMT-2'-ara-(hydroxy)-3'-O-(2-cyanoethyl-N,N-diisopropylamine)-5-methyl uridine-phosphoramidite, 5'-O-DMT-2'-ara-(hydroxy)-N-6-benzoyl adenosine (3'-O-2-cyanoethyl-N,N-diisopropylamino)phosphoramidite, 5'-O-DMT-2'-ara-(hydroxy)-N2-isoburytyl guanosine-3'-O-(2-cyanoethyl-N,N-diisopropylamino)phosphoramidite and 5'-O-DMT-2'-ara-(hydroxy)-N-4-benzoyl cytidine-3'-O-(2-cyanoethyl-N,N-diisopropylamino)phosphoramidites are obtained by the phosphitylation of the corresponding nucleosides. The nucleosides are synthesized according to the procedure described by Kois, P. et al., Nucleosides Nucleotides 12, 1093,1993 and Damha et al., J. Am. Chem. Soc., 120, 12976,1998. The phosphitylation is carried out by using the bisamidite procedure.

Example 69

Synthesis of Difluoromethylene Compounds

5'-O-DMT-2'-deoxy-2'-difluoromethylene-5-methyluridine-3'-(2-cyanoethyl-N,N-diisopropyl phosphoramidite), 5'-O-DMT-2'-deoxy-2'-difluoromethylene-N-4-benzoyl-cytidine, 5'-O-DMT-2'-deoxy-2'-diflyoromethylene-N-6-benzoyl adenosine, and 5'-O-DMT-2'-deoxy-2'-difluoroethylene-$N_2$-isobutyryl guanosine are synthesized following the protocols described by Usman et. al. (U.S. Pat. No. 5,639,649, Jun. 17, 1997).

Example 70

Synthesis of 5'-O-DMT-2'-Deoxy-2'-β-(O-acetyl)-2'-α-methyl-N6-benzoyl-adenosine-3'-(2-cyanoethyl-N, N-diisopropyl Phosphoramidite 5'-O-DMT-2'-deoxy-2'-β-(OH)-2'-α-methyl-adenosine is synthesized from the compound 5'-3'-protected-2'-keto-adenosine (Rosenthal, Sprinzl and Baker, Tetrahedron Lett. 4233, 1970; see also Nucleic acid related compounds. A convenient procedure for the synthesis of 2'- and 3'-ketonucleosides is shown Hansske et al., Dep. Chem., Univ. Alberta, Edmonton, Can., Tetrahedron Lett. (1983), 24(15), 1589–92.) by Grigand addition of MeMgI in THF solvent, followed by seperation of the isomers. The 2-β-(OH) is protected as acetate. 5'-3'-acetal group is removed, 5'-position dimethoxy, tritylated, N-6 position is benzoylated and then 3'-position is phosphitylated to give 5'-O-DMT-2'-deoxy-2'-β-(O-acetyl)-2'-α-methyl-N6-benzoyl-adenosine-3'-(2-cyanoethyl-N,N-diisopropyl) phosphoramidite.

Example 71

Synthesis of 5'-O-DMT-2'-α-Ethynyl-N6-benzoyl-adenosine-3'-(2-cyanoethyl-N,N-diisopropyl Phosphoramidite 5'-O-DMT-2'-deoxy-2'-β-(OH)-2'-α-ethynyl-adenosine is synthesized from the compound 5'-3'-protected-2'-keto-adenosine (Rosenthal, Sprinzl and Baker, Tetrahedron Lett. 4233, 1970) by Grigand addition of Ethynyl-MgI in THF solvent, followed by seperation of the isomers. The 2'-β-(OH) is removed by Robins' deoxygenation procedure (Robins et al., J. Am. Chem. Soc. (1983), 105, 4059–65. 5'-3'-acetal group is removed, 5'-position dimethoxytritylated, N-6 position is benzoylated and then 3'-position is phosphitylated to give the title compound.

Example 72

2'-O-(Guaiacolyl)-5-methyluridine

2-Methoxyphenol (6.2 g, 50 mmol) was slowly added to a solution of borane in tetrahydrofuran (1 M, 10 mL, 10 mmol) with stirring in a 100 mL bomb. Hydrogen gas evolved as the solid dissolved O-2,2'-anhydro-5-methyluridine (1.2g, 5 mmol), and sodium bicarbonate (2.5 mg) were added and the bomb was sealed, placed in an oil bath and heated to 155° C. for 36 hours. The bomb was cooled to room temperature and opened. The crude solution was concentrated and the residue partitioned between water (200 mL) and hexanes (200 mL). The excess phenol was extracted into hexanes. The aqueous layer was extracted with ethyl acetate (3×200 mL) and the combined organic layer was washed once with water, dried over anhydrous sodium sulfate and concentrated. The residue was purified by silica gel flash column chromatography using methanol-:methylene chloride (1/10, v/v) as the eluent. Fractions were collected and the target fractions were concentrated to give 490 mg of pure product as a white solid. Rf=0.545 in $CH_2Cl_2/CH_3OH$ (10:1). MS/ES for $C_{17}H_2ON_2O_7$, 364.4; Observed 364.9.

Example 73

5'-Dimethoxytrityl-2'-O-(2-methoxyphenyl)-5-methyluridine-3'-O-(2-cyanoethyl-N,N-diisopropylamino)phosphoramidite 2'-O-(guaiacolyl)-5-methyl-uridine is treated with 1.2 equivalents of dimethoxytrityl chloride (DMT-Cl) in pyridine to yield the 5'-O-dimethoxy tritylated nucleoside. After evaporation of the pyridine and work up ($CH_2Cl_2$/saturated $NaHCO_3$ solution) the compound is purified in a silica gel column. The 5'-protected nucleoside is dissolved in anhydrous methylene chloride and under argon atmosphere, N,N-diisopropylaminohydrotetrazolide (0.5 equivalents)

and bis-N,N-diisopropylamino-2-cyanoethyl-phosphoramidite (2 equivalents) are added via syringe over 1 min. The reaction mixture is stirred under argon at room temperature for 16 hours and then applied to a silica column. Elution with hexane:ethylacetate (25:75) gives the title compound.

Example 74

5'-Dimethoxytrityl-2'-O-(2-methoxyphenyl)-5-methyluridine-3'-O-succinate

The 5'-protected nucleoside from Example 73 is treated with 2 equivalents of succinic anhydride and 0.2 equivalents of 4-N,N-dimethylaminopyridine in pyridine. After 2 hours the pyridine is evaporated, the residue is dissolved in $CH_2Cl_2$ and washed three times with 100 mL of 10% citric acid solution. The organic layer is dried over anhydrous $MgSO_4$ to give the desired succinate. The succinate is then attached to controlled pore glass (CPG) using established procedures (Pon, R. T., Solid phase supports for oligonucleotide synthesis, in *Protocols for Oligonucleotides and Analogs*, S. Agrawal (Ed.), Humana Press: Totawa, N.J., 1993, 465–496).

Example 75

5'-Dimethoxytrityl-2'-O-(trans-2-methoxycyclohexyl)-5-methyl Uridine

2'-3'-O-Dibutylstannyl-5-methyl uridine (Wagner et al., *J. Org. Chem.*, 1974, 39, 24) is alkylated with trans-2-methoxycyclohexyl tosylate at 70° C. in DMF. A 1:1 mixture of 2'-O- and 3'-O-(trans-2-methoxycyclohexyl)-5-methyluridine is obtained in this reaction. After evaporation of the DMF solvent, the crude mixture is dissolved in pyridine and treated with dimethoxytrityl-chloride (DMT-Cl) (1.5 equivalents). The resultant mixture is purified by silica gel flash column chromatography to give the title compound.

Example 76

5'-Dimethoxytrityl-2'-O-(trans-2-methoxycyclohexyl)-5-methyluridine-3'-O-(2-cyanoethyl-N,N-diisopropylamino)phosphoramidite 5'-Dimethoxytrityl-2'-O-(trans-2-methoxycyclohexyl)-5-methyl uridine is phosphitylated according to the procedure described above to give the required phosphoramidite.

Example 77

5'-Dimethoxytrityl-2'-O-(trans-2-methoxycyclohexyl)-5-methyluridine-3'-O-(succinyl-amino) CPG 5'-Dimethoxytrityl-2'-O-(trans-2-methoxycyclohexyl)-5-methyl uridine is succinylated and attached to controlled pore glass to give the solid support bound nucleoside.

Example 78 trans-2-Ureido-cyclohexanol

Trans-2-amino-cyclohexanol (Aldrich) is treated with triphosgene in methylene chloride (1/3 equivalent). To the resulting solution, excess ammonium hydroxide is added to give after work up the title compound.

Example 79

2'-O-(trans-2-Uriedo-cyclohexyl)-5-methyl Uridine

Trans-2-uriedo-cyclohexanol (50 mmol) is added to a solution of borane in tetrahydrofuran (1 M, 10 mL, 10 mmol) while stirring in a 10 mL bomb. Hydrogen gas evolves as the reactant dissolves. O2,2'-Anhydro-5-methyluridine (5 mmol) and sodium bicarbonate (2.5 mg) are added to the bomb and sealed. Then it is heated to 140 for 72 hrs. The bomb is cooled to room temperature and opened. The crude material was worked up as illustrated above followed by purification by silica gel flash column chromatography to give the title compound.

Example 80

5'-O-(Dimethoxytrityl)-2'-O-(trans-2-uriedo-cyclohexyl) 3'-O-(2-Cyanoethyl, N,N,-Diisopropyl) uridine Phosphoramidite 2'-O-(trans-2-uriedo-cyclohexyl)-5-methyl uridine tritylated at the 5'-OH and phosphitylated at the 3'-OH following the procedures illustrated in example 2 to give the title compound.

Example 81

5'-O-Dimethoxytrityl-2'-O-(trans-2-uriedo-cyclohexyl)-5-methyl-3'-O-(succinyl)-amino CPG Uridine 5'-O-dimethoxytrityl-2'-O-(trans-2-uriedo-cyclohexyl)-5-methyl uridine is succinylated and attached to CPG as illustrated above.

Example 82

2'-O-(trans-2-Methoxy-cyclohexyl)adenosine

Trans-2-methoxycyclopentanol, trans-2-methoxy-cylcohexanol, trans-2-methoxy-cyclopentyl tosylate and trans-2-methoxy-cyclohexyl tosylate are prepared according to reported procedures (Roberts, D. D., Hendrickson, W., *J. Org. Chem.*, 1967, 34, 2415–2417; *J. Org. Chem.*, 1997, 62, 1857–1859). A solution of adenosine (42.74 g, 0.16 mol) in dry dimethylformamide (800 mL) at 5° C. is treated with sodium hydride (8.24 g, 60% in oil prewashed thrice with hexanes, 0.21 mol). After stirring for 30 min, trans-2-methoxycyclohexyl tosylate (0.16 mol) is added over 20 minutes at 5° C. The reaction is stirred at room temperature for 48 hours, then filtered through Celite. The filtrate is concentrated under reduced pressure followed by coevaporation with toluene (2×100 mL) to give the title compound.

Example 83

$N^6$-Benzoyl-2'-O-(trans-2-methoxycyclohexyl) adenosine

A solution of 2'-O-(trans-2-methoxy-cyclohexyl) adenosine (0.056 mol) in pyridine (100 mL) is evaporated under reduced pressure to dryness. The residue is redissolved in pyridine (560 mL) and cooled in an ice water bath. Trimethylsilyl chloride (36.4 mL, 0.291 mol) is added and the reaction is stirred at 5° C. for 30 minutes. Benzoyl chloride (33.6 mL, 0.291 mol) is added and the reaction is allowed to warm to 25° C. for 2 hours and then cooled to 5° C. The reaction is diluted with cold water (112 mL) and after stirring for 15 min, concentrated ammonium hydroxide (112 mL). After 30 min, the reaction is concentrated under reduced pressure (below 30° C.) followed by coevaporation with toluene (2×100 mL). The residue is dissolved in ethyl acetate-methanol (400 mL, 9:1) and the undesired silyl by-products are removed by filtration. The filtrate is concentrated under reduced pressure and purified by silica gel flash column chromatography (800 g, chloroform-methanol 9:1). Selected fractions are combined, concentrated under reduced pressure and dried at 25° C./0.2 mmHg for 2 h to give the title compound.

Example 84

N[6]-Benzoyl-5'-O-(dimethoxytrityl)-2'-O-(trans-2-methoxycyclohexyl)adenosine

A solution of N[6]-benzoyl-2'-O-(trans-2-methoxycyclohexyl)adenosine (0.285 mol) in pyridine (100 mL) is evaporated under reduced pressure to an oil. The residue is redissolved in dry pyridine (300 mL) and 4,4'-dimethoxytriphenylmethyl chloride (DMT-Cl, 10.9 g, 95%, 0.31 mol) added. The mixture is stirred at 25° C. for 16 h and then poured onto a solution of sodium bicarbonate (20 g) in ice water (500 mL). The product is extracted with ethyl acetate (2×150 mL). The organic layer is washed with brine (50 mL), dried over sodium sulfate (powdered) and evaporated under reduced pressure (below 40° C.). The residue is chromatographed on silica gel (400 g, ethyl acetate-hexane 1:1. Selected fractions were combined, concentrated under reduced pressure and dried at 25° C./0.2 mmHg to give the title compound.

Example 85

[N[6]-Benzoyl-5'-O-(4,4'-dimethoxytrityl)-2'-O-(trans-2-methoxycyclohexyl)adenosine-3'-O-yl]-N,N-diisopropylamino-cyanoethoxy Phosphoramidite Phosphitylation of N[6]-benzoyl-5'-O-(dimethoxy-trityl)-2'-O-(trans-2-methoxycyclohexyl)adenosine was performed as illustrated above to give the title compound.

Example 86

General Procedures for Chimeric C3'-Endo and C2'-Enido Modified Oligonucleotide Synthesis Oligonucleotides are synthesized on a PerSeptive Biosystems Expedite 8901 Nucleic Acid Synthesis System. Multiple 1-mmol syntheses are performed for each oligonucleotide. The 3'-end nucleoside containing solid support is loaded into the column. Trityl groups are removed with trichloroacetic acid (975 mL over one minute) followed by an acetonitrile wash. The oligonucleotide is built using a modified diester (P=O) or thioate (P=S) protocol.

Phosphodiester Protocol

All standard amidites (0.1 M) are coupled over a 1.5 minute time frame, delivering 105 μL material. All novel amidites are dissolved in dry acetonitrile (100 mg of amidite/1 mL acetonitrile) to give approximately 0.08–0.1 M solutions. The 2'-modified amidites (both ribo and arabino monomers) are double coupled using 210 μL over a total of 5 minutes. Total coupling time is approximately 5 minutes (210 mL of amidite delivered). 1-H-tetrazole in acetonitrile is used as the activating agent. Excess amidite is washed away with acetonitrile. (1S)-(+)-(10-camphorsulfonyl) oxaziridine (CSO, 1.0 g CSO/8.72 mL dry acetonitrile) is used to oxidize (3 minute wait step) delivering approximately 375 μL of oxidizer. Standard amidites are delivered (210 μL) over a 3-minute period.

Phosphorothioate Protocol

The 2'-modified amidite is double coupled using 210 μL over a total of 5 minutes. The amount of oxidizer, 3H-1,2-benzodithiole-3-one-1,1-dioxide (Beaucage reagent, 3.4 g Beaucage reagent/200 mL acetonitrile), is 225 μL (one minute wait step). The unreacted nucleoside is capped with a 50:50 mixture of tetrahydrofuran/acetic anhydride and tetrahydrofuran/pyridine/1-methyl imidazole. Trityl yields are followed by the trityl monitor during the duration of the synthesis. The final DMT group is left intact. After the synthesis, the contents of the synthesis cartridge (1 mmole) is transferred to a Pyrex vial and the oligonucleotide is cleaved from the controlled pore glass (CPG) using 30% ammonium hydroxide (NH$_4$OH, 5 mL) for approximately 16 hours at 55° C.

Oligonucleotide Purification

After the deprotection step, the samples are filtered from CPG using Gelman 0.45 μm nylon acrodisc syringe filters. Excess NH$_4$OH is evaporated away in a Savant AS160 automatic speed vac. The crude yield is measured on a Hewlett Packard 8452A Diode Array Spectrophotometer at 260 nm. Crude samples are then analyzed by mass spectrometry (MS) on a Hewlett Packard electrospray mass spectrometer. Trityl-on oligonucleotides are purified by reverse phase preparative high performance liquid chromatography (HPLC). HPLC conditions are as follows: Waters 600E with 991 detector; Waters Delta Pak C4 column (7.8×300 mm); Solvent A: 50 mM triethylammonium acetate (TEA-Ac), pH 7.0; Solvent B: 100% acetonitrile; 2.5 mL/min flow rate; Gradient: 5% B for first five minutes with linear increase in B to 60% during the next 55 minutes. Fractions containing the desired product/s (retention time= 41 minutes for DMT-ON-16314; retention time=42.5 minutes for DMT-ON-16315) are collected and the solvent is dried off in the speed vac. Oligonucleotides are detritylated in 80% acetic acid for approximately 60 minutes and lyophilized again. Free trityl and excess salt are removed by passing detritylated oligonucleotides through Sephadex G-25 (size exclusion chromatography) and collecting appropriate samples through a Pharmacia fraction collector. The solvent is again evaporated away in a speed vac. Purified oligonucleotides are then analyzed for purity by CGE, HPLC (flow rate: 1.5 mL/min; Waters Delta Pak C4 column, 3.9×300 mm), and MS. The final yield is determined by spectrophotometer at 260 nm. Example 87

Rapid Amplification of 5'-cDNA End (5'-RACE) and 3'-cDNA End (3'-RACE)

An internet search of the XREF database in the National Center of Biotechnology Information (NCBI) yielded a 361 base pair (bp) human expressed sequenced tag (EST, GenBank accession #H28861), homologous to yeast RNase H (RNH1) protein sequenced tag (EST, GenBank accession #Q04740) and its chicken homologue (accession #D26340). Three sets of oligonucleotide primers encoding the human RNase H EST sequence were synthesized. The sense primers were ACGCTGGCCGGGAGTCGAAATGCTTC (H1: SEQ ID NO: 6), CTGTTCCTGGCCCACAGAGTCGCCT-TGG (H3: SEQ ID NO: 7) and GGTCTTTCTGACCTG-GAATGAGTGCAGAG (H5: SEQ ID NO: 8). The antisense primers were CTTGCCTGGTTTCGCCCTCCGATTCT-TGT (H2: SEQ ID NO: 9), TTGATTTTCATGCCCTTCT-GAAACTTCCG (H4; SEQ ID NO: 10) and CCTCATC-CTCTATGGCAAACTTCTTAAATCTGGC (H6; SEQ ID NO: 11). The human RNase H 3' and 5' cDNAs derived from the EST sequence were amplified by polymerase chain reaction (PCR), using human liver or leukemia (lymphoblastic Molt-4) cell line Marathon ready cDNA as templates, H1 or H3/AP1 as well as H4 or H6/AP2 as primers (Clontech, Palo Alto, Calif.). The fragments were subjected to agarose gel electrophoresis and transferred to nitrocellulose membrane (Bio-Rad, Hercules Calif.) for confirmation by Southern blot, using $^{32}$P-labeled H2 and H1 probes (for 3' and 5' RACE products, respectively, in accordance with procedures described by Ausubel et al., Current Protocols in Molecular Biology, Wiley and Sons, New York, N.Y., 1988. The confirmed fragments were excised from the agarose gel and purified by gel extraction (Qiagen, Germany), then subcloned into Zero-blunt vector (Invitrogen, Carlsbad, Calif.) and subjected to DNA sequencing.

Example 88

Screening of the cDNA Library, DNA Sequencing and Sequence Analysis

A human liver cDNA lambda phage Uni-ZAP library (Stratagene, La Jolla, Calif.) was screened using the PACE products as specific probes. The positive cDNA clones were excised into the pBluescript phagemid (Stratagene, La Jolla Calif.) from lambda phage and subjected to DNA sequencing with an automatic DNA sequencer (Applied Biosystems, Foster City, Calif.) by Retrogen Inc. (San Diego, Calif.). The overlapping sequences were aligned and combined by the assembling programs of MacDNASIS v3.0 (Hitachi Software Engineering America, South San Francisco, Calif.). Protein structure and subsequence analysis were performed by the program of MacVector 6.0 (Oxford Molecular Group Inc., Campbell, Calif.). A homology search was performed on the NCBI database by internet E-mail.

Example 89

Northern Blot and Southern Blot Analysis

Total RNA from different human cell lines (ATCC, Rockville, Md.) was prepared and subjected to formaldehyde agarose gel electrophoresis in accordance with procedures described by Ausubel et al., Current Protocols in Molecular Biology, Wiley and Sons, New York, N.Y., 1988, and transferred to nitrocellulose membrane (Bio-Rad, Hercules Calif.). Northern blot hybridization was carried out in QuickHyb buffer (Stratagene, La Jolla, Calif.) with $^{32}$P-labeled probe of full length RNase H cDNA clone or primer H1/H2 PCR-generated 322-base N-terminal RNase H cDNA fragment at 68° C. for 2 hours. The membranes were washed twice with 0.1% SSC/0.1% SDS for 30 minutes and subjected to auto-radiography. Southern blot analysis was carried out in 1xpre-hybridization/hybridization buffer (BRL, Gaithersburg, Md.) with a $^{32}$P-labeled 430 bp C-terminal restriction enzyme PstI/PvuII fragment or 1.7 kb full length cDNA probe at 60° C. for 18 hours. The membranes were washed twice with 0.1% SSC/0.1% SDS at 60° C. for 30 minutes, and subjected to autoradiography.

Example 90

Expression and Purification of the Cloned RNase Protein

The cDNA fragment coding the full RNase H protein sequence was amplified by PCR using 2 primers, one of which contains restriction enzyme NdeI site adapter and six histidine (his-tag) codons and 22 bp protein N terminal coding sequence. The fragment was cloned into expression vector pET17b (Novagen, Madison, Wis.) and confirmed by DNA sequencing. The plasmid was transfected into E.coli BL21(DE3) (Novagen, Madison, Wis.). The bacteria were grown in M9ZB medium at 32° C. and harvested when the $OD_{600}$ of the culture reached 0.8, in accordance with procedures described by Ausubel et al., Current Protocols in Molecular Biology, Wiley and Sons, New York, N.Y., 1988. Cells were lysed in 8M urea solution and recombinant protein was partially purified with Ni-NTA agarose (Qiagen, Germany). Further purification was performed with C4 reverse phase chromatography (Beckman, System Gold, Fullerton, Calif.) with 0.1% TFA water and 0.1% TFA acetonitrile gradient of 0% to 80% in 40 minutes as described by Deutscher, M. P., Guide to Protein Purification, Methods in Enzymology 182, Academic Press, New York, N.Y., 1990. The recombinant proteins and control samples were collected, lyophilized and subjected to 12% SDS-PAGE as described by Ausubel et al. (1988) Current Protocols in Molecular Biology, Wiley and Sons, New York, N.Y. The purified protein and control samples were resuspended in 6 M urea solution containing 20 mM Tris HCl, pH 7.4, 400 mM NaCl, 20% glycerol, 0.2 mM PMSF, 5 mM DTT, 10 μg/ml aprotinin and leupeptin, and refolded by dialysis with decreasing urea concentration from 6 M to 0.5 M as well as DTT concentration from 5 mM to 0.5 mM as described by Deutscher, M. P., Guide to Protein Purification, Methods in Enzymology 182, Academic Press, New York, N.Y., 1990. The refolded proteins were concentrated (10 fold) by Centricon (Amicon, Danvers, Mass.) and subjected to RNase H activity assay.

Example 91

RNase H Activity Assay $^{32}$P-end-labeled 17-mer RNA, GGGCGCCGTCGGT-GTGG (SEQ ID NO: 12) described by Lima, W. F. and Crooke, S. T., Biochemistry, 1997 36, 390–398, was gel-purified as described by Ausubel et al., Current Protocols in Molecular Biology, Wiley and Sons, New York, N.Y., 1988 and annealed with a tenfold excess of its complementary 17-mer oligodeoxynucleotide or a 5-base DNA gapmer, i.e., a 17mer oligonucleotide which has a central portion of 5 deoxynucleotides (the "gap") flanked on both sides by 6 2'-methoxynucleotides. Annealing was done in 10 mM Tris HCl, pH 8.0, 10 mM MgCl, 50 mM KCl and 0.1 mM DTT to form one of three different substrates: (a) single strand (ss) RNA probe, (b) full RNA/DNA duplex and (c) RNA/DNA gapmer duplex. Each of these substrates was incubated with protein samples at 37° C. for 5 minutes to 2 hours at the same conditions used in the annealing procedure and the reactions were terminated by adding EDTA in accordance with procedures described by Lima, W. F. and Crooke, S. T., Biochemistry, 1997, 36, 390–398. The reaction mixtures were precipitated with TCA centrifugation and the supernatant was measured by liquid scintillation counting (Beckman LS6000IC, Fullerton, Calif.). An aliquot of the reaction mixture was also subjected to denaturing (8 M urea) acrylamide gel electrophoresis in accordance with procedures described by Lima, W. F. and Crooke, S. T., Biochemistry, 1997, 36, 390–398 and Ausubel et al., Current Protocols in Molecular Biology, Wiley and Sons, New York, N.Y., 1988.

Example 92

Effects of Phosphorothioate Substitution and Substrate Length on Digestion by Human RNase H1 (See Table 4)

Oligoribonucleotides were preannealed with the complementary antisense oligodeoxynucleotide at 10 nM and 20 nM respectively and subjected to digestion by Human RNase H1. The 17 mer (RNA no.1) and 25 mer (RNA no.3) RNA sequences are derived from Harvy-RAS oncogen 51) and the 25 mer RNA contains the 17 mer sequence. The 20 mer (RNA no.2) sequence is derived from human hepatitis C virus core protein coding sequence (52). The initial rates were determined as described in Materials and Methods, 1A: Comparison of the initial rates of cleavage of an RNA:phosphodiester (P=O) and an RNA:phosphorothioate (P=S) duplexes, and 1B: Comparison among duplexes of different sequences and lengths.

Example 93

Effects of 2'-Substitution and Deoxy-gap Size on Digestion Rates by Human RNase H1 (See Table 5)

Substrate duplexes were hybridized and initial rates were determined as shown in Table 4 and described in Material and Methods. The 17 mer RNA is the same used in Table 4, and the 20 mer RNA (UGGUGGGCAAUGGGCGUGUU (SEQ ID NO: 12), RNA no.4) is derived from the protein kinase C-zeta (53) sequence. The 17 mer and 20 mer P=S oligonucleotides were full deoxyphosphorothioate containing no 2'-modifications. The 9, 7, 5, 4 and 3 deoxy gap oligonucleotides were 17 mer oligonucleotide with a central portion consisting of nine, seven, five and four deoxynucleotides flanked on both sides by 2'-methoxynucleotides (also see FIG. 2). Boxed sequences indicate the position of the 2'-methoxy-modified residues. Dash-boxed sequence indicates the position of the 2'-propoxy-modified residues.

Example 94

Kinetic Constants for RNase H1 Cleavage of RNA:DNA Duplexes (See Table 6)

The RNA:DNA duplexes in Table 4 were used to determine Km and Vmax of Human and *E.coli* RNase H1 as described in the Materials and Methods section.

Example 95

Binding Constants and Specificity of RNase H's (See Table 7)

$K_d$'s were determined as described in Materials and methods. The $K_d$'s for *E. coli* RNase H1 was derived from previously reported data (21). The competing substrates (competitive inhibitors) used in the binding study are divided into two categories: single-strand (ss) oligonucleotides and oligonucleotide duplexes all with the 17 mer sequence as in Table 4 (RNA No. 1). The single-strand oligonucleotides included: ssRNA, ssDNA, ss fully modified 2'-methoxy phosphodiester oligonucleotide (ss 2'-O-Me) and ss full phosphorothioate deoxyoligonucleotide (ss DNA, P=S). The duplex substrates include: DNA:DNA duplex, RNA:RNA duplex, DNA:fully modified 2' fluoro or fully modified 2'-methoxy oligonucleotide (DNA:2'-F or 2'-O-Me), RNA:2'-F or 2'-O-Me duplex. Dissociation constants are derived from ≧3 slopes of Lineweaver-Burk and/or Augustisson analysis. Estimated errors for the dissociation constants are 2 fold. Specificity is defined by dividing the $K_d$ for a duplex by the $K_d$ for an RNA:RNA duplex.

TABLE 4

A

| RNA | | Antisense | Initial Rate |
|---|---|---|---|
| 1 | GGGCGCCGUCGGUGUGG | 17 mer P=O | 1050 ± 203 |
| 1 | GGGCGCCGUCGGUGUGG | 17 mer P=S | 4034 ± 266 |

B

| RNA No. | RNA | Antisense DNA | Initial Rate (pmol L$^{-1}$ min$^{-1}$) |
|---|---|---|---|
| 1 | GGGCGCCGUCGGUGUGG (SEQ ID NO: 21) | 17 mer P=O | 1050 ± 203 |
| 2 | ACUCCACCAUAGUACACUCC (SEQ ID NO: 22) | 20 mer P=O | 1015 ± 264 |
| 3 | UGGUGGGCGCCGUCGGUGUGGCAA (SEQ ID NO: 23) | 25 mer P=O | 1502 ± 182 |

TABLE 5

| RNA No. | RNA | Antisense DNA | Initial Rate (pmol L$^{-1}$min$^{-1}$) |
|---|---|---|---|
| 1 | 17 mer | CCACACCGACGGCGCCC (SEQ ID NO: 24) | 4034 ± 266 |
| | 17 mer | CCACACCGACGGCGCCC | 1081 ± 168 |
| | 17 mer | CCACACCGACGGCGCCC | 605 ± 81 |
| | 17 mer | CCACACCGACGGCGCCC | 330 ± 56 |
| | 17 mer | CCACACCGACGGCGCCC | 0 |
| | 17 mer | CCACACCGACGGCGCCC | 0 |
| | 17 mer | CCACACCGACGGCGCCC | 0 |
| 4* | 20 mer | AACACGCCCATTGCCCACCA (SEQ ID NO: 25) | 3400 ± 384 |
| | 20 mer | AACACGCCCATTGCCCACCA | 0 |

*Table legend for sequence

TABLE 6

| | Human RNase H | | E. coli RNase H1 | |
|---|---|---|---|---|
| Substrates | Km (nM) | (nmol L$^{-1}$ min$^{-1}$) | Km (nM) | Vmax (nmol L$^{-1}$min$^{-1}$) |
| 25 mer Ras(RNA no.3): DNA (P=O) | 35.4 | 1.907 | | |
| 17 mer Ras(RNA no.1): DNA (P=O) | 56.1 | 1.961 | 385 | 38.8 |
| 17 mer Ras(RNA no.1): DNA (P=S) | 13.9 | 1.077 | | |

TABLE 7

| | Human RNase H1 | | E. coli RNase H1 | |
|---|---|---|---|---|
| Inhibitors | Kd(nM) | Specificity | Kd(nM) | Specificity |
| DNA: 2'-O—Me | 458 | 5.8 | 3400 | 2.1 |
| RNA: 2'-O—Me | 409 | 5.2 | 3100 | 1.9 |
| RNA: RNA | 79 | 1.0 | 1600 | 1.0 |
| RNA: 2'-F | 76 | 1.0 | | |
| DNA: 2'-F | 99 | 1.3 | | |
| DNA: DNA | 3608 | 45.7 | 176000 | 110.0 |
| ssRNA | 1400 | 17.7 | | |
| ssDNA | 1506 | 19.6 | 942000 | 588.8 |
| ss2'-O—Me | 2304 | 29.2 | 118000 | 73.8 |
| ssDNA, P=S | 36 | 0.5 | 14000 | 8.8 |

PROCEDURES

PROCEDURE 1

ICAM-1 Expression

Oligonucleotide Treatment of HUVECs

Cells were washed three times with Opti-MEM (Life Technologies, Inc.) prewarmed to 37° C. Oligonucleotides were premixed with 10 g/mL Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/mL TNF-α 7 & D Systems). Incubation at 37° C. was continued until the indicated times.

Quantitation of ICAM-1 Protein Expression by Fluorescence-activated Cell Sorter

Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 $1/10^5$ cells of the ICAM-1 specific antibody, CD54-PE (Pharmingin). Antibodies were incubated with the cells for 30 min at 4C in the dark, under gently agitation. Cells were washed by centrifugation procedures and then resuspended in 0.3 mL of FacsFlow buffer (Becton Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)–(basal ICAM-1 value)/(non-treated ICAM-1 value)–(basal ICAM-1 value)]. (Baker, Brenda, et. al. 2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells, *The Journal of Biological Chemistry*, 272, 11994–12000, 1997.)

ICAM-1 expression of chimeric C3'-endo and C2'-endo modified oligonucleotides of the invention is measured by the reduction of ICAM-1 levels in treated HUVEC cells. The oligonucleotides are believed to work by RNase H cleavage mechanism. Appropriate scrambled control oligonucleotides are used as controls. They have the same base composition as the test sequence.

Sequences that contain the chimeric C3'-endo (2'-MOE) and C2'-endo (one of the following modifications: 2'-S-Me, 2'-Me, 2'-ara-F,2'-ara-OH, 2'-ara-O-Me) as listed in Table X below are prepared and tested in the above assay. SEQ ID NO: 14, a C-raf targeted oligonucleotide, is used as a control.

TABLE X

Oligonucleotides Containing chimeric 2'-O-(2-methoxyethyl) and 2'-S-(methyl) modifications.

| SEQ ID NO: | Sequence (5'–3') | Target |
|---|---|---|
| 14 | AsTsGs C$^m$sAsTs TsC$^m$sTs GsC$^m$s C$^m$ s C$^m$sC$^m$sAsAsGs GsA | mouse C-raf |
| 26 | GsC$^m$sC$^m$s C$^m$sAsAs GsC$^m$sTs GsGsC$^m$s AsTsC$^m$s C$^m$sGsTs C$^m$sA | human ICAM-1 |

All nucleosides in bold are 2'-O-(methoxyethyl); subscript s indicates a phosphorothioate linkage; underlined nucleosides indicate 2'-S-Me-modification. Superscript m on C (C$^m$) indicates a 5-methyl-C.

TABLE XI

Oligonucleotides Containing chimeric 2'-O-(2-methoxyethyl) and 2'-O-(methyl) modifications

| SEQ ID NO: | Sequence (5'–3') | Target |
|---|---|---|
| 14 | AsTsGs C$^m$sAsTs TsC$^m$sTs GsC$^m$sC$^m$s C$^m$sC$^m$sC$^m$s AsAsGs GsA | mouse C-raf |
| 26 | GsC$^m$sC$^m$s C$^m$sAsAs GsC$^m$sTs GsGsC$^m$s AsTsC$^m$s C$^m$sGsTs C$^m$sA | human ICAM-1 |

All nucleosides in bold are 2'-O-(methoxyethyl); subscript s indicates a phosphorothioate linkage; underlined nucleosides indicate 2'-Methyl modification. Superscript m on C (C$^m$)indicates a 5-methyl-C.

TABLE XII

Oligonucleotides Containing chimeric 2'-O-(2-methoxyethyl) and 2'-ara-(fluoro) modifications

| SEQ ID NO: | Sequence (5'–3') | Target |
|---|---|---|
| 14 | AsTsGs C$^m$sAsTs TsC$^m$sTs GsC$^m$sC$^m$s C$^m$sC$^m$sC$^m$s AsAsGs GsA | mouse C-raf |
| 26 | GsC$^m$sC$^m$s C$^m$sAsAs GsC$^m$sTs GsGsC$^m$s AsTsC$^m$s C$^m$sGsTs C$^m$sA | human ICAM-1 |

All nucleosides in bold are 2'-O-(methoxyethyl); subscript s indicates a phosphorothioate linkage; underlined nucleosides indicate 2'-ara-(fluoro) modification. Superscript m on C (C$^m$) indicates a 5-methyl-C.

TABLE XIII

Oligonucleotides Containing chimeric 2'-O-(2-methoxyethyl) and 2'-ara-(OH) modifications

| SEQ ID NO: | Sequence (5'–3') | Target |
|---|---|---|
| 14 | AsTsGs C$^m$sAsTs TsC$^m$sTs GsC$^m$sC$^m$s C$^m$sC$^m$sC$^m$s AsAsGs GsA | mouse C-raf |
| 26 | GsC$^m$sC$^m$s C$^m$sAsAs GsC$^m$sTs GsGsC$^m$s AsTsC$^m$s C$^m$sGsTs C$^m$sA | human ICAM-1 |

All nucleosides in bold are 2=-O-(methoxyethyl); subscript s indicates a phosphorothioate linkage; underlined nucleosides indicate 2'-ara-(OH) modification. superscript m on C (C$^m$)indicates a 5-methyl-C.

TABLE XIV

Oligonucleotides Containing chimeric 2'-O-(2-methoxyethyl) and 2'-ara-(OMe) modifications

| SEQ ID NO: | Sequence (5'–3') | Target |
|---|---|---|
| 14 | AsTsGs C$^m$sAsTs TsC$^m$sTs GsC$^m$sC$^m$s C$^m$sC$^m$sC$^m$s AsAsGs GsA | mouse C-raf |
| 26 | GsC$^m$sC$^m$s C$^m$sAsAs GsC$^m$sTs GsGsC$^m$s AsTsC$^m$s C$^m$sGsTs C$^m$sA-3' | human ICAM-1 |

All nucleosides in bold are 2=-O-(methoxyethyl); subscript S indicates a phosphorothioate linkage; underlined nucleosides indicate 2'-ara-(OMe) modification. superscript m on C (C^m) indicates a 5-methyl-C.

PROCEDURE 2
Enzymatic Degradation of 2'-O-Modified Oligonucleotides

Three oligonucleotides are synthesized incorporating the modifications shown in Table 2 below at the 3'-end. These modified oligonucleotides are subjected to snake venom phosphodiesterase action.

Oligonucleotides (30 nanomoles) are dissolved in 20 mL of buffer containing 50 mM Tris-HCl pH 8.5, 14 mM $MgCl_2$, and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) are added and the reaction mixture is incubated at 37C for 100 hours. HPLC analysis is carried out using a Waters model 715 automatic injector, model 600E pump, model 991 detector, and an Alltech (Alltech Associates, Inc., Deerfield, Ill.) nucleoside/nucleotide column (4.6×250 mm). All analyses are performed at room temperature. The solvents used are A: water and B: acetonitrile. Analysis of the nucleoside composition is accomplished with the following gradient: 0–5 min., 2% B (isocratic); 5–20 min., 2% B to 10% B (linear); 20–40 min., 10% B to 50% B. The integrated area per nanomole is determined using nucleoside standards. Relative nucleoside ratios are calculated by converting integrated areas to molar values and comparing all values to thymidine, which is set at its expected value for each oligomer.

TABLE XV

Relative Nuclease Resistance of 2'-Modified
Chimeric Oligonucleotides
5'-TTT TTT TTT TTT TTT T*T*T*T*-3' SEQ ID NO 17
(Uniform phosphodiester)

T* = 2'-modified T
—S—Me
—Me
-2'-ara-(F)
-2'-ara-(OH)
-2'-ara-(OMe)

PROCEDURE 3
General Procedure for the Evaluation of Chimeric C3'-Endo and C2'-Endo Modified Oligonucleotides Targeted to Ha-ras Different types of human tumors, including sarcomas, neuroblastomas, leukemias and lymphomas, contain active oncogenes of the ras gene family. Ha-ras is a family of small molecular weight GTPases whose function is to regulate cellular proliferation and differentiation by transmitting signals resulting in constitutive activation of ras are associated with a high percentage of diverse human cancers. Thus, ras represents an attractive target for anticancer therapeutic strategies.

SEQ ID NO: 27 is a 20-base phosphorothioate oligodeoxynucleotide targeting the initiation of translation region of human Ha-ras and it is a potent isotype-specific inhibitor of Ha-ras in cell culture based on screening assays ($IC_{50}$=45 nm). Treatment of cells in vitro with SEQ ID NO: 46 results in a rapid reduction of Ha-ras mRNA and protein synthesis and inhibition of proliferation of cells containing an activating Ha-ras mutation. When administered at doses of 25 mg/kg or lower by daily intraperitoneal injection (IP), SEQ ID NO: 46 exhibits potent antitumor activity in a variety of tumor xenograft models, whereas mismatch controls do not display antitumor activity. SEQ ID NO: 46 has been shown to be active against a variety of tumor types, including lung, breast, bladder, and pancreas in mouse xenograft studies (Cowsert, L. M. *Anti-cancer drug design*, 1997, 12, 359–371). A second-generation analog of SEQ ID NO: 27, where the 5' and 3' termini ("wings") of the sequence are modified with 2'-methoxyethyl (MOE) modification and the backbone is kept as phosphorothioate (Table XV, Control Gapmer with MOE Control), exhibits $IC_{50}$ of 15 nm in cell culture assays. Thus, a 3-fold improvement in efficacy is observed from this chimeric analog. Because of the improved nuclease resistance of the 2'-MOE phosphorothioate, sequence increases the duration of antisense effect in vitro. This will relate to frequency of administration of this drug to cancer patients. Further, this sequence is currently under evaluation in ras dependent tumor models (Cowsert, L. M. *Anti-cancer drug design*, 1997, 12, 359–371). The parent compound, SEQ ID NO: 27, is in Phase I clinical trials against solid tumors by systemic infusion.

Antisense oligonucleotides having the 2'-Me modification are prepared and tested in the aforementioned assays in the manner described to determine activity.

Ha-ras Antisense Oligonucleotides With chimeric C3'-endo and C2'-endo modifications and Their Controls.

TABLE XV

Ha-ras Antisense Oligonucleotides With chimeric
C3'-endo and C2'-endo modifications and Their Controls.

| SEQ ID NO: | Sequence | Backbone | 2'-Modif. | Comments |
|---|---|---|---|---|
| 27 | 5'-TsCsCs GsTsCs AsTsCs GsCsTs CsCsTs CsAsGs GsG-3' | P=S | 2'-H | parent |
| 28 | 5'-TsCsAs GsTsAs AsTsAs GsGsCs CsCsAs CsAsTs GsG-3' | P=S | 2'-H | mismatch control |
| 29 | 5'-ToToCo GsTsCs AsTsCs GsCsTs CoCoTo CoAoGo GoG-3' | P=O/ P=S/ P=O | 2'-O—Moe in wings | Parent Gapmer (Mixed Backbone) |
| 27 | 5'-TsCsCs GsTsCs AsTsCs GsCsTs CsCsTs CsAsGs GsG-3' | P=S | 2'-O—MOE in wings | Parent Gapmer as uniform thioate |
| 30 | 5'-ToCoAo GsTsAs AsTsAs GsCsCs GsCsCs GsCoCo CoCoAo CoAoTo GoG-3' | P=O/ P=S/ P=O | 2'-O—MOE in wings | Parent Gapmer (mixed Backbone) |
| 31 | 5'-TsCsAs GsTsAs AsTs As GsCsCs GsCsCs CsCsAs CsAsTs GsC-3' | P=S | 2'-O—MOE in wings | Control Gapmer as uniform Thioate |
| 27 | 5'-TsCsCs GsTsCs AsTsCs GsCsTs CsCsTs CsAsGs GsG-3' | P=S | 2'-O—MOE in wings | Control Gapmer with MOE control |
| 31 | 5'-TsCsAs GsTsAs AsTsAs GsCsCs GsCsCs CsCsAs CsAsTs GsC-3' | P=S | 2'-O—MOE in wings | Control Gapmer with MOE control |

All underlined portions of sequences are 2'-Me.

PROCEDURE 7
In Vivo Nuclease Resistance

The in vivo Nuclease Resistance of chimeric C3'-endo and C2'-endo modified oligonucleotides is studied in mouse plasma and tissues (kidney and liver). For this purpose, the C-raf oligonucleotide series SEQ ID NO: 32 are used and the following five oligonucleotides listed in the Table below will be evaluated for their relative nuclease resistance.

TABLE XVI

Study of in vivo Nuclease Resistance of chimeric C3'-endo (2'-O—MOE) and C2'-endo (2'-S—Me) modified oligonucleotides with and without nuclease resistant caps (2'–5'-phosphate or phosphorothioate linkage with 3'-O—MOE in cap ends).

| SEQ ID NO: | Sequence | Backbone | Description |
|---|---|---|---|
| 32 | 5'-ATG CAT TCT GCC CCA AGGA-3' | P=S, 2'-H | (control) rodent C-raf antisense oligo |
| | AoToGo CoAsTs TsCsTs GsCsCs CsCsAo AoGoGo A | P=O/P=S/P=O | 2'-MOE/2'-S—Me/ 2'-MOE |
| | AsTsGs CsAsTs TsCsTs GsCsCs CsCsAs AsGsGs A | P=S | 2'-MOE/2'-S—Me/ 2'-MOE |
| | Ao*ToGo CoAsTs TsCsTs GsCsCs CsCsAo AoGoGo *A | P=O/P=S/P=O | In asterisk, 2'–5' linkage with 3'-O—MOE; 2'-O—MOE / 2'-S—Me/2'-O—MOE/2'–5' linkage with 3'-O—MOE in asterisk; |
| | As*TsGs CsAsTs TsCsTs GsCsCs CsCsAs AsGsGs *A | P=S | In asterisk, 2'–5' linkage with 3'-O—MOE; 2'-O-MOE/ 2'-S—Me/2'-O—MOE/2'–5' linkage with 3'-O—MOE in asterisk. |

TABLE XVII

Study of in vivo Nuclease Resistance of chimeric C3'-endo (2'-O—MOE) and C2'-endo (2'-Me) modified oligonucleotides with and without nuclease resistant caps (2'–5'-phosphate or phosphorothioate linkage with 3'-O—MOE in cap ends).

| SEQ ID NO: | Sequence | Backbone | Description |
|---|---|---|---|
| 32 | 5'-ATG CAT TCT GCC CCA AGGA-3' | P=S, 2'-H | (control) rodent C-raf antisense oligo |
| | AoToGo CoAsTs TsCsTs GsCsCs CsCsAo AoGoGo A' | P=O/P=S/P=O | 2'-MOE/2'-Me/ 2'-MOE |
| | AsTsGs CsAsTs TsCsTs GsCsCs CsCsAs AsGsGs A | P=S | 2'-MOE/2'-Me/ 2'-MOE |
| | Ao*ToGo CoAsTs TsCsTs GsCsCs CsCsAo AoGoGo *A | P=O/P=S/P=O | In asterisk, 2'–5' linkage with 3'-O—MOE; 2'-O—MOE 2'-Me/2'-O—MOE/2'–5' linkage with 3'-O—MOE in asterisk; |
| | As*TsGs CsAsTs TsCsTs GsCsCs CsCsAs AsGsGs *A | P=S | In asterisk, 2'–5' linkage with 3'-O—MOE; 2'-O—MOE/ 2'-Me/2'-O—MOE/2'–5' linkage with 3'-O—MOE in asterisk; |

TABLE XVIII

Study of in vivo Nuclease Resistance of chimeric
C3'-endo (2'-O—MOE) and C2'-endo (2'-ara-F) modified
oligonucleotides with and without nuclease resistant caps
(2'–5'-phosphate or phosphorothioate linkage
with 3'-O—MOE in cap ends).

| SEQ ID NO: | Sequence | Backbone | Description |
|---|---|---|---|
| 32 | 5'-ATG CAT TCT GCC CCA AGGA-3' | P=S, 2'-H | (control) rodent C-raf antisense oligo |
| | AoToGo CoAsTs TsCsTs GsCsCs CsCsAo AoGoGo A | P=O/P=S/P=O | 2'-MOE/2'-ara-F/ 2'-MOE |
| | AsTsGs CsAsTs TsCsTs GsCsCs CsCsAs AsGsGs A | P=S | 2'-MOE/2'-ara-F/2'-MOE |
| | Ao*ToGo CoAsTs TsCsTs GsCsCs CsCsAo AoGoGo *A | P=O/P=S/P=O | In asterisk, 2'–5' linkage with 3'-O—MOE; 2'-O—MOE/ 2'-ara-F/2'-O—MOE/2'–5' linkage with 3'-O—MOE in asterisk; |
| | As*TsGs CsAsTs TsCsTs GsCsCs CsCsAs AsGsGs *A | P=S | In asterisk, 2'–5' linkage with 3'-O—MOE; 2'-O—MO 2'-ara-F/2'-O—MOE/2'–5' linkage with 3'-O—MOE in asterisk; |

TABLE XIX

Study of in vivo Nuclease Resistance of chimeric
C3'-endo (2'-O—MOE) and C2'-endo (2'-ara-OH) modified
oligonucleotides with and without nuclease resistant caps
(2'–5'-phosphate or phosphorothioate linkage
with 3'-O—MOE in cap ends).

| SEQ ID NO: | Sequence | Backbone | Description |
|---|---|---|---|
| 32 | 5'-ATG CAT TCT GCC CCA AGGA-3' | P=S, 2'-H | (control) rodent C-raf antisense oligo |
| | AoToGo CoAsTs TsCsTs GsCsCs CsCsAo AoGoGo A | P=O/P=S/P=O | 2'-MOE/2'-ara-OH/ 2'-MOE |
| | AsTsGs CsAsTs TsCsTs GsCsCs CsCsAs AsGsGs A | P=S | 2'-MOE/2'-ara-OH/ 2'-MOE |
| | Ao*ToGo CoAsTs TsCsTs GsCsCs CsCsAo AoCoGo *A | P=O/P=S/P=O | In asterisk, 2'–5' linkage with 3'-O—MOE; 2'-O—MOE/ 2'-ara-OH/2'-O—MOE/2'–5' linkage with 3'-O—MOE in asterisk; |
| | As*TsGs CsAsTs TsCsTs GsCsCs CsCsAs AsGsGs *A | P=S | In asterisk, 2'–5' linkage with 3'-O—MOE; 2'-O—MOE/ 2'-ara-OH/2'-O—MOE/2'–5' linkage with 3'-O—MOE in asterisk; |

TABLE XX

Study of in vivo Nuclease Resistance of chimeric C3'-endo
(2'-O—MOE) and C2'-endo (2'-ara-OMe) modified
oligonucleotides with and without nuclease resistant caps
(2'-5'-phosphate or phosphorothioate linkage
with 3'-O—MOE in cap ends).

| SEQ ID NO: | Sequence | Backbone | Description |
|---|---|---|---|
| 32 | 5'-ATG CAT TCT GCC CCA AGG A-3' | P=S, 2+-H | (control) rodent C-raf antisense oligo |
| | AoToGo CoAsTs TsCsTs GsCsCs CsCsAo AoGoGo Aa | P=O/P=S/P=O | 2'-MOE/2'-ara-OMe/ 2'-MOE |
| | AsTsGs CsAsTs TsCsTs GsCsCs CsCsAs AsGsGs A | P=S | 2'-MOE/2'-ara-OMe/ 2'-MOE |
| | Ao*ToGo CoAsTs TsCsTs GsCsCs CsCsAo AoGoGo *A | P=O/P=S/P=O | In asterisk, 2'-5' linkage with 3'-O—MOE; 2'-O—MOE/ 2'-ara-OMe/2'-O—MOE/2'-5' linkage with 3'-O—MOE in asterisk; |
| | As*TsGs CsAsTs TsCsTs GsCsCs CsCsAs AsGsGs *A | P=S | In asterisk, 2'-5' linkage with 3'-O—MOE; 2'-O—MOE/ 2'-ara-OMe/2'-O—MOE/2'-5' linkage with 3'-O—MOE in asterisk. |

PROCEDURE 8
Animal Studies for in Vivo Nuclease Resistance

For each oligonucleotide to be studied, 9 male BALB/c mice (Charles River, Wilmington, Mass.), weighing about 25 g are used (Crooke et al., *J. Pharmacol. Exp. Ther.*, 1996, 277, 923). Following a 1-week acclimation, the mice receive a single tail vein injection of oligonucleotide (5 mg/kg) administered in phosphate buffered saline (PBS), pH 7.0. The final concentration of oligonucleotide in the dosing solution is (5 mg/kg) for the PBS formulations. One retro-orbital bleed (either 0.25, 9.05, 2 or 4 post dose) and a terminal bleed (either 1, 3, 8 or 24 h post dose) is collected from each group. The terminal bleed (approximately 0.6–0.8 mL) is collected by cardiac puncture following ketamine/xylazine anesthesia. The blood is transferred to an EDTA-coated collection tube and centrifuged to obtain plasma. At termination, the liver and kidneys will be collected from each mouse. Plasma and tissues homogenates will be used for analysis for determination of intact oligonucleotide content by CGE. All samples are immediately frozen on dry ice after collection and stored at −80C until analysis.

PROCEDURE 9
RNase H Studies with Chimeric C3'-Endo and C2'-Endo Modified Oligonucleotides With and Without Nuclease Resistant Caps $^{32}$P Labeling of Oligonucleotides The oligoribonucleotide (sense strand) was 5'-end labeled with $^{32}$P using [$^{32}$P]ATP, T4 polynucleotide kinase, and standard procedures (Ausubel, F. M., Brent, R., Kingston, R. E., Moore, D. D., Seidman, J. G., Smith, J. A., and Struhl, K., in *Current Protocols in Molecular Biology*, John Wiley, New York (1989)). The labeled RNA was purified by electrophoresis on 12% denaturing PAGE (Sambrook, J., Frisch, E. F., and Maniatis, T., *Molecular Cloning: A Laboratory Manual*, Cold Spring Harbor Laboratory Press, Plainview (1989)). The specific activity of the labeled oligonucleotide was approximately 6000 cpm/fmol.

Determination of RNase H Cleavage Patterns

Hybridization reactions were prepared in 120 μL of reaction buffer [20 mM Tris-HC (pH 7.5), 20 mM KCl, 10 mM MgCl$_2$, 0.1 mM DTT] containing 750 nM antisense oligonucleotide, 500 nM sense oligoribonucleotide, and 100,000 cpm $^{32}$P-labeled sense oligoribonucleotide. Reactions were heated at 90° C. for 5 min and 1 unit of Inhibit-ACE was added. Samples were incubated overnight at 37° C. degrees. Hybridization reactions were incubated at 37° C. with 1.5×10.8$^{-8}$ mg of *E. coli* RNase H enzyme for initial rate determinations and then quenched at specific time points. Samples were analyzed by trichloroacetic acid (TCA) assay or by denaturing polyacrylamide gel electrophoresis as previously described [Crooke, S. T., Lemonidis, K. M., Neilson, L., Griffey, R., Lesnik, E. A., and Monia, B. P., Kinetic characteristics of *Escherichia coli* RNase H1: cleavage of various antisense oligonucleotide-RNA duplexes, *Biochem J*, 312, 599 (1995); Lima, W. F. and Crooke, S. T., Biochemistry 36, 390–398, 1997].

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A mixed sequence oligonucleotide comprising at least 12 nucleotides and having a 3' end and a 5' end and divided into a first portion and a further portion, said first portion supports cleavage of a complementary target RNA by human RNase H1 polypeptide, said further portion that does not support said cleavage by said RNase H1;

wherein:

said first portion comprises at least 6 nucleotides and is positioned in said oligonucleotide such that at least one of said 6 nucleotides is 8 to 12 nucleotides from the 3' end of said oligonucleotide;

said first portion comprises at least one 5'-CA-3' nucleotide sequence that is positioned 8 to 12 nucleotides from the 3' end of said oligonucleotide, and each nucleotide of said first portion is, independently, a 2'-CN arabinonucleotide, a 2'-Cl arabinonucleotide, a 2'-Br arabinonucleotide, a 2'-$N_3$ arabinonucleotide, a 2'-OH arabinonucleotide, a 2'-O—$CH_3$ arabinonucleotide or a 2'-dehydro-2'-$CH_3$ arabinonucleotide.

2. The oligonucleotide of claim 1 wherein each of said nucleotides of said first portion is, independently, a 2'-OH arabinonucleotide or a 2'-O—$CH_3$ arabinonucleotide.

3. The oligonucleotide of claim 1 wherein each of said nucleotides of said first portion is a 2'-OH arabinonucleotide.

4. A method comprising contacting an oligonucleotide according to claim 1 with RNA or DNA in vitro.

5. A method comprising contacting an oligonucleotide according to claim 1 with RNA or DNA in a cellular assay.

6. A mixed sequence oligonucleotide comprising at least 12 nucleotides and having a 3' end and a 5' end and divided into a first portion and a further portion, said first portion supports cleavage of a complementary target RNA by human RNase H1 polypeptide, said further portion does not support said cleavage by said RNase H1;

wherein:

said first portion comprises at least 6 nucleotides and is positioned in said oligonucleotide such that at least one of said 6 nucleotides is 8 to 12 nucleotides from the 3' end of said oligonucleotide; said first portion comprises at least one 5'-CA-3' nucleotide sequence that is positioned 8 to 12 nucleotides from the 3' end of said oligonucleotide; and each of said nucleotides of said first portion is, independently, a 2'-$SCH_3$ ribonucleotide, a 2'-$NH_2$ ribonucleotide, a 2'-NH($C_1$–$C_2$ alkyl)ribonucleotide, a 2'-N($C_1$–$C_2$ alkyl)$_2$ ribonucleotide, a 2'-$CF_3$ ribonucleotide, a 2'=$CH_2$ ribonucleotide, a 2'=CHF ribonucleotide, a 2'=$CF_2$ ribonucleotide, a 2'-$CH_3$ ribonucleotide, a 2'-$C_2H_5$ ribonucleotide, a 2'-CH=$CH_2$ ribonucleotide or a 2'-C≡CH ribonucleotide.

7. A method comprising contacting an oligonucleotide according to claim 6 with RNA or DNA in vitro.

* * * * *

UNITED STATES PATENT AND TRADEMARK OFFICE
CERTIFICATE OF CORRECTION

PATENT NO. : 6,617,442 B1
DATED : September 9, 2003
INVENTOR(S) : Stanley T. Crooke et al.

It is certified that error appears in the above-identified patent and that said Letters Patent is hereby corrected as shown below:

Title page,
Item [56], Reference Cited, OTHER PUBLICATIONS, "M.J. Damha", reference, please delete "Arabinobucleic" and insert therefor -- Arabinonucleic --;
"Bordier", reference, please delete "inibition" and insert therefor -- inhibition --;
"Lee", reference, please delete "umibilical" and insert therefor -- umbilical --;
"Baker", reference, please delete "Oligonnucleotides" and insert therefor -- Oligonucleotides --;
"Lima", reference, please delete "Catalysts" and insert therefor -- Catalysis --;
"Ouchi", reference, please delete "Ehtylene" and insert -- Ethylene --; and
"Yang", reference, please delete "Selenomethioyl" and insert therefor -- Selenomethionyl --.

Signed and Sealed this

Eighth Day of June, 2004

JON W. DUDAS
*Acting Director of the United States Patent and Trademark Office*

SEQUENCE LISTING

<160> NUMBER OF SEQ ID NOS: 33

<210> SEQ ID NO 1
<211> LENGTH: 286
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Met Ser Trp Leu Leu Phe Leu Ala His Arg Val Ala Leu Ala Ala Leu
 1               5                  10                  15

Pro Cys Arg Arg Gly Ser Arg Gly Phe Gly Met Phe Tyr Ala Val Arg
            20                  25                  30

Arg Gly Arg Lys Thr Gly Val Phe Leu Thr Trp Asn Glu Cys Arg Ala
        35                  40                  45

Gln Val Asp Arg Phe Pro Ala Ala Arg Phe Lys Lys Phe Ala Thr Glu
    50                  55                  60

Asp Glu Ala Trp Ala Phe Val Arg Lys Ser Ala Ser Pro Glu Val Ser
65                  70                  75                  80

Glu Gly His Glu Asn Gln His Gly Gln Glu Ser Glu Ala Lys Pro Gly
                85                  90                  95

Lys Arg Leu Arg Glu Pro Leu Asp Gly Asp Gly His Glu Ser Ala Gln
            100                 105                 110

Pro Tyr Ala Lys His Met Lys Pro Ser Val Glu Pro Ala Pro Pro Val
        115                 120                 125

Ser Arg Asp Thr Phe Ser Tyr Met Gly Asp Phe Val Val Tyr Thr
    130                 135                 140

Asp Gly Cys Cys Ser Ser Asn Gly Arg Arg Lys Pro Arg Ala Gly Ile
145                 150                 155                 160

Gly Val Tyr Trp Gly Pro Gly His Pro Leu Asn Val Gly Ile Arg Leu
                165                 170                 175

Pro Gly Arg Gln Thr Asn Gln Arg Ala Glu Ile His Ala Ala Cys Lys
            180                 185                 190

Ala Ile Glu Gln Ala Lys Thr Gln Asn Ile Asn Lys Leu Val Leu Tyr
        195                 200                 205

Thr Asp Ser Met Phe Thr Ile Asn Gly Ile Thr Asn Trp Val Gln Gly
    210                 215                 220

Trp Lys Lys Asn Gly Trp Lys Thr Ser Ala Gly Lys Glu Val Ile Asn
225                 230                 235                 240

Lys Glu Asp Phe Val Ala Leu Glu Arg Leu Thr Gln Gly Met Asp Ile
                245                 250                 255

Gln Trp Met His Val Pro Gly His Ser Gly Phe Ile Gly Asn Glu Glu
            260                 265                 270

Ala Asp Arg Leu Ala Arg Glu Gly Ala Lys Gln Ser Glu Asp
        275                 280                 285

<210> SEQ ID NO 2
<211> LENGTH: 293
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 2

```
Met Leu Arg Trp Leu Val Ala Leu Leu Ser His Ser Cys Phe Val Ser
  1               5                  10                  15

Lys Gly Gly Gly Met Phe Tyr Ala Val Arg Lys Gly Arg Gln Thr Gly
             20                  25                  30

Val Tyr Arg Thr Trp Ala Glu Cys Gln Gln Gln Val Asn Arg Phe Pro
         35                  40                  45

Ser Ala Ser Phe Lys Lys Phe Ala Thr Glu Lys Glu Ala Trp Ala Phe
     50                  55                  60

Val Gly Ala Gly Pro Pro Asp Gly Gln Gln Ser Ala Pro Ala Glu Thr
 65                  70                  75                  80

His Gly Ala Ser Ala Val Ala Gln Glu Asn Ala Ser His Arg Glu Glu
             85                  90                  95

Pro Glu Thr Asp Val Leu Cys Cys Asn Ala Cys Lys Arg Pro Tyr Glu
            100                 105                 110

Gln Ser Thr Asn Glu Glu His Thr Val Arg Arg Ala Lys His Asp Glu
            115                 120                 125

Glu Gln Ser Thr Pro Val Val Ser Glu Ala Lys Phe Ser Tyr Met Gly
        130                 135                 140

Glu Phe Ala Val Val Tyr Thr Asp Gly Cys Cys Ser Gly Asn Gly Arg
145                 150                 155                 160

Asn Arg Ala Arg Ala Gly Ile Gly Val Tyr Trp Gly Pro Gly His Pro
                165                 170                 175

Leu Asn Ile Ser Glu Arg Leu Pro Gly Arg Gln Thr Asn Gln Arg Ala
            180                 185                 190

Glu Ile His Ala Ala Cys Lys Ala Ile Glu Gln Ala Lys Ser Gln Asn
        195                 200                 205

Ile Lys Lys Leu Ile Ile Tyr Thr Asp Ser Lys Phe Thr Ile Asn Gly
    210                 215                 220

Ile Thr Ser Trp Val Glu Asn Trp Lys Thr Asn Gly Trp Arg Thr Ser
225                 230                 235                 240

Ser Gly Gly Ser Val Ile Asn Lys Glu Asp Phe Gln Lys Leu Asp Ser
                245                 250                 255

Leu Ser Lys Gly Ile Glu Ile Gln Trp Met His Ile Pro Gly His Ala
            260                 265                 270

Gly Phe Gln Gly Asn Glu Glu Ala Asp Arg Leu Ala Arg Glu Gly Ala
        275                 280                 285

Ser Lys Gln Lys Leu
        290

<210> SEQ ID NO 3
<211> LENGTH: 348
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 3

Met Ala Arg Gln Gly Asn Phe Tyr Ala Val Arg Lys Gly Arg Glu Thr
  1               5                  10                  15

Gly Ile Tyr Asn Thr Trp Asn Glu Cys Lys Asn Gln Val Asp Gly Tyr
             20                  25                  30

Gly Gly Ala Ile Tyr Lys Lys Phe Asn Ser Tyr Glu Gln Ala Lys Ser
         35                  40                  45

Phe Leu Gly Gln Pro Asn Thr Thr Ser Asn Tyr Gly Ser Ser Thr His
```

-continued

```
                 50                  55                  60
Ala Gly Gly Gln Val Ser Lys Pro His Thr Thr Gln Lys Arg Val His
 65                  70                  75                  80

Arg Arg Asn Arg Pro Leu His Tyr Ser Ser Leu Thr Ser Ser Ser Ala
                 85                  90                  95

Cys Ser Ser Leu Ser Ser Ala Asn Thr Asn Thr Phe Tyr Ser Val Lys
                100                 105                 110

Ser Asn Val Pro Asn Ile Glu Ser Lys Ile Phe Asn Asn Trp Lys Asp
                115                 120                 125

Cys Gln Ala Tyr Val Lys His Lys Arg Gly Ile Thr Phe Lys Lys Phe
130                 135                 140

Glu Asp Gln Leu Ala Ala Glu Asn Phe Ile Ser Gly Met Ser Ala His
145                 150                 155                 160

Asp Tyr Lys Leu Met Asn Ile Ser Lys Glu Ser Phe Glu Ser Lys Tyr
                165                 170                 175

Lys Leu Ser Ser Asn Thr Met Tyr Asn Lys Ser Met Asn Val Tyr Cys
                180                 185                 190

Asp Gly Ser Ser Phe Gly Asn Gly Thr Ser Ser Arg Ala Gly Tyr
                195                 200                 205

Gly Ala Tyr Phe Glu Gly Ala Pro Glu Glu Asn Ile Ser Glu Pro Leu
210                 215                 220

Leu Ser Gly Ala Gln Thr Asn Asn Arg Ala Glu Ile Glu Ala Val Ser
225                 230                 235                 240

Glu Ala Leu Lys Lys Ile Trp Glu Lys Leu Thr Asn Glu Lys Glu Lys
                245                 250                 255

Val Asn Tyr Gln Ile Lys Thr Asp Ser Glu Tyr Val Thr Lys Leu Leu
                260                 265                 270

Asn Asp Arg Tyr Met Thr Tyr Asp Asn Lys Lys Leu Glu Gly Leu Pro
                275                 280                 285

Asn Ser Asp Leu Ile Val Pro Leu Val Gln Arg Phe Val Lys Val Lys
                290                 295                 300

Lys Tyr Tyr Glu Leu Asn Lys Glu Cys Phe Lys Asn Asn Gly Lys Phe
305                 310                 315                 320

Gln Ile Glu Trp Val Lys Gly His Asp Gly Asp Pro Gly Asn Glu Met
                325                 330                 335

Ala Asp Phe Leu Ala Lys Lys Gly Ala Ser Arg Arg
                340                 345

<210> SEQ ID NO 4
<211> LENGTH: 216
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

Gly Ile Cys Gly Leu Gly Met Phe Tyr Ala Val Arg Arg Gly Arg Arg
  1               5                  10                  15

Pro Gly Val Phe Leu Ser Trp Ser Glu Cys Lys Ala Gln Val Asp Arg
                 20                  25                  30

Phe Pro Ala Ala Arg Phe Lys Lys Phe Ala Thr Glu Asp Glu Ala Trp
                 35                  40                  45

Ala Phe Val Arg Ser Ser Ser Pro Asp Gly Ser Lys Gly Gln Glu
 50                  55                  60
```

```
Ser Ala His Glu Gln Lys Ser Gln Ala Lys Thr Ser Lys Arg Pro Arg
 65                  70                  75                  80

Glu Pro Leu Val Val Val Tyr Thr Asp Gly Cys Cys Ser Ser Asn Gly
                 85                  90                  95

Arg Lys Arg Ala Arg Ala Gly Ile Gly Val Tyr Trp Gly Pro Gly His
            100                 105                 110

Pro Leu Asn Val Arg Ile Arg Leu Pro Gly Arg Gln Thr Asn Gln Arg
            115                 120                 125

Ala Glu Ile His Ala Ala Cys Lys Ala Val Met Gln Ala Lys Ala Gln
130                 135                 140

Asn Ile Ser Lys Leu Val Leu Tyr Thr Asp Ser Met Phe Thr Ile Asn
145                 150                 155                 160

Gly Ile Thr Asn Trp Val Gln Gly Trp Lys Asn Gly Trp Arg Thr
                165                 170                 175

Ser Thr Gly Lys Asp Val Ile Asn Lys Glu Asp Phe Met Glu Leu Asp
            180                 185                 190

Glu Leu Thr Gln Gly Met Asp Ile Gln Trp Met His Ile Pro Gly His
            195                 200                 205

Ser Gly Phe Val Gly Asn Glu Glu
210                 215

<210> SEQ ID NO 5
<211> LENGTH: 155
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 5

Met Leu Lys Gln Val Glu Ile Phe Thr Asp Gly Ser Cys Leu Gly Asn
  1               5                  10                  15

Pro Gly Pro Gly Gly Tyr Gly Ala Ile Leu Arg Tyr Arg Gly Arg Glu
                 20                  25                  30

Lys Thr Phe Ser Ala Gly Tyr Thr Arg Thr Thr Asn Asn Arg Met Glu
             35                  40                  45

Leu Met Ala Ala Ile Val Ala Leu Glu Ala Leu Lys Glu His Cys Glu
 50                  55                  60

Val Ile Leu Ser Thr Asp Ser Gln Tyr Val Arg Gln Gly Ile Thr Gln
 65                  70                  75                  80

Trp Ile His Asn Trp Lys Lys Arg Gly Trp Lys Thr Ala Asp Lys Lys
                 85                  90                  95

Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
            115                 120                 125

Glu Asn Glu Arg Cys Asp Glu Leu Ala Arg Ala Ala Met Asn Pro
130                 135                 140

Thr Leu Glu Asp Thr Gly Tyr Gln Val Glu Val
145                 150                 155

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Novel
      Sequence
```

```
<400> SEQUENCE: 6
acgctggccg ggagtcgaaa tgcttc                                          26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
ctgttcctgg cccacagagt cgccttgg                                        28

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
ggtctttctg acctggaatg agtgcagag                                       29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
cttgcctggt ttcgccctcc gattcttgt                                       29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
ttgattttca tgcccttctg aaacttccg                                       29

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
cctcatcctc tatggcaaac ttcttaaatc tggc                                 34

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Novel
      Sequence
```

```
<400> SEQUENCE: 12
gggcgccgtc ggtgtgg                                                    17

<210> SEQ ID NO 13
<211> LENGTH: 12
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 13
cgcgaauucg cg                                                         12

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: modified_base
<222> LOCATION: (4)
<223> OTHER INFORMATION: C= 5-methyl-C
<221> NAME/KEY: modified_base
<222> LOCATION: (8)
<223> OTHER INFORMATION: C= 5-methyl-C
<221> NAME/KEY: modified_base
<222> LOCATION: (11)..(15)
<223> OTHER INFORMATION: C=5-methyl-C

<400> SEQUENCE: 14
atgcattctg cccccaagga                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: modified_base
<222> LOCATION: (4)
<223> OTHER INFORMATION: C= 5-methyl-C
<221> NAME/KEY: modified_base
<222> LOCATION: (8)
<223> OTHER INFORMATION: C=5-methyl-C
<221> NAME/KEY: modified_base
<222> LOCATION: (11)..(12)
<223> OTHER INFORMATION: C= 5-methyl-C

<400> SEQUENCE: 15
atgcattctg ccaaaaagga                                                 20

<210> SEQ ID NO 16
<211> LENGTH: 11
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 16
ggctguctgc g                                                          11

<210> SEQ ID NO 17
<211> LENGTH: 19
```

```
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
tttttttttt tttttttt                                                    19

<210> SEQ ID NO 18
<211> LENGTH: 19
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 18
tttttttttt tttttttu                                                    19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19
tgcatccccc aggccaccat                                                  20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 20
uggugggcaa ugggcguguu                                                  20

<210> SEQ ID NO 21
<211> LENGTH: 17
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 21
gggcgccguc ggugugg                                                     17

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 22
acuccaccau aguacacucc                                                  20

<210> SEQ ID NO 23
```

```
<211> LENGTH: 25
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 23 ugguggggcgc cgucggugug ggcaa                                        25

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 24
ccacaccgac ggcgccc                                                  17

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 25
aacacgccca ttgcccacca                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: modified_base
<222> LOCATION: (2)..(4)
<223> OTHER INFORMATION: C=5-methyl-C
<221> NAME/KEY: modified_base
<222> LOCATION: (8)
<223> OTHER INFORMATION: C= 5-methyl-C
<221> NAME/KEY: modified_base
<222> LOCATION: (12)
<223> OTHER INFORMATION: C= 5-methyl-C
<221> NAME/KEY: modified_base
<222> LOCATION: (15)..(16)
<223> OTHER INFORMATION: C= 5-methyl-C
<221> NAME/KEY: modified_base
<222> LOCATION: (19)
<223> OTHER INFORMATION: C=5-methyl-C

<400> SEQUENCE: 26
gcccaagctg gcatccgtca                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 27
tccgtcatcg ctcctcaggg                                               20
```

```
<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 28
tcagtaatag gcccacatgg                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 29
ttcgtcatcg ctcctcaggg                                             20

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 30
tcagtaatag ccgccgcccc acatgg                                      26

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 31
tcagtaatag ccgcccccaca tgc                                        23

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 32
atgcattctg ccccaagga                                              19

<210> SEQ ID NO 33
<211> LENGTH: 47
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 33
gguggugguh ggcgccgucg guguggggcaa gagugcgcug accaucc              47
```